United States Patent
Ernst et al.

(10) Patent No.: US 9,873,733 B2
(45) Date of Patent: Jan. 23, 2018

(54) ANTI-STAPHYLOCOCCAL ANTIBODIES

(71) Applicants: MorphoSys AG, Planegg (DE); Universitaetsklinikum Tuebingen, Tuebingen (DE)

(72) Inventors: Christoph Michael Ernst, Tuebingen (DE); Andreas Paul Peschel, Tuebingen (DE); Alexandra Kraus, Munich (DE); Michael Tesar, Friedberg (DE)

(73) Assignees: MORPHOSYS AG., Planegg (DE); UNIVERSITAETSKLINIKUM TUEBINGEN, Tuebingen (DE)

( * ) Notice: Subject to any disclaimer, the term of this patent is extended or adjusted under 35 U.S.C. 154(b) by 36 days.

(21) Appl. No.: 14/647,459

(22) PCT Filed: Dec. 20, 2013

(86) PCT No.: PCT/EP2013/077633
§ 371 (c)(1),
(2) Date: May 27, 2015

(87) PCT Pub. No.: WO2014/096333
PCT Pub. Date: Jun. 26, 2014

(65) Prior Publication Data
US 2015/0368323 A1 Dec. 24, 2015

Related U.S. Application Data

(60) Provisional application No. 61/739,759, filed on Dec. 20, 2012, provisional application No. 61/775,716, filed on Mar. 11, 2013.

(30) Foreign Application Priority Data

Dec. 20, 2012 (EP) .................................. 12198480

(51) Int. Cl.
| | | |
|---|---|---|
| *C07K 16/12* | (2006.01) | |
| *A61K 39/40* | (2006.01) | |
| *A61K 39/00* | (2006.01) | |
| *A61K 38/12* | (2006.01) | |

(52) U.S. Cl.
CPC .......... *C07K 16/1271* (2013.01); *A61K 38/12* (2013.01); *A61K 39/40* (2013.01); *A61K 2039/505* (2013.01); *C07K 2317/30* (2013.01); *C07K 2317/34* (2013.01); *C07K 2317/55* (2013.01); *C07K 2317/76* (2013.01)

(58) Field of Classification Search
CPC .. A61K 2039/505; A61K 38/12; A61K 39/40; C07K 16/1271; C07K 2317/30; C07K 2317/34; C07K 2317/55; C07K 2317/76
See application file for complete search history.

(56) References Cited

U.S. PATENT DOCUMENTS

2008/0038287 A1* 2/2008 Meinke ............... C07K 14/195
424/190.1

FOREIGN PATENT DOCUMENTS

WO 2002094868 11/2002
WO WO 03/097813 A2 * 12/2003

OTHER PUBLICATIONS

Foster TJ. Nature Reviews Microbiology 3: 948-958, 2005.*
Campbell Am. In: Monoclonal Antibody Technology. Elsevier Science Publishers, The Netherlands, Chapter 1, pp. 1-32, 1984.*
PCT/EP2013/077633 ISR with written opinion dated Apr. 7, 2014.
EP/Provisional 12198480.1 ESR dated May 23, 2013.
Peschel et al.,"*Staphylococcus aureus* resistance to human defensins and evasion of neutrophil killing via the novel virulence factor MprF is based on modification of membrane lipids with l-lysine." J Exp Med. May 7, 2001;193(9):1067-76.
Weidenmaier et al., "DltABCD- and MprF-mediated cell envelope modifications of *Staphylococcus aureus* confer resistance to platelet microbicidal proteins and contribute to virulence in a rabbit endocarditis model." Infect Immun. Dec. 2005;73(12):8033-8.
Nishi et al., "Reduced content of lysyl-phosphatidylglycerol in the cytoplasmic membrane affects susceptibility to moenomycin, as well as vancomycin, gentamicin, and antimicrobial peptides, in *Staphylococcus aureus*." Antimicrob Agents Chemother. Dec. 2004;48(12):4800-7.
Ernst et al., "The bacterial defensin resistance protein MprF consists of separable domains for lipid lysinylation and antimicrobial peptide repulsion." PLoS Pathog. Nov. 2009;5(11):e1000660. doi: 10.1371/journal.ppat.1000660.
Jones et al., "Failures in clinical treatment of *Staphylococcus aureus* Infection with daptomycin are associated with alterations in surface charge, membrane phospholipid asymmetry, and drug binding." Antimicrob Agents Chemother. Jan. 2008;52(1):269-78.
Peleg et al., "Whole genome characterization of the mechanisms of daptomycin resistance in clinical and laboratory derived isolates of *Staphylococcus aureus*." PLoS One. 2012;7(1):e28316. doi: 10.1371/journal.pone.0028316.
Maloney et al., "The two-domain LysX protein of Mycobacterium tuberculosis is required for production of lysinylated phosphatidylglycerol and resistance to cationic antimicrobial peptides." PLoS Pathog. Jul. 2009;5(7):e1000534. doi:10.1371/journal.ppat.1000534.
Thedieck et al., "The MprF protein is required for lysinylation of phospholipids in listerial membranes and confers resistance to cationic antimicrobial peptides (CAMPs) on Listeria monocytogenes." Mol Microbiol. Dec. 2006;62(5):1325-39.
Slavetinsky et al., "Alanyl-phosphatidylglycerol and lysyl-phosphatidylglycerol are translocated by the same MprF flippases and have similar capacities to protect against the antibiotic daptomycin in *Staphylococcus aureus*." Antimicrob Agents Chemother. Jul. 2012;56(7):3492-7. doi: 10.1128/AAC.00370-12.

(Continued)

Primary Examiner — S. Devi
(74) Attorney, Agent, or Firm — Licata & Tyrrell P.C.

(57) ABSTRACT

This disclosure generally relates to antibodies or fragments thereof which interact with the bacterial protein MprF. The disclosure further discloses antibodies, which bind to specific extracellular motifs of MprF. The disclosure further relates to therapeutics comprising MprF-specific antibodies and methods of treatment using MprF-specific antibodies or fragments thereof.

10 Claims, 17 Drawing Sheets

(56) References Cited

OTHER PUBLICATIONS

Figure 1:
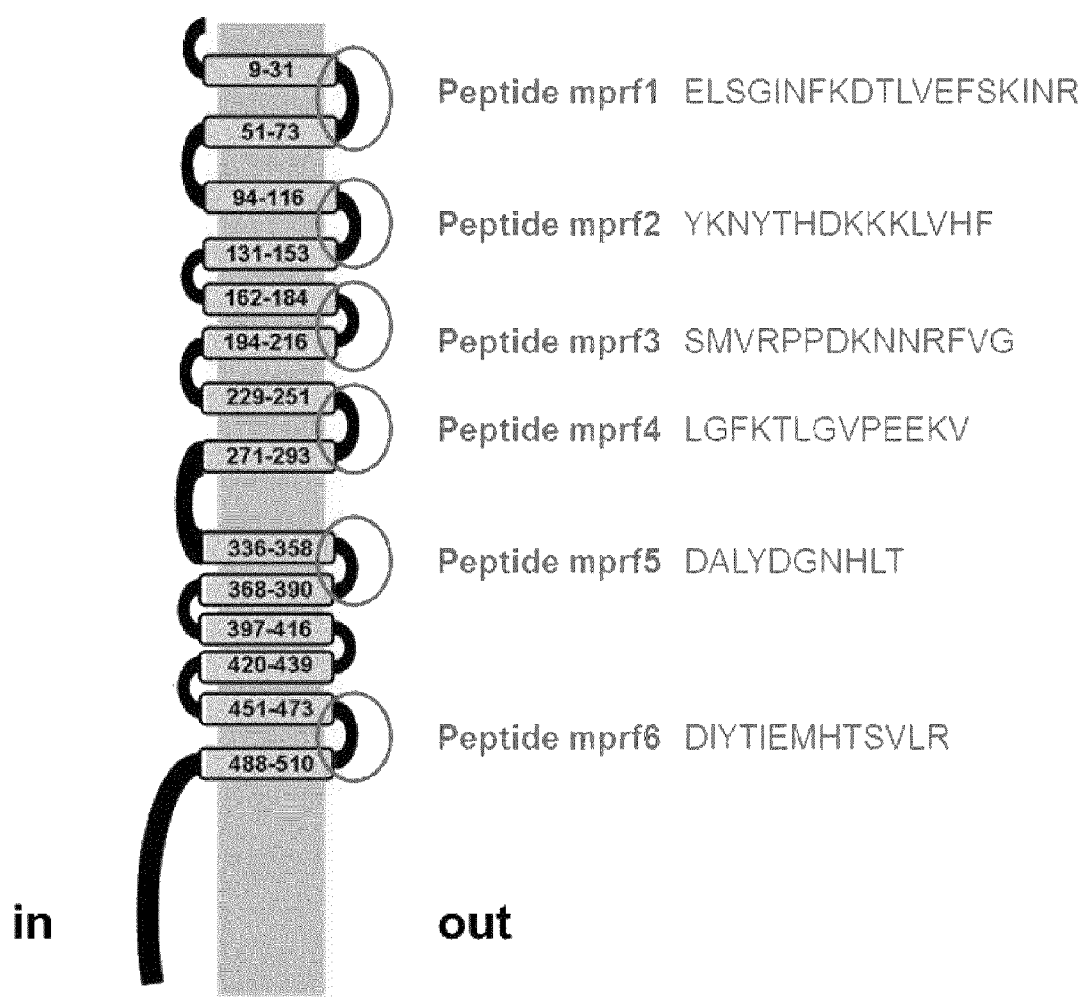

Ruzin A et al., "Inactivation of mprF affects vancomycin susceptibility in *Staphylococcus aureus*" Biochimica Et Biophysica Acta—General Subjects, Elsevier Science Publishers, NL, vol. 1621, No. 2, May 2, 2003 (May 2, 2003), pp. 117-121.

Weidenmaier Christopher et al., "Bacterial resistance to antimicrobial host defenses: An emerging target for novel antiinfective strategies?", Current Drug Targets, Bentham Science Publisher, US, vol. 4, No. 8, Nov. 1, 2003 (Nov. 1, 2003), pp. 643-649.

Y. Oku., "Characterization of the *Staphylococcus aureus* mprF gene, involved in lysinylation of phosphatidylglycerol", Microbiology, vol. 150, No. 1, Jan. 1, 2004 (Jan. 1, 2004), pp. 45-51.

\* cited by examiner

FIGURE 2
Antigen: linear peptide, loop 1
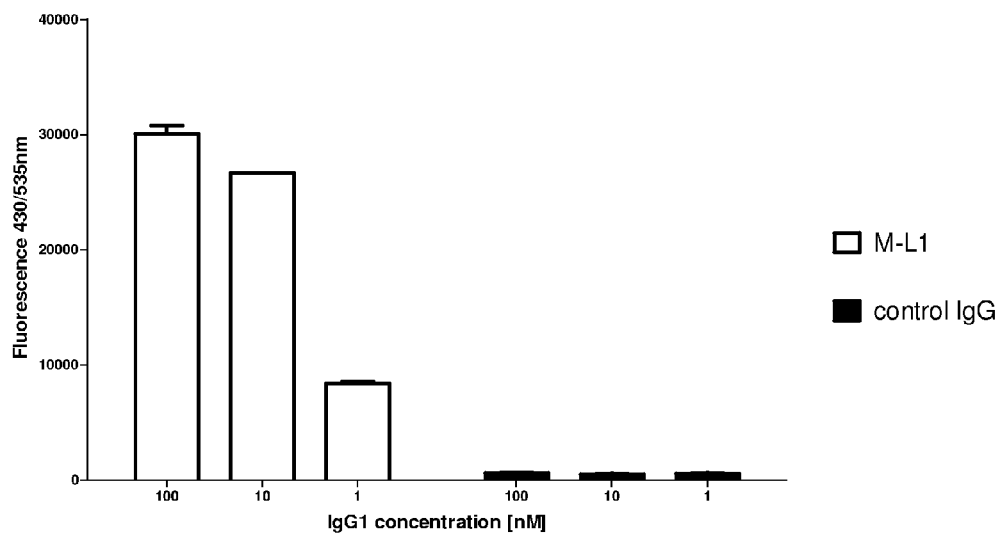
Antigen: cyclic peptide, loop 1
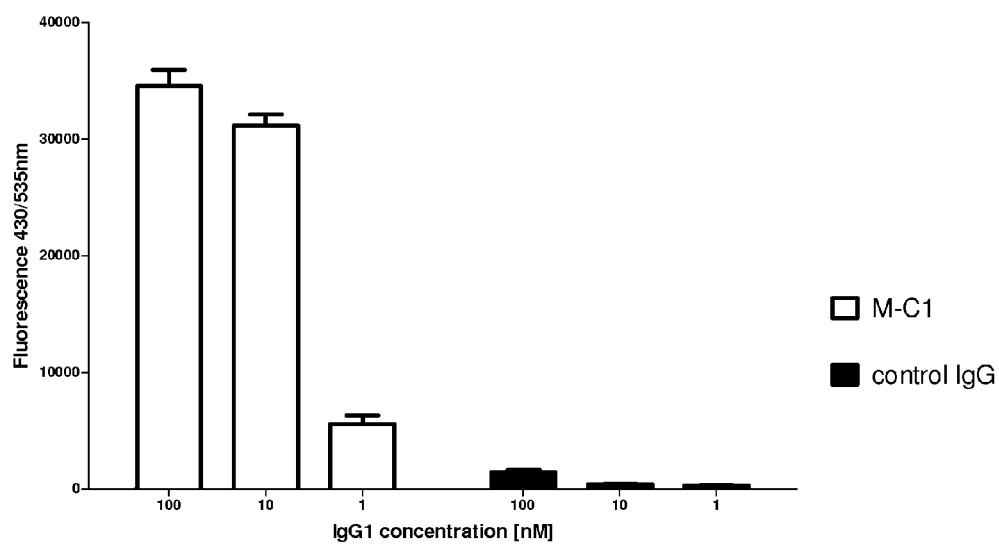

FIGURE 3
Antigen: linear peptide, loop 4
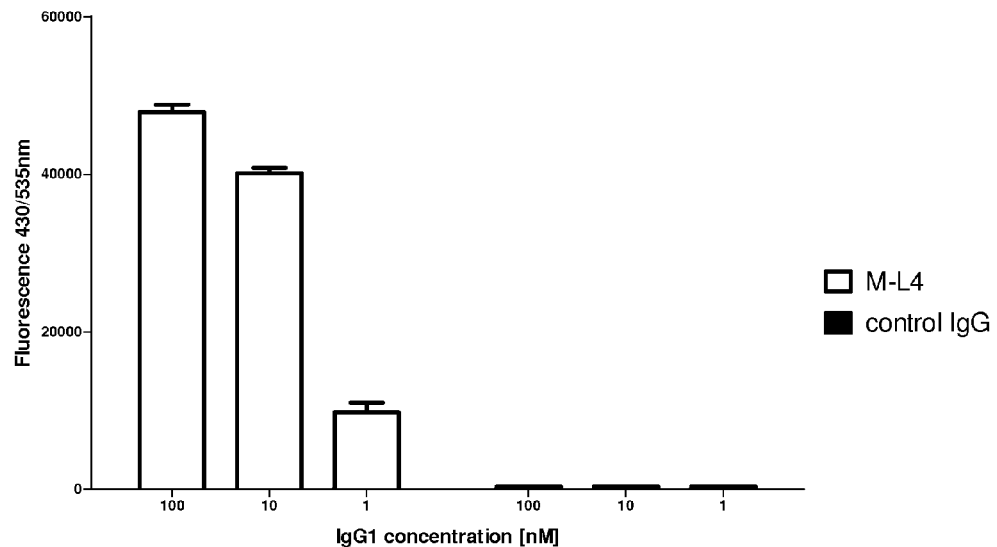
Antigen: cyclic peptide, loop 4
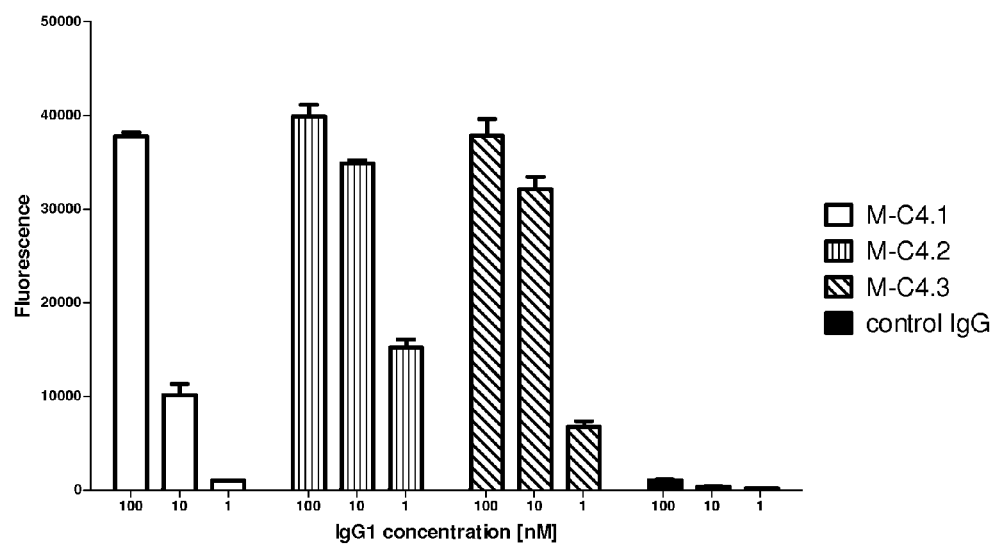

FIGURE 4
Antigen: cyclic peptide, loop 5
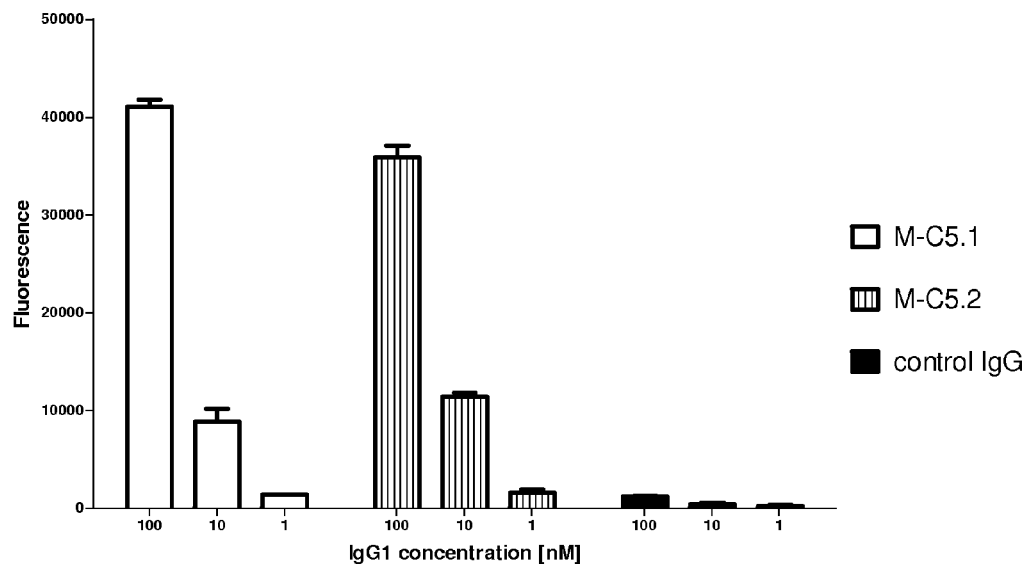
Antigen: cyclic peptide, loop 6
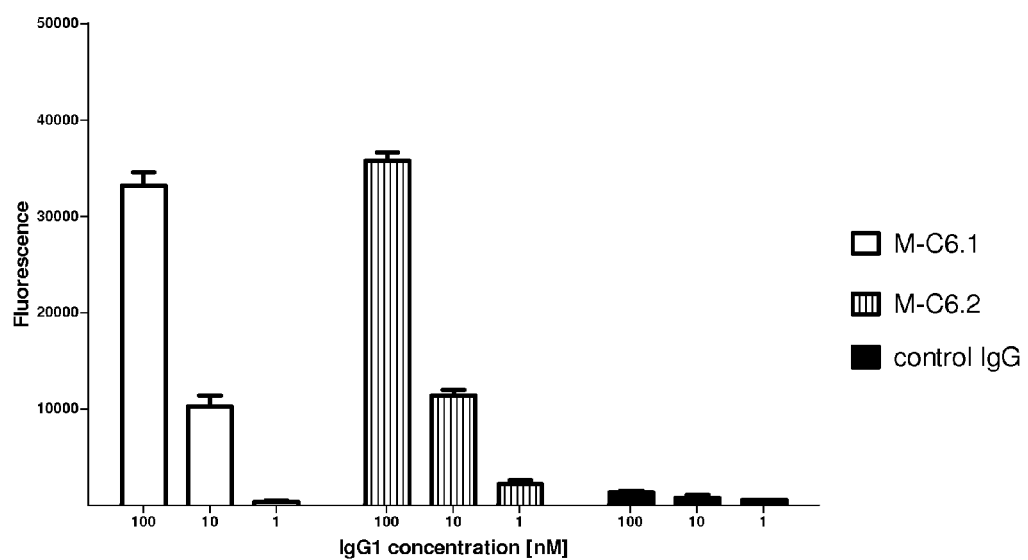

FIG. 12A

```
MRSA252    (1) MNQEVKNKIFSILKITFATALFIFV ITLYRELSGINFKDTLVEFSKINR
MSSA479    (1) MNQEVKNKIFSILKITFATALFIFV ITLYRELSGINFKDTLVEFSKINR
    MW2    (1) MNQEVKNKIFSILKITFATALFIFV ITLYRELSGINFKDTLVEFSKINR
   N315    (1) MNQEVKNKIFSILKITFATALFIFVAITLYRELSGINFKDTLVEFSKINR
NCTC8325   (1) MNQEVKNKIFSILKITFATALFIFVAITLYRELSGINFKDTLVEFSKINR
 USA300    (1) MNQEVKNKIFSILKITFATALFIFVAITLYRELSGINFKDTLVEFSKINR
               51                                              100
MRSA252   (51) MSLVLLFIGGGASLVILSMYDVILSRALKMDISLGKVLRVSYIINALNAI
MSSA479   (51) MSLVLLFIGGGASLVILSMYDVILSRALKMDISLGKVLRVSYIINALNAI
    MW2   (51) MSLVLLFIGGGASLVILSMYDVILSRALKMDISLGKVLRVSYIINALNAI
   N315   (51) MSLVLLFIGGGASLVILSMYDVILSRALKMDISLGKVLRVSYIINALNAI
NCTC8325  (51) MSLVLLFIGGGASLVILSMYDVILSRALKMDISLGKVLRVSYIINALNAI
 USA300   (51) MSLVLLFIGGGASLVILSMYDVILSRALKMDISLGKVLRVSYIINALNAI
               101                                             150
MRSA252  (101) VGFGGFIGAGVRAMVYKNYTHDKKKLVHFISLILISMLTGLSLLSLLIVF
MSSA479  (101) VGFGGFIGAGVRAMVYKNYTHDKKKLVHFISLILISMLTGLSLLSLLIVF
    MW2  (101) VGFGGFIGAGVRAMVYKNYTHDKKKLVHFISLILISMLTGLSLLSLLIVF
   N315  (101) VGFGGFIGAGVRAMVYKNYTHDKKKLVHFISLILISMLTGLSLLSLLIVF
NCTC8325 (101) VGFGGFIGAGVRAMVYKNYTHDKKKLVHFISLILISMLTGLSLLSLLIVF
 USA300  (101) VGFGGFIGAGVRAMVYKNYTHDKKKLVHFISLILISMLTGLSLLSLLIVF
               151                                             200
MRSA252  (151) HVFDASLILNKITWVRWVLYAVSLFLPLFIIYSMVRPPDKNNR VGLYCT
MSSA479  (151) HVFDASLIL KITWVRWVLY VS FLPLFIIYSMVRPPDKNNR VGLYCT
    MW2  (151) HVFDASLIL KITWVRWVLY VS FLPLFIIYSMVRPPDKNNR VGLYCT
   N315  (151) HVFDASLIL KITWVRWVLY VS FLPLFIIYSMVRPPDKNNR VGLYCT
NCTC8325 (151) HVFDASLIL KITWVRWVLY VS FLPLFIIYSMVRPPDKNNR VGLYCT
 USA300  (151) HVFDASLIL KITWVRWVLY VS FLPLFIIYSMVRPPDKNNR VGLYCT
               201                                             250
MRSA252  (201) LVSCVEWLAAAVVLYFCGVIVDVHVSFMSFIAIFIIAALSGLVSFIPGGF
MSSA479  (201) LVSCVEWLAAAVVLYFCGVIVD HVSFMSFIAIFIIAALSGLVSFIPGGF
    MW2  (201) LVSCVEWLAAAVVLYFCGVIVD HVSFMSFIAIFIIAALSGLVSFIPGGF
   N315  (201) LVSCVEWLAAAVVLYFCGVIVD HVSFMSFIAIFIIAALSGLVSFIPGGF
NCTC8325 (201) LVSCVEWLAAAVVLYFCGVIVD HVSFMSFIAIFIIAALSGLVSFIPGGF
 USA300  (201) LVSCVEWLAAAVVLYFCGVIVD HVSFMSFIAIFIIAALSGLVSFIPGGF
               251                                             300
MRSA252  (251) GAFDLVVLLGFKTLGVPEEKVLLMLLLYRFAYYFVPVIIALILSSFEFGT
MSSA479  (251) GAFDLVVLLGFKTLGVPEEKVLLMLLLYRFAYYFVPVIIALILSSFEFGT
    MW2  (251) GAFDLVVLLGFKTLGVPEEKVLLMLLLYRFAYYFVPVIIALILSSFEFGT
   N315  (251) GAFDLVVLLGFKTLGVPEEKVLLMLLLYRFAYYFVPVIIALILSSFEFGT
NCTC8325 (251) GAFDLVVLLGFKTLGVPEEKVLLMLLLYRFAYYFVPVIIALILSSFEFGT
 USA300  (251) GAFDLVVLLGFKTLGVPEEKVLLMLLLYRFAYYFVPVIIALILSSFEFGT
               301                                             350
MRSA252  (301) SAKKYIEGSKYFIPAKDVTSFLMSYQKDIIAKIPSLSLAILVFFTSMIFF
MSSA479  (301) SAKKYIEGSKYFIPAKDVTSFLMSYQKDIIAKIPSLSLAILVFFTSMIFF
    MW2  (301) SAKKYIEGSKYFIPAKDVTSFLMSYQKDIIAKIPSLSLAILVFFTSMIFF
   N315  (301) SAKKYIEGSKYFIPAKDVTSFLMSYQKDIIAKIPSLSLAILVFFTSMIFF
NCTC8325 (301) SAKKYIEGSKYFIPAKDVTSFLMSYQKDIIAKIPSLSLAILVFFTSMIFF
 USA300  (301) SAKKYIEGSKYFIPAKDVTSFLMSYQKDIIAKIPSLSLAILVFFTSMIFF
               351                                             400
MRSA252  (351) VNNLTIVYDALYDGNHLTYY LLAIHTSACLLLLLNVVGIYKQSRRAII
MSSA479  (351) VNNLTIVYDALYDGNHLTYY LLAIHTSACLLLLLNVVGIYKQSRRAII
    MW2  (351) VNNLTIVYDALYDGNHLTYY LLAIHTSACLLLLLNVVGIYKQSRRAII
   N315  (351) VNNLTIVYDALYDGNHLTYY LLAIHTSACLLLLLNVVGIYKQSRRAII
NCTC8325 (351) VNNLTIVYDALYDGNHLTYY LLAIHTSACLLLLLNVVGIYKQSRRAII
 USA300  (351) VNNLTIVYDALYDGNHLTYY LLAIHTSACLLLLLNVVGIYKQSRRAII
               401                                             450
MRSA252  (401) AMISI LIIVATLFTYASYILITWLVIIFALLIVAFRRARRLKRP RMRN
MSSA479  (401) AMISI LI VAT FTYASYILITWL III LLIVAFRRARRLKRP RMRN
    MW2  (401) AMISI LI VAT FTYASYILITWL III LLIVAFRRARRLKRP RMRN
   N315  (401) AMISI LI VAT FTYASYILITWL III LLIVAFRRARRLKRP RMRN
```

FIG. 12B

```
NCTC8325  (401) AMISI LI VAT FTYASYILITWL IIF LLIVAFRRARRLKRP RMRN
 USA300   (401) AMISI LI VAT FTYASYILITWL IIF LLIVAFRRARRLKRP RMRN
                 451                                              500
 MRSA252  (451)  VAMLLFS FILY NHIFIAGTFYALD YTIEMHTSVL YYFW TILIIA
 MSSA479  (451)  VAMLLFS FILY NHIFIAGT YALD YTIEMHTSVL YYFW TILIIA
    MW2   (451)  VAMLLFS FILY NHIFIAGT YALD YTIEMHTSVL YYFW TILIIA
    N315  (451)  VAMLLFS FILY NHIFIAGT YALD YTIEMHTSVL YYFW TILIIA
NCTC8325  (451)  VAMLLFS FILY NHIFIAGT YALD YTIEMHTSVL YYFW TILIIA
 USA300   (451)  VAMLLFS FILY NHIFIAGT YALD YTIEMHTSVL YYFW TILIIA
                 501                                              550
 MRSA252  (501) II GA IAWLFDYQFSKVRISSNIE CEEIIDQYGGNYLSHLIYSGDKQFF
 MSSA479  (501) II GM IAWLFDYQFSKVRISS IE CEEII QYGGNYLSHLIYSGDKQFF
    MW2   (501) II GM IAWLFDYQFSKVRISS IE CEEII QYGGNYLSHLIYSGDKQFF
    N315  (501) II GM IAWLFDYQFSKVRISS IE CEEII QYGGNYLSHLIYSGDKQFF
NCTC8325  (501) II GM IAWLFDYQFSKVRISS IE CEEII QYGGNYLSHLIYSGDKQFF
 USA300   (501) II GM IAWLFDYQFSKVRISS IE CEEII QYGGNYLSHLIYSGDKQFF
                 551                                              600
 MRSA252  (551) TNEDKNAFLMYRYKASSLVVLGDP GDENAFDELLEAFYNYAEYLGYDVI
 MSSA479  (551) TNE NK AFLMYRYKASSLVVLGDP GDENAFDELLEAFYNYAEYLGYDVI
    MW2   (551) TNE NK AFLMYRYKASSLVVLGDP GDENAFDELLEAFYNYAEYLGYDVI
    N315  (551) TNE NK AFLMYRYKASSLVVLGDP GDENAFDELLEAFYNYAEYLGYDVI
NCTC8325  (551) TNE NK AFLMYRYKASSLVVLGDP GDENAFDELLEAFYNYAEYLGYDVI
 USA300   (551) TNE NK AFLMYRYKASSLVVLGDP GDENAFDELLEAFYNYAEYLGYDVI
                 601                                              650
 MRSA252  (601) FYQVTDQHMPLYHNFGNQFFKLGEEAIIDLTQFSTSGKKRRGFRATLNKF
 MSSA479  (601) FYQVTDQHMPLYHNFGNQFFKLGEEAIIDLTQFSTSGKKRRGFRATLNKF
    MW2   (601) FYQVTDQHMPLYHNFGNQFFKLGEEAIIDLTQFSTSGKKRRGFRATLNKF
    N315  (601) FYQVTDQHMPLYHNFGNQFFKLGEEAIIDLTQFSTSGKKRRGFRATLNKF
NCTC8325  (601) FYQVTDQHMPLYHNFGNQFFKLGEEAIIDLTQFSTSGKKRRGFRATLNKF
 USA300   (601) FYQVTDQHMPLYHNFGNQFFKLGEEAIIDLTQFSTSGKKRRGFRATLNKF
                 651                                              700
 MRSA252  (651) DELNISFEIIEPPFSTEFINELQHVSDLWLDNRQEMHFSVG FNETYLSK
 MSSA479  (651) DELNISFEIIEPPFSTEFINELQHVSDLWLDNRQEMHFSVG FNE YLSK
    MW2   (651) DELNISFEIIEPPFSTEFINELQHVSDLWLDNRQEMHFSVG FNE YLSK
    N315  (651) DELNISFEIIEPPFSTEFINELQHVSDLWLDNRQEMHFSVG FNE YLSK
NCTC8325  (651) DELNISFEIIEPPFSTEFINELQHVSDLWLDNRQEMHFSVGEFNE YLSK
 USA300   (651) DELNISFEIIEPPFSTEFINELQHVSDLWLDNRQEMHFSVGEFNE YLSK
                 701                                              750
 MRSA252  (701) APIGVMRNENNEVIAFCSLMPTYFNDAISVDLIRWLPELDLPLMDGLYLH
 MSSA479  (701) APIGVMRNE NEVIAFCSLMPTYFNDAISVDLIRWLPELDLPLMDGLYLH
    MW2   (701) APIGVMRNE NEVIAFCSLMPTYFNDAISVDLIRWLPELDLPLMDGLYLH
    N315  (701) APIGVMRNE NEVIAFCSLMPTYFNDAISVDLIRWLPELDLPLMDGLYLH
NCTC8325  (701) APIGVMRNE NEVIAFCSLMPTYFNDAISVDLIRWLPELDLPLMDGLYLH
 USA300   (701) APIGVMRNE NEVIAFCSLMPTYFNDAISVDLIRWLPELDLPLMDGLYLH
                 751                                              800
 MRSA252  (751) MLLWSKEQGYTKFNMGMATLSNVGQLHYSYLRERLAGRVFEHFNGLYRFQ
 MSSA479  (751) MLLWSKEQGYTKFNMGMATLSNVGQLHYSYLRERLAGRVFEHFNGLYRFQ
    MW2   (751) MLLWSKEQGYTKFNMGMATLSNVGQLHYSYLRERLAGRVFEHFNGLYRFQ
    N315  (751) MLLWSKEQGYTKFNMGMATLSNVGQLHYSYLRERLAGRVFEHFNGLYRFQ
NCTC8325  (751) MLLWSKEQGYTKFNMGMATLSNVGQLHYSYLRERLAGRVFEHFNGLYRFQ
 USA300   (751) MLLWSKEQGYTKFNMGMATLSNVGQLHYSYLRERLAGRVFEHFNGLYRFQ
                 801                         840
 MRSA252  (801) GLRRYKSKYNPNWEPRFLVYRKDNSLWESLSKVMRVIRHK
 MSSA479  (801) GLRRYKSKYNPNWEPRFLVYRKDNSLWESLSKVMRVIRHK
    MW2   (801) GLRRYKSKYNPNWEPRFLVYRKDNSLWESLSKVMRVIRHK
    N315  (801) GLRRYKSKYNPNWEPRFLVYRKDNSLWESLSKVMRVIRHK
NCTC8325  (801) GLRRYKSKYNPNWEPRFLVYRKDNSLWESLSKVMRVIRHK
 USA300   (801) GLRRYKSKYNPNWEPRFLVYRKDNSLWESLSKVMRVIRHK
```

ANTI-STAPHYLOCOCCAL ANTIBODIES

CROSS REFERENCE

This application is the U.S. National Phase of PCT/EP2013/077633, filed Dec. 20, 2013, which claims benefit of the U.S. provisional application Ser. No. 61/739,759 filed Dec. 20, 2012 and of the U.S. provisional application Ser. No. 61/775,716 filed Mar. 11, 2013, which both are incorporated by reference in its entirety.

BACKGROUND OF THE INVENTION

This disclosure generally relates to antibodies or fragments thereof which interact with the bacterial protein MprF. In particular antibodies or fragments are disclosed, which bind to specific extracellular motifs of MprF. The disclosure further relates to therapeutics comprising MprF-specific antibodies and methods of treatment using MprF-specific antibodies or fragments thereof.

BACKGROUND OF THE INVENTION

*Staphylococcus aureus* (*S. aureus*) is a facultative anaerobic, gram positive, spherical bacterium considered to be an opportunistic pathogen. *S. aureus* commonly colonizes the nose, skin and mucosal surfaces of healthy humans. Approximately 20-30% of the population is colonized with *S. aureus* at any given time. These bacteria often cause minor infections, such as pimples and boils in healthy individuals. Normally, mucosal and epidermal barriers (skin) protect against *S. aureus* infections. Interruption of these natural barriers as a result of injuries—such as burns, trauma or surgical procedures—dramatically increases the risk of infection and could cause severe and/or systemic infections. Furthermore also diseases that compromise the immune system (e.g., diabetes, end-stage renal disease, cancer, AIDS and other viral infections), but also immunosuppressive therapies—e.g. as radiation, chemotherapeutic and transplantation therapies—increase the risk of infection. Opportunistic *S. aureus* infections can become quite serious, causing endocarditis, bacteremia, osteomyelitis and abscess formation, which might result in severe morbidity or mortality.

*S. aureus* is a leading cause of bloodstream, skin, soft tissue, and lower respiratory tract infections worldwide. The frequencies of both nosocomial and community-acquired infections have increased steadily over the years. During a localized infection such as pneumonia in humans, approx. 40% of patients with *S. aureus* pneumonia develop blood stream infections and disseminated disease. The dissemination of the bacterial infection can lead to blood stream infection and distant organ seeding. The blood stream infection can lead to septicemia, a rapidly progressing and frequently fatal complication of *S. aureus* infections.

In addition, treatment of these infections has become more challenging due to the emergence of multi-drug resistant strains. In almost all developed countries, resistance to antibiotics in methicillin-resistant *S. aureus* strains (MRSA) is a major problem in hospitals and other healthcare settings and although data on structure and function of *S. aureus* proteins became more comprehensive the development of an effective vaccine remains a challenge. Notably, the incidence rate of all invasive MRSA infections, including those outside of hospitals, in comparison to other bacterial pathogens is quite high and 20% of these infections result in death.

In addition the occurrence of acquired resistance to vancomycin further limited the options for treatment of severe *S. aureus* infections.

MprF was identified as the enzyme catalyzing Lysyl-phosphatidylglycerol (Lys-PG) biosynthesis in *Staphylococcus aureus* which is a major component of the bacterial membrane (Peschel et al. 2001). MprF does not only synthesize Lys-PG but also accomplishes the translocation of Lys-PG from the inner to the outer leaflet of the membrane or lipid bilayer resulting in a reduced negative charge of the membrane surface. The mortality of mice infected with a *S. aureus* mutant strain with an inactivated MprF gene was found to be significantly lower than that of mice infected with the wildtype strain (Peschel et al, 2001). In addition the mutant strain was cleared more efficiently from the bloodstream and showed impaired capacity to proliferate within cardiac vegetations compared to the wildtype in a model of endovascular infection of rabbits (Weidenmaier et al., 2005). Together these findings strongly support the hypothesis of a role of MprF in Staphylococcal virulence (Peschel et al., 2001).

Furthermore, in *S. aureus* Lys-PG and MprF also affect the susceptibility to cationic antibiotics, e.g. gentamycin (Nishi et al., 2004), and daptomycin (Ernst et al., 2009). The lipopeptide daptomycin is an approved last-resort antibiotic for the treatment of methicillin- and vancomycin resistant *S. aureus*. An analysis of daptomycin non-susceptible clinical strains revealed that many of them harboured point mutations in the mprF gene, which were interpreted as gain-of-function mutations (Jones et al., 2008, Peleg et al., 2012).

MprF is highly conserved within laboratory and clinically relevant strains of the species *Staphylococcus aureus* (FIGS. 12A and 12B). The importance of Lys-PG in resistance to antimicrobial peptides has also been demonstrated in other bacterial species. A mutant of *Mycobacterium tuberculosis* defective in Lys-PG production showed increased sensitivity to vancomycin and defective growth in mouse and guinea pig lungs and reduced pathology relative to wild type (Maloney et al., 2009). Deletion of an mprF-homologue in *Listeria monocytogenes* resulted in a strain less resistant to specific antimicrobial peptides, with reduced ability to infect macrophages and epithelial cells and the deletion mutant was attenuated in a mouse infection model (Thedieck et al., 2006). Recently a publication described that the expression of an MprF-homologue from *Clostridium perfringens* in a *S. aureus* mprF-deletion mutant restores the resistance towards daptomycin indicating a role of *C. perfringens* MprF in resistance to antimicrobial peptides (Slavetinsky et al., 2012).

Thus, an object of the invention is the provision of products and methods for prophylaxis and therapy of clinically complex *S. aureus* infection. In particular the present disclosure provides antibodies or fragments specific to MprF from *S. aureus*, wherein the antibody has protective capacity in vivo, against clinically complex *S. aureus* infection. Furthermore, the present disclosure provides antibodies or fragments specific for MprF which enhance the susceptibility of *S. aureus* to antimicrobial peptides and antibiotics which interfere with the bacterial membrane. Furthermore, the present disclosure provides a combinatorial therapy comprising MprF antibodies or fragments together with cationic antimicrobial peptides (CAMP) or CAMP-like antibiotics, e.g. daptomycin, for the treatment of bacterial infections.

SUMMARY OF THE INVENTION

The applicant for the first time discloses antibodies or antibody fragments which specifically bind to MprF. MprF antibodies or antibody fragments interfering with the translocation of lysyl-phosphatidyglycerol provide a promising approach to enhance susceptibility of multi-resistant *S. aureus* to antimicrobial peptides and antibiotics, like e.g. daptomycin. Additionally, since the structure of specific extracellular loops of MprF are highly conserved not only within *S. aureus* strains but also within MprF orthologues from other gram-positive or gram-negative bacteria the present disclosure provides a therapeutic approach bearing high potential in broad infectious disease treatments.

The antibodies were identified upon selection strategies using recombinant cyclic and linear peptides mimicking the extracellular loops of MprF. Based on ELISA screening binding of specific antibodies to each of the peptides were detected. Identified clones were converted into IgG format and expressed in eukaryotic cells. After purification further characterization of the selected antibodies confirmed binding to *S. aureus* in a whole cell ELISA approach. Additionally, further functional analyses were performed to demonstrate functional activity of the selected antibodies. Consequently, an activity and efficacy of MprF-specific antibodies or antibody fragments is predicted in human in treatment of *S. aureus* infection, specifically of infection caused by antibiotic resistant *S. aureus* strains.

FIGURE LEGENDS

FIG. 1: Membrane topology of MprF of *Staphylococcus aureus* showing Peptide mprf1 (SEQ ID NO:2), Peptide mprf2 (SEQ ID NO:3), Peptide mprf3 (SEQ ID NO:4), Peptide mprf4 (SEQ ID NO:5), Peptide mprf5 (SEQ ID NO:6), Peptide mprf6 (SEQ ID NO:7).

FIG. 2: Specific binding of selected IgGs on linear or cyclic peptide was analyzed by ELISA according to Example 3. Respective biotinylated linear peptide representing loop 1 and cyclic peptide representing loop 1 were incubated with IgGs (M-L1, M-C1) in PBS. M-L1 was shown to specifically bind to linear loop 1 peptide in a dose-dependent manner. M-C1 was shown to specifically bind to cyclic loop 1 peptide in a dose-dependent manner.

FIG. 3: Specific binding of selected IgGs on linear or cyclic peptide was analyzed by ELISA according to Example 3. Respective biotinylated linear peptide representing loop 4 and cyclic peptide representing loop 4 were incubated with IgGs (M-L4, M-C4.1, M-C4.2 and M-C4.3) in PBS. M-L4 was shown to specifically bind to linear loop 4 peptide in a dose-dependent manner. M-C4.1, M-C4.2 and M-C4.3 were shown to specifically bind to cyclic loop 4 peptide in a dose-dependent manner.

FIG. 4: Specific binding of selected IgGs on linear or cyclic peptide was analyzed by ELISA according to Example 3. Respective biotinylated cyclic peptides representing loop 5 or loop 6 were incubated with IgGs (M-C5.1, M-C5.2, M-C6.1 and M-C6.2) in PBS. M-C5.1 and M-C5.2, were shown to specifically bind to cyclic loop 5 peptide in a dose-dependent manner. M-C6.1 and M-C6.2 were shown to specifically bind to cyclic loop 6 peptide in a dose-dependent manner.

Figure 5:
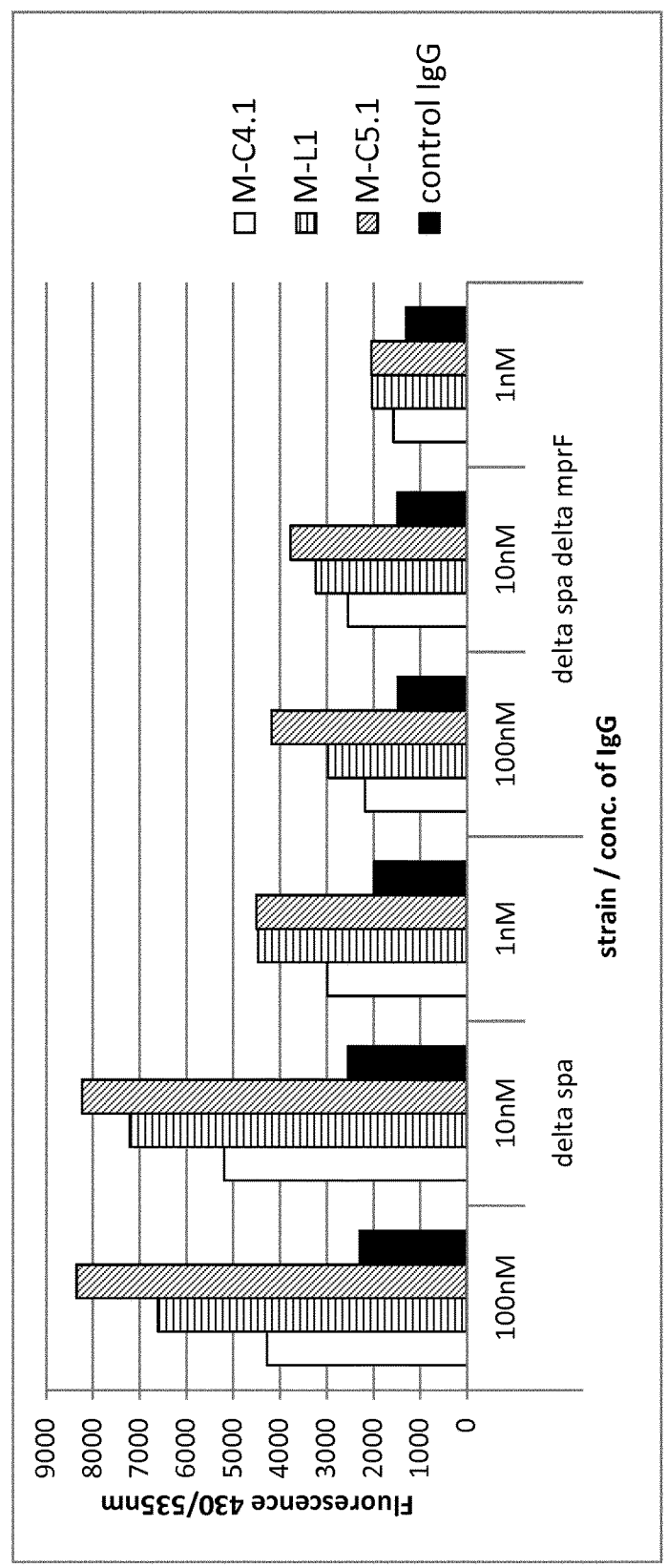

FIG. 5: Specific binding of selected IgGs on *S. aureus* was analyzed by ELISA according to Example 4. Representative antibodies M-L1, M-C4.1 and M-C5.1 proved to detect MprF on *S. aureus* and showed significantly weaker binding to *S. aureus* mutants lacking MprF expression (delta spa delta mprF).

Figure 6:
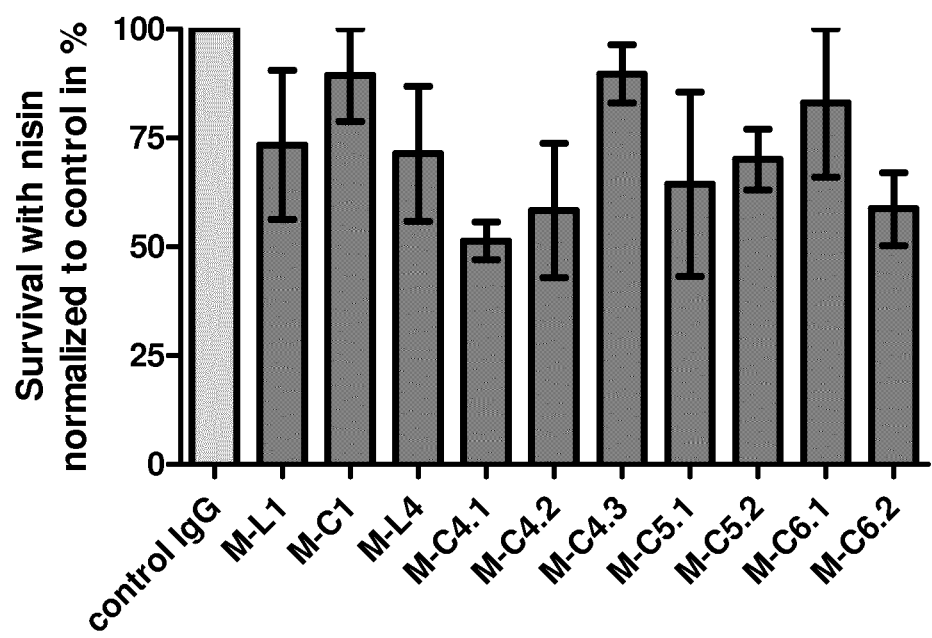

FIG. 6: Killing of *Staphylococcus aureus* by nisin was analyzed in the presence and absence of MprF antibodies. An anti-lysozyme antibody was used as a negative control. Antibodies of the present invention increased the sensitivity of *Staphylococcus aureus* towards nisin.

Figure 7:
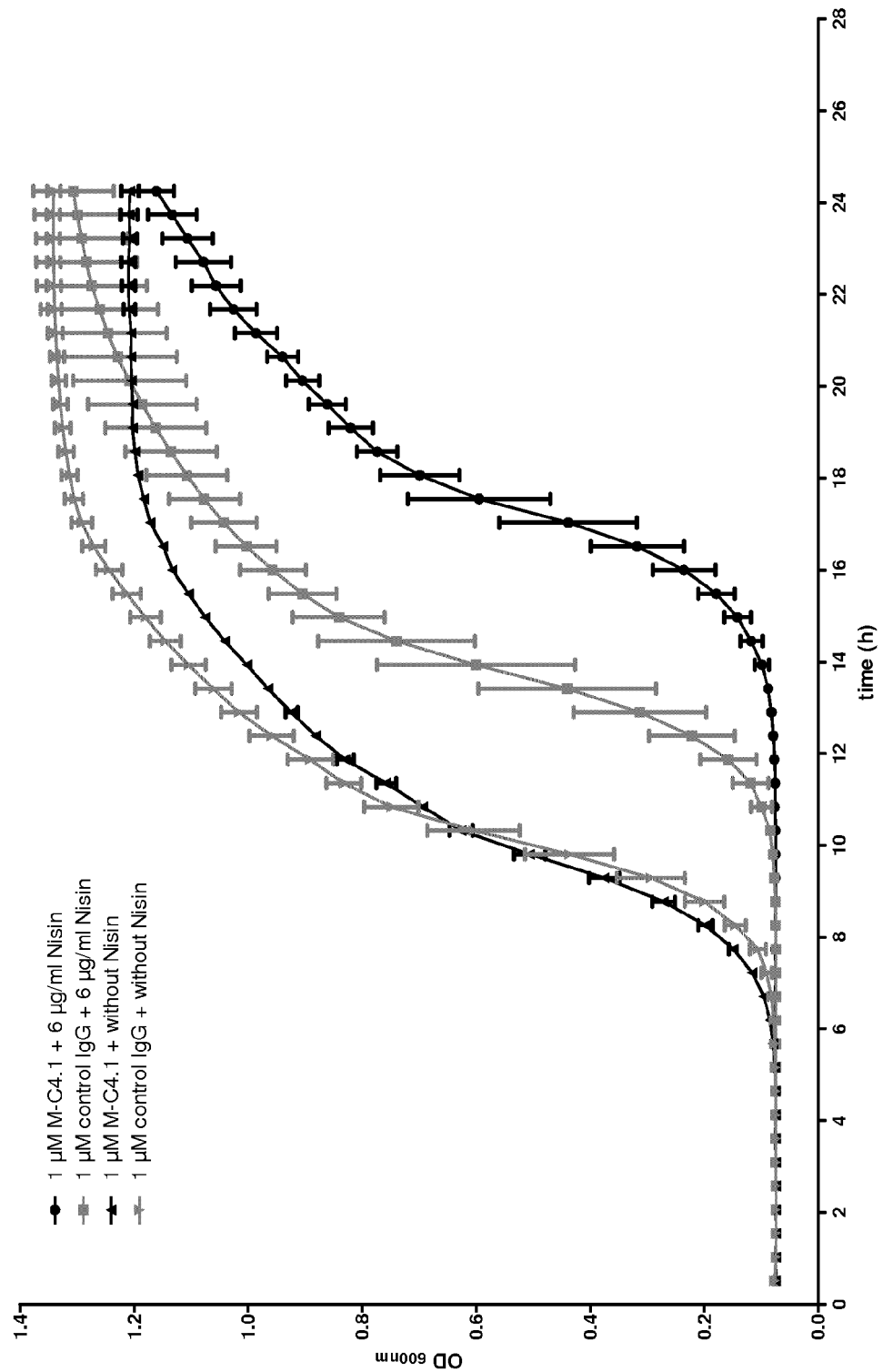

FIG. 7: Growth of *Staphylococcus aureus* by nisin was analyzed in the presence and absence of MprF antibodies. An anti-lysozyme antibody was used as a negative control. Antibodies of the present invention increased the sensitivity of *Staphylococcus aureus* towards nisin and reduced growths of bacteria.

Figure 8:
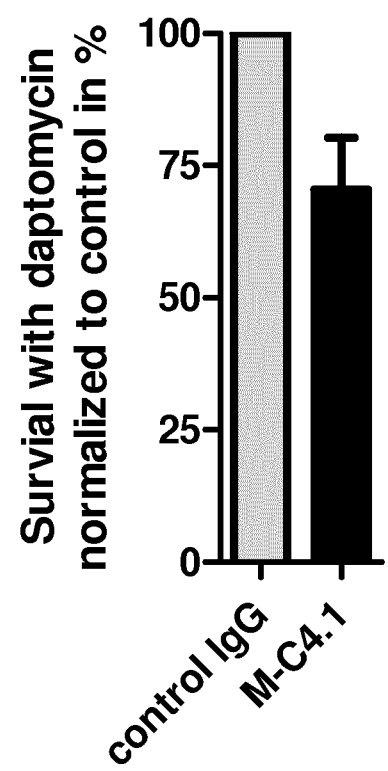

FIG. 8: Killing of *Staphylococcus aureus* by daptomycin was analyzed in the presence and absence of the MprF antibody M-C4.1. An anti-lysozyme antibody was used as a negative control. M-C4.1 increased the sensitivity of *Staphylococcus aureus* towards daptomycin.

Figure 9:
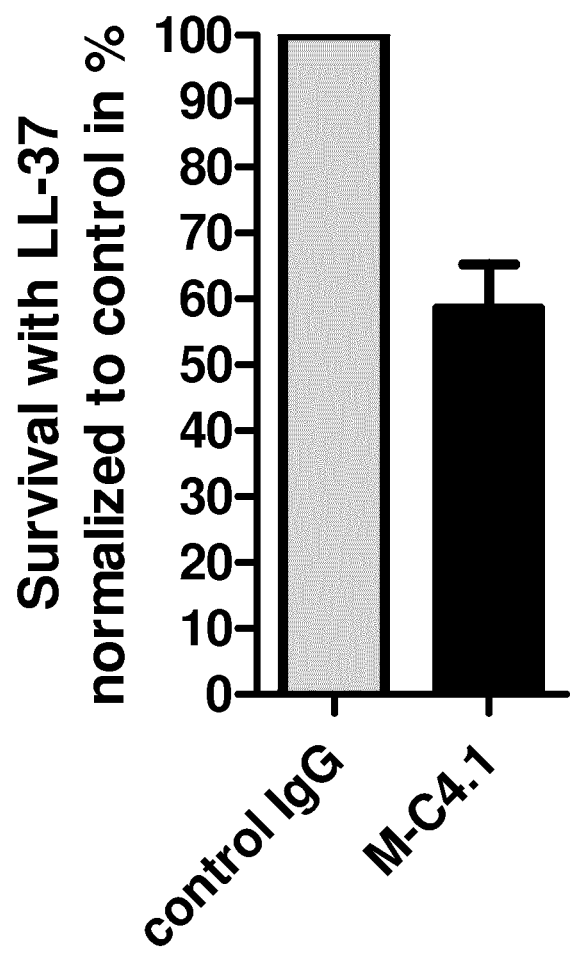

FIG. 9: Killing of *Staphylococcus aureus* by LL-37 was analyzed in the presence and absence of the MprF antibody M-C4.1. An anti-lysozyme antibody was used as a negative control. M-C4.1 increased the sensitivity of *Staphylococcus aureus* towards LL-37.

Figure 10:
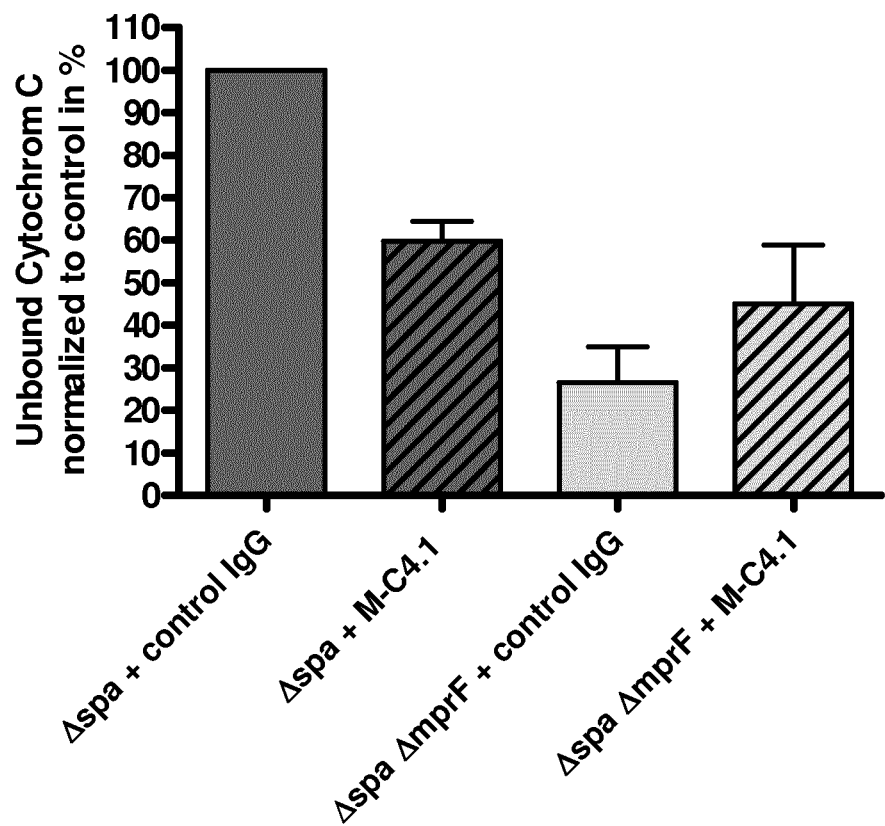

FIG. 10: The repulsion of positively charged cytochrome C was analyzed in the presence and absence of the MprF antibody M-C4.1. Pre-incubation of M-C4.1 with *S. aureus* SA113 Δspa led to 40% decreased repulsion of cytochrome C, compared to pre-incubation with anti-lysozyme antibodies, indicating that M-C4.1 impairs the flippase reaction of MprF. The *S. aureus* SA113 spa-mprF double deletion mutant treated with either M-C4.1 or anti-lysozyme served as negative controls and were significantly impaired in their capacity to repulse cytochrome C (55-75% reduced repulsion).

Figure 11:
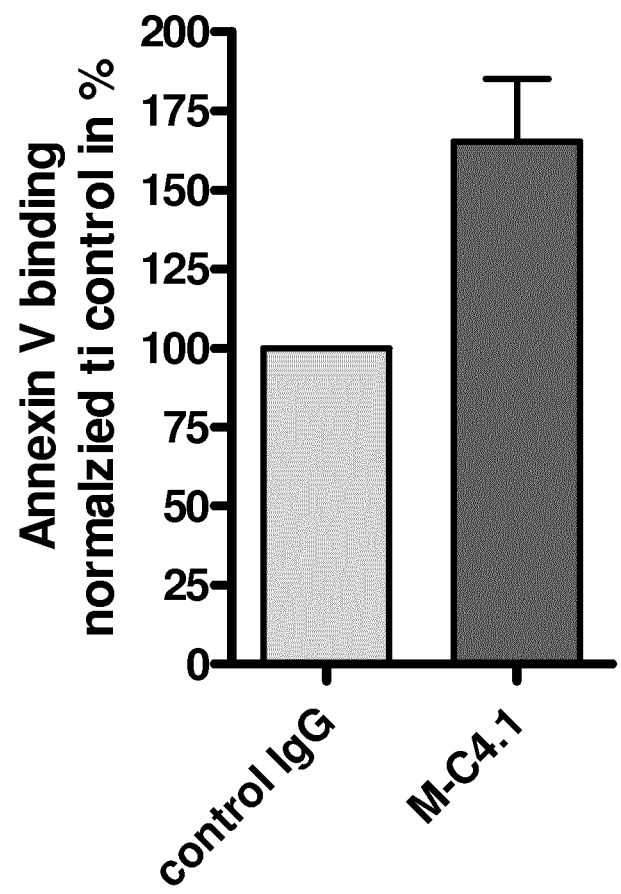

FIG. 11: Positively charged Annexin V binding to *S. aureus* was analyzed in the presence and absence of the MprF antibody M-C4.1. Cells were grown in the presence of M-C4.1 or anti-lysozyme antibody and then treated with annexin V. Cells pre-treated with M-C4.1 bound significantly more annexin V (70% increased binding) indicating that the pre-treatment with M-C4.1 had led to impaired flipping of lysyl-phosphatidylglycerol to the outer leaflet of the membrane.

FIGS. 12A and 12B: Sequence alignment of polypeptide sequences of MprF variants from specific *S. aureus* strains (MRSA252, SEQ ID NO.:114; MSSA479, SEQ ID NO.: 115; MW2, SEQ ID NO.:116; N315, SEQ ID NO.:117, NCTC8325, SEQ ID NO.:1 and USA300, SEQ ID NO.: 118). Extracellular loops 1-6 are underlined and bold.

Figure 13:
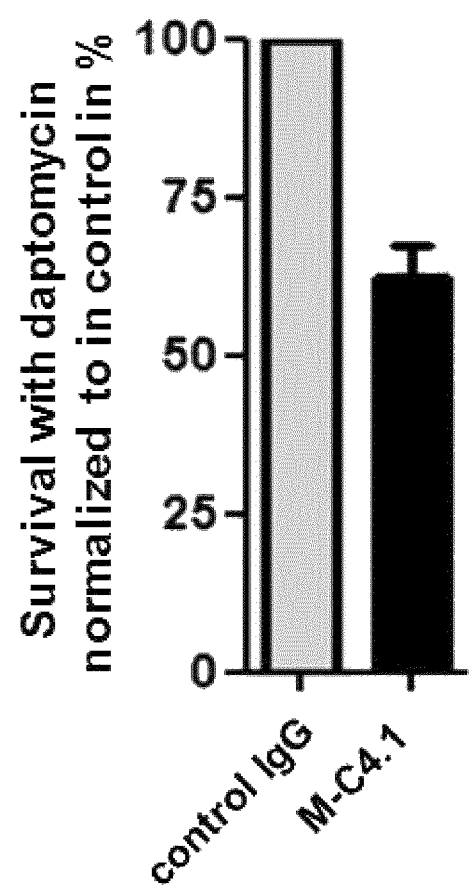

FIG. 13: Killing of *Staphylococcus aureus* clinical isolate 703 by daptomycin was analyzed in the presence and absence of the MprF antibody M-C4.1. An anti-lysozyme antibody was used as a negative control. While in the presence of the anti-lysozyme antibody, daptomycin had no effect on *S. aureus* 703, the application of the MprF specific antibody M-C4.1 restored susceptibility of *S. aureus* 703 bacteria to daptomycin and bacterial killing was induced.

Figure 14:
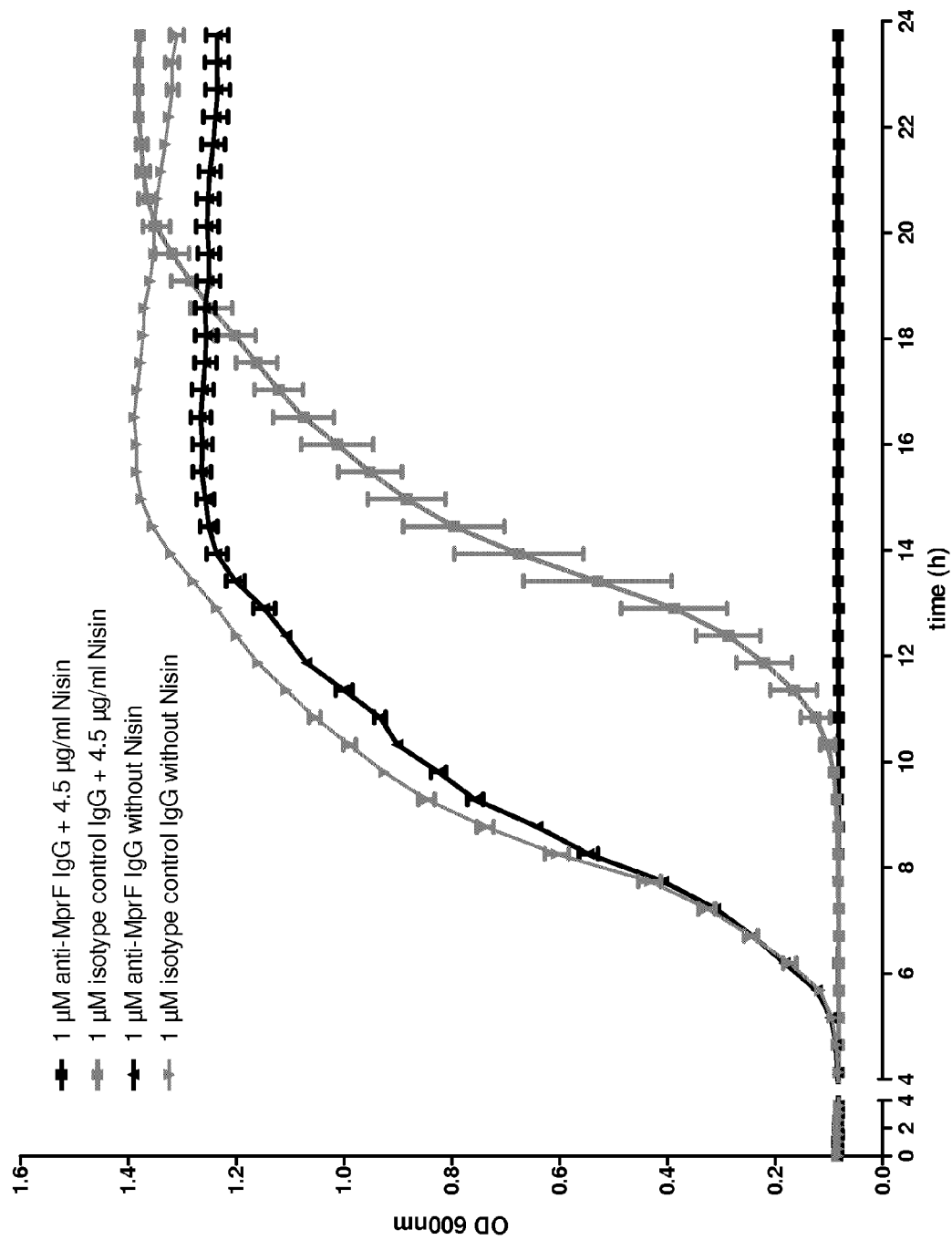

FIG. 14: Killing of *Staphylococcus aureus* by nisin was analyzed in the presence and absence of MprF antibodies. An anti-lysozyme antibody was used as a negative control. Antibodies of the present invention increased the sensitivity of the clinical isolate *Staphylococcus aureus* strain USA300 towards nisin.

Figure 15:
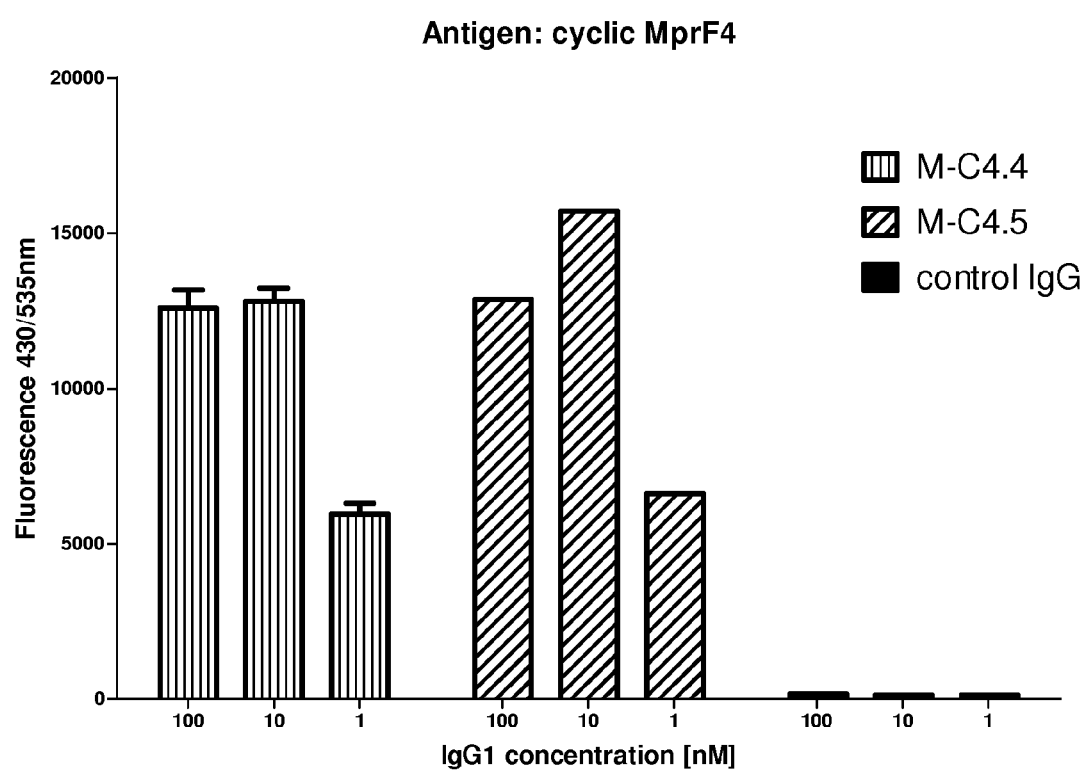

FIG. 15: Specific binding of selected IgGs on linear or cyclic peptide was analyzed by ELISA according to Example 3. Respective biotinylated cyclic peptide representing loop 4 was incubated with IgGs (M-C4.4, M-C4.5) in PBS. Both antibodies were shown to specifically bind to cyclic loop 4 peptide in a dose-dependent manner.

Figure 16:
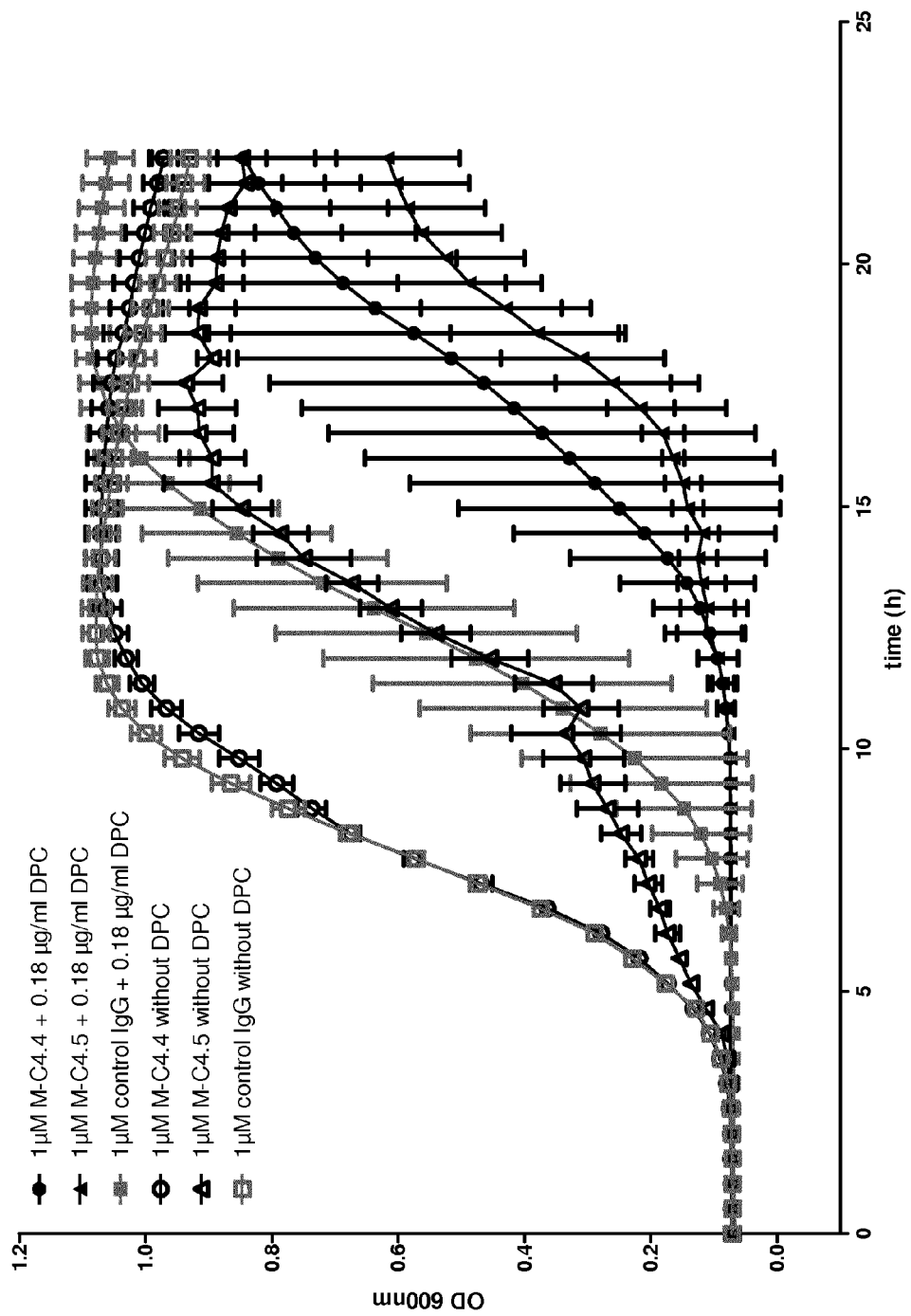

FIG. 16: Killing of *Staphylococcus aureus* by daptomycin was analyzed in the presence and absence of MprF antibodies. An anti-lysozyme antibody was used as a negative control antibody. Antibodies of the present invention increased the sensitivity of the clinical isolate *Staphylococcus aureus* strain USA300 towards daptomycin.

DETAILED DESCRIPTION

The MprF protein of *Staphylococcus aureus* has a length of 840 amino acids. The amino acid sequence is shown in SEQ ID No.: 1.

SEQ ID NO.:1 (MprF of *Staphylococcus aureus*):

```
MNQEVKNKIFSILKITFATALFIFVAITLYRELSGINFKDTLVEFSKINR
MSLVLLFIGGGASLVILSMYDVILSRALKMDISLGKVLRVSYIINALNAI
VGFGGFIGAGVRAMVYKNYTHDKKKLVHFISLILISMLTGLSLLSLLIVF
HVFDASLILDKITWVRWVLYVVSFFLPLFI1YSMVRPPDKNNRFVGLYCT
LVSCVEWLAAAVVLYFCGVIVDAHVSFMSFIAIFIIAALSGLVSFIPGGF
GAFDLVVLLGFKTLGVPEEKVLLMLLLYRFAYYFVPVIIALILSSFEFGT
SAKKYIEGSKYFIPAKDVTSFLMSYQKDIIAKIPSLSLAILVFFTSMIFF
VNNLTIVYDALYDGNHLTYYILLAIHTSACLLLLLNVVGIYKQSRRAIIF
AMISILLITVATFFTYASYILITWLAIIFVLLIVAFRRARRLKRPVRMRN
IVAMLLFSLFILYVNHIFIAGTLYALDIYTIEMHTSVLRYYFWLTILIIA
IIIGMIAWLFDYQFSKVRISSKIEDCEEIINQYGGNYLSHLIYSGDKQFF
TNENKTAFLMYRYKASSLVVLGDPLGDENAFDELLEAFYNYAEYLGYDVI
FYQVTDQHMPLYHNFGNQFFKLGEEAIIDLTQFSTSGKKRRGFRATLNKF
DELNISFEIIEPPFSTEFINELQHVSDLWLDNRQEMHFSVGEFNEEYLSK
APIGVMRNEENEVIAFCSLMPTYFNDAISVDLIRWLPELDLPLMDGLYLH
MLLWSKEQGYTKFNMGMATLSNVGQLHYSYLRERLAGRVFEHFNGLYRFQ
GLRRYKSKYNPNWEPRFLVYRKDNSLWESLSKVMRVIRHK
```

The membrane topology of MprF protein of *Staphylococcus aureus* is shown in FIG. 1. The extracellular loops of MprF are characterized by the following sequences:

TABLE 1

| Loop 1 | ELSGINFKDTLVEFSKINR | (SEQ ID NO.: 2) |
|---|---|---|
| Loop 2 | YKNYTHDKKKLVHF | (SEQ ID NO.: 3) |
| Loop 3 | SMVRPPDKNNRFVG | (SEQ ID NO.: 4) |
| Loop 4 | LGFKTLGVPEEKV | (SEQ ID NO.: 5) |
| Loop 5 | DALYDGNHLT | (SEQ ID NO.: 6) |
| Loop 6 | DIYTIEMHTSVLR | (SEQ ID NO.: 7) |

Accordingly, in one aspect the disclosure pertains to an antibody or antibody fragment specific for a polypeptide comprising SEQ ID NO.: 1, or an orthologue thereof. In another embodiment said antibody or antibody fragment is specific for MprF, or an orthologue thereof. In one embodiment the disclosure pertains to an antibody or antibody fragment specific for a polypeptide comprising SEQ ID NO.: 1, or an orthologue thereof wherein said antibody or antibody fragment increases the susceptibility of a pathogen to a cationic antimicrobial peptide. In one embodiment the antibody or antibody fragment is specific for a polypeptide comprising SEQ ID NO.: 1 or an orthologue thereof, induces the susceptibility of a pathogen to a cationic antimicrobial peptide.

In another aspect the disclosure pertains to an antibody or antibody fragment specific for a polypeptide comprising SEQ ID NO.: 1, or an orthologue thereof, wherein said antibody or antibody fragment inhibits the flippase activity of a polypeptide comprising SEQ ID NO.: 1, or an orthologue thereof. In one embodiment the disclosure pertains to an antibody or antibody fragment specific for MprF, or an orthologue thereof, wherein said antibody or antibody fragment inhibits the flippase activity of MprF. In another embodiment said antibody or antibody fragment inhibits the flippase activity of MprF and decreases the repulsion of cytochrome C from the membrane of bacteria. In another embodiment the repulsion of cytochrome C from the membrane of bacteria is decreased by at least 30%, at least 35%, at least 40%, at least 45%, at least 50%, at least 55%, at least 60%, at least 65%, at least 70%, at least 75%, at least 80%, at least 85% or at least 90%. In another embodiment the repulsion of cytochrome C from the membrane of bacteria is decreased by at least 30%, at least 35%, at least 40%, at least 45%, at least 50%, at least 55%, at least 60%, at least 65%, at least 70%, at least 75%, at least 80%, at least 85%, at least 90% in comparison to a control antibody. In another embodiment the repulsion of cytochrome C from the membrane of bacteria is decreased by at least 30%, at least 35%, at least 40%, at least 45%, at least 50%, at least 55%, at least 60%, at least 65%, at least 70%, at least 75%, at least 80%, at least 85%, at least 90% in an cytochrome C repulsion assay as described in Example 8. In a further embodiment the bacteria is *S. aureus*. In a further embodiment the bacteria is *S. aureus* SA113 Δspa.

In another embodiment said antibody or antibody fragment inhibits the flippase activity of MprF and increases the binding of annexin V to the membrane of bacteria. In another embodiment the binding of annexin V to the membrane of bacteria is increased by at least 30%, at least 35%, at least 40%, at least 45%, at least 50%, at least 55%, at least 60%, at least 65%, at least 70%, at least 75%, at least 80%, at least 85% or at least 90%. In another embodiment the binding of annexin V to the membrane of bacteria is increased by at least 30%, at least 35%, at least 40%, at least 45%, at least 50%, at least 55%, at least 60%, at least 65%, at least 70%, at least 75%, at least 80%, at least 85%, at least 90% in comparison to a control antibody. In another embodiment the binding of annexin V to the membrane of bacteria is increased by at least 30%, at least 35%, at least 40%, at least 45%, at least 50%, at least 55%, at least 60%, at least 65%, at least 70%, at least 75%, at least 80%, at least 85%, at least 90% in an annexin V binding assay as described in Example 8. In a further embodiment the bacteria is *S. aureus*. In a further embodiment the bacteria is *S. aureus* SA113 Δspa.

In another aspect, the disclosure pertains to an antibody or antibody fragment specific for a polypeptide comprising SEQ ID NO.: 1, or an orthologue thereof, wherein said antibody or antibody fragment binds to a polypeptide comprising SEQ ID NO.: 1, or an orthologue thereof, with a dissociation constant (KD) of less than $1 \times 10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$ or $10^{13}$ M$^{-1}$.

In one aspect, the disclosure pertains to an antibody or antibody fragment specific for a polypeptide comprising SEQ ID NO.: 1. In another aspect, the disclosure pertains to an antibody or antibody fragment specific for a polypeptide comprising SEQ ID NO.: 1, or an orthologue thereof, wherein said antibody or antibody fragment is an isolated antibody or antibody fragment. In one embodiment said antibody or antibody fragment is a monoclonal or polyclonal. In one embodiment said antibody or antibody fragment is human or humanized. In one embodiment said antibody or an antibody fragment is a chimeric antibody or antibody fragment. In one embodiment said antibody or antibody fragment comprises a human heavy chain constant region and a human light chain constant region. In one embodiment said antibody or antibody fragment is an IgG isotype. In another embodiment the antibodies can be of any isotype (e.g., IgG, IgE, IgM, IgD, and IgA), class (e.g., IgG1, IgG2, IgG3, IgG4, IgA1 and IgA2) or derivative thereof (e.g. IgG1 LALA). In one embodiment the antibodies are of IgG1 LALA isotype. In one embodiment said antibody fragment is an antigen binding fragment. In another embodiment said antibody or antibody fragment or antigen binding fragment is selected from the group consisting of a Fab, F(ab2)', F(ab)2' and scFV. In one embodiment the antibody is selected from the group consisting of a monoclonal antibody, a polyclonal antibody, a chimeric antibody, a humanized antibody, and a synthetic antibody. In one embodiment, the antibody or antibody fragment is a human or humanized antibody. In another embodiment, the antibody or antibody fragment is a human or humanized monoclonal antibody.

In one embodiment, the antibody or antibody fragment is a single chain antibody. In one embodiment, the antibody or antibody fragment is bispecific. In one embodiment the antibody or antibody fragment is a bispecific antibody-derived scaffold wherein said bispecific antibody-derived scaffold is selected from the group consisting of a bispecific-scFv, a tetravalent bispecific antibody, a cross-linked Fab or a bispecific IgG.

In one aspect, the disclosure pertains to an antibody or antibody fragment, wherein the antibody or antibody fragment is selected from the group consisting of single domain antibodies, maxibodies, minibodies, intrabodies, diabodies, triabodies, tetrabodies, v-NAR, camelid antibodies, ankyrins, domain antibodies, lipocalins, small modular immuno-pharmaceuticals, maxybodies, Protein A and affilins.

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to cationic antimicrobial peptides. In one embodiment the susceptibility of a gram-positive bacterium to cationic antimicrobial peptides is induced. In another embodiment the susceptibility of a gram-positive bacterium to cationic antimicrobial peptides is enhanced. In a preferred embodiment the gram-positive bacterium is *Staphylococcus aureus*.

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to a cationic antimicrobial peptide and wherein said cationic antimicrobial peptide is a lipopeptide. In a preferred embodiment, the lipopeptide interacts with membranes via their lipid tails. In a more preferred embodiment, the lipopeptide has an antimicrobial activity. In a preferred embodiment said lipopeptide is a cationic amphiphilic peptide with an acetylated N-terminus. In another embodiment said acylated N-terminus comprises a chain of at least 8 fatty acids, at least 9 fatty acids, at least 10 fatty acids, at least 11 fatty acids, at least 12 fatty acids, at least 13 fatty acids, at least 14 fatty acids, at least 15 fatty acids, at least 16 fatty acids, at least 17 fatty acids, at least 18 fatty acids.

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to a cationic antimicrobial peptide and wherein said cationic antimicrobial peptide is a lipopeptide which is a member of the polymyxin family.

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to a cationic antimicrobial peptide and wherein said cationic antimicrobial peptide is an amphipathic antimicrobial peptide. In another embodiment the cationic antimicrobial peptide is an alpha-helical or beta-helical peptide. In a further embodiment the cationic antimicrobial peptide is a cathelicidin. In one embodiment the cathelicidin is LL-37.

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to an antimicrobial peptide and wherein said antimicrobial peptide is a lipopeptide and wherein said lipopeptide is a cyclic lipopeptide. In a preferred embodiment said cyclic lipopeptide is a daptomycin-related lipopeptide. In a more preferred embodiment said daptomycin-related lipopeptide is A54145 or an A-21978C cyclic peptide in which the n-decanoyl fatty acid side chain of daptomycin is replaced by an n-heptanoyl, n-octanoyl, n-nonanoyl, n-undecanoyl, n-lauroyl, n-dodecanoyl, n-tridecanoyl, n-myristoyl, n-pentadecanoyl, 8-methyldecanoyl, 10-methylundecanoyl, 10-methyldodecanoyl or n-tetradecanoyl fatty. In a more preferred embodiment, the cyclic lipopeptide is daptomycin (LY 146032).

In another aspect the disclosure pertains to an antibody or antibody fragment specific for a polypeptide comprising SEQ ID NO.: 1 or an orthologue thereof, wherein said antibody or antibody fragment increases the susceptibility of a gram-positive bacterium to an antimicrobial peptide and wherein said antimicrobial peptide is a lantiobiotic. In another embodiment said lantibiotic is nisin.

In another aspect the disclosure pertains to an antibody or antibody fragment specific for a polypeptide comprising SEQ ID NO.: 1 or an orthologue thereof, wherein said antibody or antibody fragment binds to an extracellular loop of MprF. In one embodiment said antibody or antibody fragment binds to an extracellular loop of MprF wherein said loop comprises an amino acid sequence of ELSGINFKDTLVEFSKINR (SEQ ID NO.: 2), YKNYTHDKKKLVHF (SEQ ID NO.: 3), SMVRPPDKNNRFVG (SEQ ID NO.: 4), LGFKTLGVPEEKV (SEQ ID NO.: 5), DALYDGNHLT (SEQ ID NO.: 6) or DIYTIEMHTSVLR (SEQ ID NO.: 7). In one embodiment said antibody or antibody fragment binds to an extracellular loop of MprF wherein said loop comprises the amino acid sequence ELSGINFKDTLVEFSKINR (SEQ ID NO.: 2). In one embodiment said antibody or antibody fragment binds to an extracellular loop of MprF wherein said loop comprises the amino acid sequence DALYDGNHLT (SEQ ID NO.: 6). In one embodiment said antibody or antibody fragment binds to an extracellular loop of MprF wherein said loop comprises the amino acid sequence DIYTIEMHTSVLR (SEQ ID NO.: 7). In a more preferred embodiment said antibody or antibody fragment binds to an extracellular loop of MprF wherein said loop comprises the amino acid sequence LGFKTL-GVPEEKV (SEQ ID NO.: 5).

In another aspect the disclosure pertains to an antibody or antibody fragment specific for a polypeptide comprising ELSGINFKDTLVEFSKINR (SEQ ID NO.: 2), YKNYTH-DKKKLVHF (SEQ ID NO.: 3), SMVRPPDKNNRFVG (SEQ ID NO.: 4), LGFKTLGVPEEKV (SEQ ID NO.: 5), DALYDGNHLT (SEQ ID NO.: 6) or DIYTIEMHTSVLR (SEQ ID NO.: 7). In one embodiment the peptides are isolated polypeptides peptides. In another aspect the disclosure pertains to an antibody or antibody fragment specific for one of the peptides of ELSGINFKDTLVEFSKINR (SEQ ID NO.: 2), YKNYTHDKKKLVHF (SEQ ID NO.: 3), SMVRPPDKNNRFVG (SEQ ID NO.: 4), LGFKTL-GVPEEKV (SEQ ID NO.: 5), DALYDGNHLT (SEQ ID NO.: 6) or DIYTIEMHTSVLR (SEQ ID NO.: 7). In one embodiment the peptides are isolated peptides.

In another aspect the disclosure pertains to an antibody or antibody fragment specific for a polypeptide comprising CELSGINFKDTLVEFSKINR (SEQ ID NO.: 108), CYKNYTHDKKKLVHF (SEQ ID NO.: 109), CSMVRPP-DKNNRFVG (SEQ ID NO.: 110), CGLGFKTLGVPEEKV (SEQ ID NO.: 111), CGGDALYDGNHLT (SEQ ID NO.: 112) or CDIYTIEMHTSVLR (SEQ ID NO.: 113). In one embodiment the peptides are isolated polypeptides peptides. In another aspect the disclosure pertains to an antibody or antibody fragment specific for one of the peptides of CELS-GINFKDTLVEFSKINR (SEQ ID NO.: 108), CYKNYTH-DKKKLVHF (SEQ ID NO.: 109), CSMVRPPDKNNRFVG (SEQ ID NO.: 110), CGLGFKTLGVPEEKV (SEQ ID NO.: 111), CGGDALYDGNHLT (SEQ ID NO.: 112) or CDIYTI-EMHTSVLR (SEQ ID NO.: 113). In one embodiment the peptides are isolated peptides. In another embodiment the peptides are linear peptides. In a further embodiment the peptides are cyclic peptides.

In another aspect the disclosure pertains to a kit comprising an antibody or antibody fragment specific for a polypeptide comprising SEQ ID NO.: 1, or an orthologue thereof, and a cationic antimicrobial peptide. In another aspect the disclosure pertains to a kit comprising an antibody or antibody fragment specific for a polypeptide comprising SEQ ID NO.: 1, or an orthologue thereof, wherein said antibody or antibody fragment increases the susceptibility of a pathogen to a cationic antimicrobial peptide and a cationic antimicrobial peptide. In one embodiment the disclosure pertains to a kit comprising an antibody or antibody fragment specific for a polypeptide comprising ELSGIN-FKDTLVEFSKINR (SEQ ID NO.: 2), YKNYTHDKK-KLVHF (SEQ ID NO.: 3), SMVRPPDKNNRFVG (SEQ ID NO.: 4), LGFKTLGVPEEKV (SEQ ID NO.: 5), DALY-DGNHLT (SEQ ID NO.: 6) or DIYTIEMHTSVLR (SEQ ID NO.: 7) and a cationic antimicrobial peptide. In one embodiment the disclosure pertains to a kit comprising an antibody or antibody fragment specific for one of peptides of ELS-GINFKDTLVEFSKINR (SEQ ID NO.: 2), YKNYTHDK-KKLVHF (SEQ ID NO.: 3), SMVRPPDKNNRFVG (SEQ ID NO.: 4), LGFKTLGVPEEKV (SEQ ID NO.: 5), DALY-DGNHLT (SEQ ID NO.: 6) or DIYTIEMHTSVLR (SEQ ID NO.: 7) and a cationic antimicrobial peptide. In one embodiment the disclosure pertains to a kit comprising an antibody or antibody fragment specific for one of peptides of CELS-GINFKDTLVEFSKINR (SEQ ID NO.: 108), CYKNYTH-DKKKLVHF (SEQ ID NO.: 109), CSMVRPPDKNNRFVG (SEQ ID NO.: 110), CGLGFKTLGVPEEKV (SEQ ID NO.: 111), CGGDALYDGNHLT (SEQ ID NO.: 112) or CDIYTI-EMHTSVLR (SEQ ID NO.: 113).

In another aspect the disclosure pertains to an antibody or antibody fragment specific for a polypeptide comprising SEQ ID NO.: 1, or an orthologue thereof, for use in medicine wherein said antibody or antibody fragment increases the susceptibility of a pathogen to a cationic antimicrobial peptide. In one embodiment the disclosure pertains to the use of an antibody or antibody fragment specific for a polypeptide comprising SEQ ID NO.: 1, or an orthologue thereof, in the treatment of an infectious disease, wherein said antibody or antibody fragment increases the susceptibility of a pathogen to a cationic antimicrobial peptide. In another embodiment the infectious diseases is an infection with gram-positive or gram-negative bacteria. In a preferred embodiment said infectious disease is an infection with *Staphylococcus aureus*. In another aspect the disclosure pertains to a pharmaceutical composition comprising an antibody or antibody fragment specific for a polypeptide comprising SEQ ID NO.: 1, or an orthologue thereof, for use in medicine wherein said antibody or antibody fragment increases the susceptibility of a pathogen to a cationic antimicrobial peptide.

In another aspect the disclosure pertains to a combination comprising an antibody or antibody fragment specific for a polypeptides comprising SEQ ID NO.: 1, or an orthologue thereof, and a cationic antimicrobial peptide for use in medicine. In another aspect the disclosure pertains to a synergistic combination comprising an antibody or antibody fragment specific for a polypeptide comprising SEQ ID NO.: 1, or an orthologue thereof, and a cationic antimicrobial peptide for use in medicine. In one embodiment the combination is used in the treatment of an infectious disease. In one embodiment the combination is used in the treatment of an infectious disease with gram-positive or gram-negative bacteria. In a preferred embodiment said infectious disease is an infection with *Staphylococcus aureus*. In another embodiment the combination is used in the treatment of an infectious disease with antibiotic resistant bacteria. In another embodiment said antibiotic resistant bacteria is resistant to beta-lactam antibiotics. In another embodiment said antibiotic resistant bacteria is a Methicillin-resistant *Staphylococcus aureus*.

In another aspect the disclosure pertains to a pharmaceutical composition comprising an antibody or antibody fragment specific for a polypeptides comprising SEQ ID NO.: 1, or an orthologue thereof, and a cationic antimicrobial peptide for use in medicine.

In another aspect the disclosure pertains to a method of treating a bacterial infection in an individual in need thereof, which method comprises administration of an antibody or antibody fragment specific for a polypeptides comprising SEQ ID NO.: 1, or an orthologue thereof. In another embodiment the disclosure pertains to a method of treating a bacterial infection in an individual in need thereof, which method comprises administration of an antibody or antibody fragment specific for a polypeptides comprising SEQ ID NO.: 1, or an orthologue thereof and a cationic antimicrobial peptide. In another embodiment the disclosure pertains to a method of treating a bacterial infection in an individual in need thereof, which method comprises administration of a pharmaceutical composition comprising an antibody or antibody fragment specific for a polypeptides comprising SEQ ID NO.: 1, or an orthologue thereof and a cationic antimicrobial peptide.

In certain aspects of the present invention the antibody of the synergistic combination of the present invention is an antibody specific for a polypeptides comprising SEQ ID NO.: 1. In other aspects the antibody of the synergistic combination of the present invention is an antibody specific for a peptide of SEQ ID NO.: 2, an antibody specific for a peptide of SEQ ID NO.: 3, an antibody specific for a peptide of SEQ ID NO.: 4, an antibody specific for a peptide of SEQ ID NO.: 5, an antibody specific for a peptide of SEQ ID NO.: 6, or an antibody specific for a peptide of SEQ ID NO.: 7. In most preferred aspects, the antibody of the synergistic combination of the present invention is an antibody specific for a peptide consisting of any one of SEQ ID NO's: 5, 6 or 7.

In another aspect the disclosure pertains to an antibody or antibody fragment specific for a polypeptide comprising SEQ ID NO.: 1 or an orthologue thereof, wherein said antibody or antibody fragment increases bacterial killing of at least 25%, at least 30%, at least 35%, at least 40%, at least 45%, at least 50%, at least 55%, at least 60%, at least 65%, at least 70%, at least 75%, at least 80%, at least 85%, at least 90%, at least 95% in the presence of a cationic antimicrobial peptide.

In another aspect the disclosure pertains to an antibody or antibody fragment specific for a polypeptide comprising SEQ ID NO.: 1 or an orthologue thereof, wherein said antibody or antibody fragment increases bacterial killing of at least 25%, at least 30%, at least 35%, at least 40%, at least 45%, at least 50%, at least 55%, at least 60%, at least 65%, at least 70%, at least 75%, at least 80%, at least 85%, at least 90%, at least 95% in the presence of a cationic antimicrobial peptide in an experimental setting as described in Example 5, Example 6 or Example 7 of the present disclosure.

In other aspects of the present invention the antibodies of the present invention are specific for an orthologue of the polypeptides of SEQ ID NO.:1. MprF homologues can be found in most bacterial kingdoms and antibodies against these orthologues are contemplated in the present invention. In certain embodiments the orthologues have a sequence identity of at least 75%, at least 80%, at least 85%, at least 90%, at least 95%, at least 96%, at least 97%, at least 98%, at least 99% to the polypeptides of SEQ ID NO.:1.

In another aspect the disclosure pertains to an antibody or antibody fragment specific for a polypeptide comprising SEQ ID NO.: 1 or an orthologue thereof, comprising 6 CDRs defined by Kabat of any of the antibodies in Table 3.

In another aspect the disclosure pertains to an antibody or antibody fragment specific for a polypeptide comprising SEQ ID NO.: 1 or an orthologue thereof, that cross-competes with an antibody described in Table 3.

In a certain embodiment, the antibody that cross-competes with an antibody described in Table 3 reduces the binding of one of the antibodies described in Table 3 to a polypeptide comprising SEQ ID NO.: 1 or an orthologue thereof, by at least 50%, 60%, 70%, 80% or 90% in an ELISA-based cross-competition assay.

In a certain embodiment, the antibody that cross-competes with an antibody described in Table 3 reduces the binding of one of the antibodies described in Table 3 to a polypeptide comprising SEQ ID NO.: 1 or an orthologue thereof, by at least 50%, 60%, 70%, 80% or 90% in an ELISA-based cross-competition assay according to Example 9 in comparison to the positive control.

In a certain embodiment, the antibody that cross-competes with an antibody described in Table 3 reduces the binding of one of the antibodies described in Table 3 to one of the peptides of ELSGINFKDTLVEFSKINR (SEQ ID NO.: 2), YKNYTHDKKKLVHF (SEQ ID NO.: 3), SMVRPPDKNNRFVG (SEQ ID NO.: 4), LGFKTLGVPEEKV (SEQ ID NO.: 5), DALYDGNHLT (SEQ ID NO.: 6) or DIYTIEMHTSVLR (SEQ ID NO.: 7) by at least 50%, 60%, 70%, 80% or 90% in an ELISA-based cross-competition assay.

In a certain embodiment, the antibody that cross-competes with an antibody described in Table 3 reduces the binding of one of the antibodies described in Table 3 to one of peptides of ELSGINFKDTLVEFSKINR (SEQ ID NO.: 2), YKNYTHDKKKLVHF (SEQ ID NO.: 3), SMVRPPDKNNRFVG (SEQ ID NO.: 4), LGFKTLGVPEEKV (SEQ ID NO.: 5), DALYDGNHLT (SEQ ID NO.: 6) or DIYTIEMHTSVLR (SEQ ID NO.: 7) by at least 50%, 60%, 70%, 80% or 90% in an ELISA-based cross-competition assay according to Example 9 in comparison to the positive control.

In another aspect, the disclosure pertains to an antibody or fragment thereof specific for a polypeptide comprising SEQ ID NO.: 1 or an orthologue thereof, and interacts with (e.g., by binding, stabilizing, spatial distribution) the same epitope as an antibody described in Table 3.

In a certain embodiment, the antibody or fragment thereof specific for a polypeptide comprising SEQ ID NO.: 1 or an orthologue thereof, binds to the same epitope as an antibody described in Table 3, wherein said epitope is an extracellular loop of MprF. In a certain embodiment, the antibody or fragment thereof specific for a polypeptide comprising SEQ ID NO.: 1 or an orthologue thereof, binds to the same epitope as an antibody described in Table 3, wherein said epitope is an extracellular loop of MprF and wherein said extracellular loop comprises an amino acid sequence of ELSGINFKDTLVEFSKINR (SEQ ID NO.: 2), YKNYTHDKKKLVHF (SEQ ID NO.: 3), SMVRPPDKNNRFVG (SEQ ID NO.: 4), LGFKTLGVPEEKV (SEQ ID NO.: 5), DALYDGNHLT (SEQ ID NO.: 6) or DIYTIEMHTSVLR (SEQ ID NO.: 7). In another embodiment said antibody or fragment thereof is a human monoclonal antibody. Such human monoclonal antibodies can be prepared and isolated as described herein.

Definitions

The term "antibody" as used herein includes whole antibodies. A naturally occurring "antibody" is a protein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised specific CH domains (e.g. CH1, CH2 and CH3). Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g. IgG1 LALA). The antibodies can be of any species, chimeric, humanized or human.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3" antibody fragment Antigen binding can be performed by "fragments" or "antigen binding fragments" of an intact antibody. Herein, both terms are used interchangeably. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) Nature 341:544-546), which consists of a VH domain; and an isolated complementary determining region (CDR).

A "single chain Fragment (scFv)" is a single protein chain in which the VL and VH regions pair to form monovalent molecules (known as single chain Fv (scFv); see, e.g., Bird et al., (1988) Science 242:423-426; and Huston et al., (1988) Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "epitope" includes any proteinaceous region which is specifically recognized by an immunoglobulin or T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

The term "cross-competes" refers to antigen binding moieties (such as antibodies) which share the ability to bind to a specific region of an antigen. In the present disclosure an antigen binding moiety that is "cross-competitive" has the ability to interfere with the binding of another antigen binding moiety for MprF in a standard competitive binding assay. Such an antibody may, according to non-limiting theory, bind to the same or a related or nearby (e.g., a structurally similar or spatially proximal) epitope on MprF or an extracellular loop of MprF as the antibody with which it competes. Cross-competition studies to find antibodies that competitively bind with one another, e.g., the antibodies compete for binding to the antigen can be performed. For example the present disclosure provides antibodies that cross-compete with (e.g., by binding, stabilizing, spatial distribution) the antibodies described in Table 3. The ability or extent to which an antibody or other binding agent is able to interfere with the binding of another antibody or binding molecule to MprF or an extracellular loop of MprF and therefore whether it can be said to cross-compete according to the invention, can be determined using standard competition binding assays. Cross-competition is present if antibody A reduces binding of antibody B at least by 50%, at least by 60%, specifically at least by 70% and more specifically at least by 80% and vice versa in comparison to the positive control which lacks one of said antibodies. As the skilled artisan appreciates competition may be assessed in different assay set-ups. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competition uses an ELISA-based approach (e.g. Example 9). Furthermore, a high throughput process for "binning" antibodies based upon their cross-competition is described in International Patent Application No. WO2003/48731. Cross-competition is present if the antibody under investigation reduces the binding of one of the antibodies described in Table 3 by 60% or more, specifically by 70% or more and more specifically by 80% or more and if one of the antibodies described in Table 3 reduces the binding of said antibody to MprF or an extracellular loop of MprF by 60% or more, specifically by 70% or more and more specifically by 80% or more.

The term "human antibody", as used herein, is intended to include antibodies having variable regions in which both the framework and CDR regions are derived from sequences of human origin. As used herein, a human antibody comprises heavy or light chain variable regions or full length heavy or light chains. In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Thereby said human antibody can be obtained from technology platforms which comprise antibodies derived from human germline genes either generated by PCR-amplification of VH/VL repertoire isolated from B-cells or are generated synthetically. Technology platforms include library based approaches comprising human immunoglobulin genes displayed on phage, ribosome or yeast. Respective display technologies are standard in the scientific community. Furthermore immunization of a transgenic mouse carrying human immunoglobulin repertoire is another approach to generate human antibodies against an antigen of interest. Antibodies or fragments thereof selected from an antibody library based on the MorphoSys HuCAL® concept (Knappik et al., (2000) J Mol Biol 296:57-86) are considered as fully human.

The terms "monoclonal antibody" as used herein refer to a preparation of antibody molecules of single molecular composition. A monoclonal antibody composition displays a unique binding site having a unique binding specificity and affinity for particular epitopes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al (1994) Proc. Natl. Acad. Sci. USA, 81:6851-6855; Morrison and Oi (1988) Adv. Immunol., 44:65-92; Verhoeyen et al. (1988) Science, 239:1534-1536; Padlan, Molec (1991) Immun., 28:489-498; and Padlan, Molec (1994) Immun., 31:169-217. Other examples of human engineering technology include, but are not limited to Xoma technology disclosed in U.S. Pat. No. 5,766,886.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "isolated" refers to a compound which can be e.g. an antibody or an antigen binding moiety that is substantially free of other antibodies or antigen binding moieties having different antigenic specificities. Moreover, an isolated antibody antigen binding moiety may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. For example IgG1 LALA is a modified version of the IgG isotype having significantly reduced effector functions. Specific substitutions of amino acids reduced the binding affinity for Fc gamma RI receptor as compared with unmodified antibody. IgG1 LALA is described in U.S. Ser. No. 08/479,752 (SCOTGEN BIOPHARMACEUTICALS INC.) which is incorporated by reference in its entirety. In certain embodiments of the present disclosure the antigen-binding moieties of are antibodies and are of the type IgG, IgM, IgA, IGE or IgD. In specific embodiments the antibodies are of the type IgG. In certain embodiments of the present disclosure the antibodies are of the subtype IgG1, IgG2, IgG3 or IgG4. In specific embodiments the antibodies are of the subtype IgG1 or IgG4. In other specific embodiments the antibodies are of the subtype IgG1 or IgG1 LALA.

The term "affinity" as used herein refers to the strength of interaction between an antigen binding moiety, like e.g. a monoclonal antibody and an antigen at single antigenic sites. Within each antigenic site, the variable region of the antibody "arm" interacts through weak non-covalent forces with antigen at numerous sites; the more interactions, the stronger the affinity.

The term "KD", as used herein, refers to the dissociation constant, which is obtained from the ratio of Kd to Ka (i.e. Kd/Ka) and is expressed as a molar concentration (M). KD values for antigen binding moieties like e.g. monoclonal antibodies can be determined using methods well established in the art. Methods for determining the KD of an antigen binding moiety like e.g. a monoclonal antibody are SET (soluble equilibrium titration) or surface plasmon resonance using a biosensor system such as a Biacore® system. Antibodies of the present disclosure typically have a dissociation rate constant (KD) (koff/kon) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10\text{-}10$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; and Rossolini et al. (1994) Mol. Cell. Probes 8:91-98).

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

"Synergy", "synergism" or "synergistic activity" mean more than the expected additive effect of a combination. The "synergy", "synergism" or "synergistic activity" of a combination can be determined by different methods of like e.g. Chou et al., Clarke et al., and/or Webb et al. See Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. See also Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety. See also Webb, J. L. (1963) Enzyme and Metabolic Inhibitors, Academic Press, New York, which is incorporated by reference in its entirety.

The term "orthologue" denotes a polypeptide or protein obtained from one species that is the functional counterpart of a polypeptide or protein from a different species. Sequence differences among orthologues are the result of speciation. "Orthologues" as used herein encompass polypeptides derived from another origin than the shown origin (SEQ ID NO: 1) which have substantially the same amino acid sequence and substantially the same biological activity as MprF set forth in SEQ ID NO: 1. "Orthologues" as used herein encompass MprF-orthologues derived from gram-negative or gram-positive bacteria. Representative MprF-orthologues are for example polypeptides (FIG. 12) encoded by SEQ ID NO.:114, SEQ ID NO.:115, SEQ ID NO.:116, SEQ ID NO.:117, SEQ ID NO.:118. Respective polypeptides are derived from the strains MSSA479 (a methicillin-sensitive strain, isolated from a patient in the community who developed severe invasive disease), N315 (isolated as an methicillin-resistant *S. aureus* that was a major pathogen causing hospital-acquired infections in 1982), MRSA252 (representative of the epidemic EMRSA-16 lineage endemic in UK hospitals), MW2 (methicillin resistant, community acquired) and USA300 (methicillin resistant, community acquired (CA-MRSA). USA300 was first identified in 1998, and is thought to be the primary causal strain of community-acquired Staph infections throughout the United States, Canada and Europe. In 2006 the CDC reported that 64% of MRSA isolated from infected patients were of the USA300 strain. USA300 causes an estimated 20 thousands deaths annually in the United States only. Further representative MprF-orthologues can be for example derived from the clinical isolate *Staphylococcus aureus* 703 (described in Jones et al., AAC 2008).

As used herein, the phrase "pathogen" means an agent which causes a disease state or affliction in an animal. Included within this definition, for examples, are bacteria (gram-negative or gram-positive bacteria), protozoans, fungi, viruses and metazoan parasites which either produce a disease state or render an animal infected with such an organism susceptible to a disease state (e.g., a secondary infection). Further included are species and strains of the genus *Staphylococcus* which produce disease states in animals. As used herein, the term "organism" means any living biological system, including viruses, regardless of whether it is a pathogenic agent.

The term "Gram-negative bacteria" as used herein refer to bacteria characterized by the presence of a double membrane surrounding each bacterial cell. Representative Gram-negative bacteria include *Acinetobacter calcoaceticus, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica* and *Yersinia pestis*.

The term "Gram-positive bacteria" as used herein refers to bacteria characterized by having a single membrane and teichoic acids or teichoic-like acids as part of their cell wall and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B streptococcus), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A streptococcus), *Streptococcus salivarius, Streptococcus sanguis*.

As used herein, the term "*Staphylococcus*" means any species or strain of bacteria which is members of the genus *Staphylococcus* regardless of whether they are known pathogenic agents.

As used herein, "bacteremia" means the presence of viable bacteria in the blood or organs of an individual (human or other animal). "Bacteremia caused by *S. aureus*" or "*S. aureus* bacteremia" refers to bacteremia in which at least some of the bacteria in the blood or organs are *S. aureus*. Other species of bacteria also may be present.

"Infection" as used herein is an invasion and multiplication of microorganisms in tissues of a subject's body. The infection or "infectious disease" may be clinically inapparent or result in local cellular injury due to competitive metabolism, toxins, intracellular replication, or antigen-antibody response. The infection may remain localized, subclinical and temporary if the body's defensive mechanisms are effective. A local invention may persist and spread by extension to become an acute, subacute, or chronic clinical infection or disease state. A local infection may also become systemic when the microorganisms gain access to the lymphatic or vascular system. Infectious diseases include bacterial, viral, parasitic, opportunistic, or fungal infections.

As used herein "antibiotic" refers to an aminoglycoside such as gentamycin or a beta-lactam such as penicillin, cephalosporin and the like. Also included are known anti-fungals and anti-virals.

The term "antimicrobial agent" as used herein refers to any entity with antimicrobial activity, i.e. the ability to inhibit the growth and/or kill bacterium, for example gram positive- and gram negative bacteria. An antimicrobial agent is any agent which results in inhibition of growth or reduction of viability of a bacteria by at least about 30% or at least about 40%, or at least about 50% or at least about 60% or at least about 70% or more than 70%, or any integer between 30% and 70% or more, as compared to in the absence of the antimicrobial agent. In one embodiment, an antimicrobial agent is an agent which specifically targets a bacteria cell. In another embodiment, an antimicrobial agent modifies (i.e. inhibits or activates or increases) a pathway which is specifically expressed in bacterial cells. An antimicrobial agent can include any chemical, peptide (i.e. an antimicrobial peptide), peptidomimetic, entity or moiety, or analogues of hybrids thereof, including without limitation synthetic and naturally occurring non-proteinaceous entities. In one embodiment an antimicrobial agent includes cationic antimicrobial peptides further including lipopeptides, cyclic lipopeptides and daptomycin-related lipopeptides and daptomycin.

The term "cationic antimicrobial peptide" or "CAMP" as used herein refers to polypeptides or peptides having lengths of 10-50 amino acids and affect the cytoplasmic membrane of bacteria by typically forming channels. According to the present disclosure and also according to the scientific community (see e.g. Mishra et al. 2001, Antimicrobial agents and chemotherapy) the term "cationic antimicrobial peptide" also includes "CAMP-like antibiotics" like e.g. daptomycin and daptomycin-related lipopeptides. Most cationic antimicrobial peptides have a net positive charge due an excess of basic lysine and arginine residues over acidic residues. Typically, their mode of action is to specifically bind to cell wall precursor lipid II or bind to bacterial membrane and other bacterial surfaces, and disrupt specific cellular processes such as cell wall and membrane biosynthesis, as well as DNA replication upon translocation. In one embodiment the cationic antimicrobial peptide is an amphipathic antimicrobial peptide. In another embodiment the cationic antimicrobial peptide is an alpha-helical or beta-helical peptide. In a further embodiment the cationic antimicrobial peptide is a cathelicidin. In one embodiment the cathelicidin is LL-37. In one embodiment the cationic antimicrobial peptide is a lantibiotic, like e.g. nisin. In one embodiment, the cationic antimicrobial peptide is a lipopeptide, and in some embodiments, the lipopeptide is a cyclic lipopeptide. In another embodiment, the cyclic lipopeptide is daptomycin or a daptomycin-related lipopeptide.

The term "CAMP-like antibiotics" as used herein refers to polypeptides acting as a CAMP, like e.g. daptomycin and daptomycin-related lipopeptides, such as e.g. friulimicin B.

The term "lipopeptide" refers to a molecule that comprises a lipid-like moiety covalently linked to a peptide moiety, as well as salts, esters, amides and ethers thereof. The term "lipopeptide" also encompasses protected forms of lipopeptide in which one or more amino, carboxylate or hydroxyl groups are protected (see, e.g., "Protective Groups in Organic Synthesis" by Theodora W. Greene, John Wiley and Sons, New York, 1981 for examples of protecting groups) and lipopeptides consisting of cationic amphiphilic peptides with an acetylated N-terminus (C8-C18 fatty acid chain length). Furthermore, members of the polymyxin family are included. In a preferred embodiment, the lipopeptide is a cyclic lipopeptide. In a preferred embodiment, the lipopeptide interacts with membranes via their lipid tails. In a more preferred embodiment, the lipopeptide has an antimicrobial activity.

The term "cyclic lipopeptide" as used in this specification means a lipopeptide having a polypeptide ring and, on said ring, a side-chain acyl-amino group, optionally with or without one or more other side chains. In a preferred embodiment, the cyclic lipopeptide is a daptomycin-related molecule.

The term "daptomycin-related lipopeptide" disclosed in the above-identified application relates to synthetic and semisynthetic lipopeptides in which the ornithine and/or kynurine residues, and/or the fatty acid side chain of daptomycin, are modified. A "daptomycin-related lipopeptide" includes, inter alia, daptomycin, A54145, a daptomycin-related lipopeptide disclosed in U.S. Pat. Nos. 4,537,717, 4,482,487, Re. 32,311, Re. 32,310, U.S. Pat. No. 5,912,226, currently in reissue as U.S. Ser. No. 09/547,357, U.S. Provisional Applications No. 60/170,943, 60/170,946 or 60/170,945, filed Dec. 15, 1999, U.S. Provisional Application No. 60/208,222, filed May 30, 2000, all of which are specifically incorporated herein by reference, or an A-21978C cyclic peptide in which the n-decanoyl fatty acid side chain of daptomycin is replaced by an n-heptanoyl, n-octanoyl, n-nonanoyl, n-undecanoyl, n-lauroyl, n-dodecanoyl, n-tridecanoyl, n-myristoyl, n-pentadecanoyl, 8-methyldecanoyl, 10-methylundecanoyl, 10-methyldodecanoyl or n-tetradecanoyl fatty. In a more preferred embodiment, the cyclic lipopeptide is daptomycin (LY 146032). The term daptomycin-related lipopeptide refers to compounds described above, and salts thereof.

The term "lantibiotic" is derived from "lanthionine-containing peptide antibiotic". Bacteria are known to produce a family of lantibiotics, which are ribosomally synthesized and usually activated by post-translational modification involving dehydration (by a dehydratase) and then cyclisation (by a cyclase) to create the active bacteriocin. In one embodiment the lantibiotic is nisin.

The term "antibiotic resistance" refers to a type of drug resistance where a microorganism (e.g., S. aureus bacterium) has developed the ability to survive exposure to an antibiotic or antimicrobial peptide. Evolutionary stress such as exposure to antibiotics selects for the antibiotic resistant trait. A bacterium may carry several resistance genes. "Antibiotic resistance" has an opposite meaning as compared to "antibiotic susceptibility", that is, a high antibiotic resistance means a low antibiotic susceptibility and vice versa.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts PILR, e.g., in the fluid phase or colloidal phase, but also situations where the agonist or antagonist does not contact the cell or the receptor.

EXAMPLES

Generation of Fab Fragments and Antibodies that are Specific for MprF

For the selection of antibodies specifically recognizing MprF a commercially available phage display library, the MorphoSys HuCAL PLATINUM® library was used. Said antibody library is based on the HuCAL® concept (Knappik et al., (2000) J Mol Biol 296:57-86) and employs the CysDisplay® technology for displaying the Fab on the phage surface (WO2001/05950 to Lohning). M-C4.4 and M-C4.5 were selected form the commercially available MorphoSys Ylanthia® library. However, any other available antibody library would be suitable to identify MprF antibodies.

To identify MprF antibodies specific panning strategies had been developed to target MprF. Thereby specific peptides mimicking the extracellular loops of MprF were generated and used as antigen for respective pannings. All described panning strategies and antigens were used for the antibody selection process. Each panning strategy comprised at least 3 individual rounds of panning and contained unique antigens, antigen concentrations and washing stringency.

Example 1: Selection and Synthesis of the Peptides Used for Panning

The in silico analysis of the MprF sequence led to the prediction of two possible membrane topologies of MprF. The correct topology was determined using lacZ- and phoA-fusions. Results are shown in FIG. 1.

The extracellular peptides of MprF, i.e. the peptides of SEQ ID NOs.: 2-7 were custom-synthesized as linear and cyclic peptides by JPT Peptide Technologies GmbH (Berlin).

In case of cyclic peptides an N-terminal and a C-terminal Cysteine was added to enable cyclization. Biotin was coupled to the peptide via a Ttds-linker. Cyclization and coupling of linker and Biotin was performed by JPT Peptide Technologies.

In case of linear peptides an N-terminal Cysteine was introduced (SEQ ID NOs.: 108-113) to enable coupling to carrier proteins. For some peptides (SEQ ID No.: 111 and SEQ ID NO.: 112) additional Glycins had to be introduced to improve solubility. Amino acids within the peptides not representing S. aureus amino acids are indicated in bold underlined.

| | |
|---|---|
| CELSGINFKDTLVEFSKINR, | (SEQ ID NO.: 108) |
| CYKNYTHDKKKLVHF, | (SEQ ID NO.: 109) |
| CSMVRPPDKNNRFVG, | (SEQ ID NO.: 110) |
| CGLGFKTLGVPEEKV, | (SEQ ID NO.: 111) |
| CGGDALYDGNHLT, | (SEQ ID NO.: 112) |
| CDIYTIEMHTSVLR. | (SEQ ID NO.: 113) |

Prior to their use in pannings the linear peptides were coupled using NHS/EDC chemistry and two different linkers to the carrier proteins bovine serum albumin (BSA) and human transferrin (Trf).

Example 2: Generation and Characterization of Fab Fragments and Antibodies Specific for MprF All described panning strategies and antigens were used for the antibody selection process. Each panning strategy comprised of at least 3 individual rounds of panning and contained unique antigens, antigen concentrations and washing stringency. Furthermore all described panning strategies and antigens can be combined and mixed and used as various differential panning strategies.

a) Panning with Linear Peptide-Conjugates as Antigens

Recombinant antibodies were generated from the HuCAL PLATINUM® library by three iterative rounds of panning on the peptide-carrier protein conjugates coupled to magnetic Dynal M-450 Epoxy beads (Invitrogen 140-11).

The antigen coupled beads were incubated over night at room temperature, blocked by addition of Tris, pH7.4, and subsequently re-suspended in PBS.

The antigen used for panning was alternated from Trf conjugate to BSA conjugate in each round to deplete carrier- or linker-specific antibodies. In addition, the phage library was blocked with BSA and Trf prior to every panning round with a blocking solution containing 5% BSA and 0.5% Trf for 2 h at room temperature.

b) Panning with Cyclic Biotinylated Peptides as Antigen

Recombinant antibodies were generated from the HuCAL PLATINUM® library by three iterative rounds of panning; wherein the phage antibody library was incubated with the antigen in solution and antigen-antibody-phage complexes were captured with streptavidin coated beads. (Dynal M-280)

c) Washing and Elution for all Pannings

Unspecific phages were washed away from the bead-antigen-antibody-phage complexes extensively by using PBST and PBS. Remaining phages were eluted, and eluted phages were used immediately for infection of E. coli TG1 bacteria. After rescue of the phages by using helper phage the polyclonal amplified phage output was used in consecutive selection steps.

Subsequent panning round 2 and 3 were performed in a similar fashion with prolonged washing steps and reduced antigen concentration to increase stringency and discard antibodies having low specificity and affinity. The peptide antigens were used either consistently (cyclic peptides) throughout the 3 rounds of panning or in an alternating manner (carrier protein was alternated).

d) Cloning of Fab-Encoding DNA into Expression Vector and Expression/Purification After the 3rd round of panning the DNA of the eluted antigen-specific phages was isolated from the infected bacteria and the Fab-encoding DNA was subcloned via PCR into specific Fab expression vectors.

After transformation of TG1-F bacteria, using the Fab-encoding vectors, 368 individual colonies were randomly picked for each panning and expression and preparation of cell lysates containing HuCAL-Fab fragments were performed. Fab-containing crude extracts were used for the initial screening and characterization.

For further characterization purified Fabs had been used. *E. coli* TG1F− cultures (250 mL) containing the chosen antibody genes were grown at 30° C. until $OD_{600\,nm}$ reached 0.5, and the antibody expression was induced by adding IPTG to a final concentration of 1 mM. After further incubation for at least 14 hours at 30° C., the cells were harvested, chemically lysed, and the soluble crude extract was subjected to one-step affinity chromatography (Ni-NTA agarose, Qiagen). After elution of the purified antibodies from the column, the buffer was changed from elution buffer to 3×PBS, pH 7.4, and the concentration was determined by $UV_{280\,nm}$ measurement. Purity and activity was tested subsequently by Coomassie-stained SDS-PAGE under reducing conditions and ELISA, respectively.

Altogether Fabs against all six peptides could be isolated from the pannings and showed specific binding to the respective peptides (signal at least 5-fold over background). A representative selection of 36 unique Fabs against all six peptides was selected for conversion into IgG1 format. Altogether 22 out of 36 clones were successfully converted into a full length human IgG1 format, expressed in a human cell line and purified via protein A chromatography for further analysis.

Example 3: Characterization of Selected MprF Antibodies in ELISA

The IgGs were tested for binding to the antigen, which was used in their selection. Also binding to other MprF-peptides was tested to check for selectivity.

For ELISAs with linear antigen, the peptides coupled to BSA or transferrin were coated at a concentration of 5 µg/ml to Maxisorp plates (Nunc). The plates were blocked using 5% milk powered in PBS. After blocking of the plates the IgGs were added at various concentrations. MprF-specific IgGs were detected using goat-anti-human IgG (Sigma).

For ELISAs with cyclic antigen, the biotinylated cyclic peptides (final conc. 5 µg/ml) were incubated with IgGs in PBS. Then the mix was transferred to a pre-blocked Neutravidin plate (Thermo Scientific), incubated and then the plate was washed with PBS containing 0.5% of TWEEN20. MprF-specific IgGs were detected using goat-anti-human IgG (Sigma).

In both cases washing was performed using PBST (TBS with 0.05% TWEEN20. Detection was performed using alkaline phosphatase coupled Goat anti-human IgG (Sigma Cat. # A-8542 and Attophos™ substrate Roche, Cat. #11681982001). Fluorescence was measured at an excitation of 440±25 nm and an emission of 550±35 nm. Full signal intensity is typically reached after 5-15 min at room temperature.

The following twelve antibodies were further investigated:

TABLE 2

| ID number | Antigen | Framework |
| --- | --- | --- |
| M-L1 | Linear peptide, loop 1 | VH1A kappa 3 |
| M-L4 | Linear peptide, loop 4 | VH3-23 kappa 1 |

TABLE 2-continued

| ID number | Antigen | Framework |
| --- | --- | --- |
| M-C1 | Cyclic peptide, loop 1 | VH3-23 kappa 3 |
| M-C4.1 | Cyclic peptide, loop 4 | VH1A kappa 1 |
| M-C4.2 | Cyclic peptide, loop 4 | VH3-23 kappa 1 |
| M-C4.3 | Cyclic peptide, loop 4 | VH1A kappa 1 |
| M-C4.4 | Cyclic peptide, loop 4 | VH3-23 |
| M-C4.5 | Cyclic peptide, loop 4 | VH6-1 |
| M-C5.1 | Cyclic peptide, loop 5 | VH1A kappa 1 |
| M-C5.2 | Cyclic peptide, loop 5 | VH3-23 kappa 1 |
| M-C6.1 | Cyclic peptide, loop 6 | VH1A kappa 1 |
| M-C6.2 | Cyclic peptide, loop 6 | VH1A kappa 1 |

Results and specific binding of each of the disclosed antibodies to its respective antigen are shown in FIGS. 2, 3, 4, and 15.

Example 4: MprF Antibodies Specifically Bind to *S. aureus* in ELISA

The specificity of the purified antibodies was tested for binding to whole cell *Staphylococcus aureus* in an ELISA assay. *Escherichia coli* bacteria were used as a negative control. Antibodies in Table 2 showed specific binding to whole *Staphylococcus aureus*.

Representative examples are shown in FIG. 5.

For ELISA on *S. aureus* the Protein A deletion mutant (delta spa) or the mutant with an additional deletion in MprF (delta spa delta mprf) were grown to mid log phase, than washed in PBS and resuspended in saline to a final $OD_{600}$ of 0.6. This bacterial culture was coated on Maxisorp plates (Nunc). Plates were blocked with 2% BSA/PBS and washed with TSB containing 0.5% TWEEN20. MprF-specific IgGs were detected using goat-anti-human IgG (Sigma).

Example 5: Functional Characterization: Studies with Nisin

In this experiment killing of *Staphylococcus aureus* was tested. Nisin was used as an exemplary cationic antimicrobial compound. Nisin was tested in combination with selected antibodies of the present invention. An anti-lysozyme antibody was used as a negative control.

Overnight cultures of *S. aureus* SA113 Δspa were diluted in fresh MHB medium and adjusted to $OD_{600}$ 0.25 (~1.5× $10^7$ cells). Antibodies were adjusted to a concentration of 1 mg/ml and 10 µl were applied per well of a 96 well plate and diluted in 90 µl of the adjusted cell suspension (final antibody concentration: 100 µg/ml). Cells were grown in the presence of anti-lysozyme antibody (control) or with the anti-MprF antibodies. Duplicates were employed for each assay. After 3 hours of incubation under shaking conditions at 37° C., optical density was determined, adjusted to $OD_{600}$ 0.025 in 500 µl ice cold PBS buffer. 80 µl of the adjusted cell suspension were diluted with 20 µl of antimicrobial substances to final concentrations of 22.5 µg/ml nisin. After incubation for 2 hours under shaking conditions at 37° C., the cell suspensions were diluted 1:2000 and 100 µl of each duplicate was plated in triplicates on TSB medium containing agar plates to obtain a representative value of bacterial survival. Cells treated without antimicrobial substance were set at 100% and survival values were calculated with cells treated with antimicrobial substances. At least three independent assays were employed.

Results are depicted in FIG. 6. The antibodies of the present invention strongly increased the sensitivity of *Staphylococcus aureus* towards nisin, indicated by a strongly increased killing of staphylococci. The most pronounced effects were observed with antibodies M-C4.1, M-C4.2, M-C5.1 and M-C6.2.

Comparable effects were observed in a growth inhibition assay using S. aureus SA113. Therefore S. aureus (S. aureus SA113) cells grown to mid-log phase were used to inoculate fresh TSB medium. These cultures were mixed with anti-MprF (1 µM) antibody or control IgG respectively or with anti-MprF (1 µM) antibody or control IgG in combination with nisin (6 µg/ml). The growth of the S. aureus in presence of anti-MprF antibody was monitored in culture plates shaking at 37° C. by measuring $OD_{600}$. While control antibody or anti-MprF antibody alone did not significantly impair growths of bacteria, an effect of nisin alone in terms of reducing growths of bacteria was observable. However, the antimicrobial effect of nisin was significantly increased in the presence of anti-MprF antibody. (FIG. 7)

Example 6: Functional Characterization: Studies with Daptomycin

The previous experiment was repeated, but instead of nisin, daptomycin is used. Again, a strong increase of sensitivity of Staphylococcus aureus towards daptomycin is observed when combined with the antibodies of the present invention (representative example in FIG. 8).

The experiment was performed as described in Example 5. Instead of nisin, 12.5 µg/ml Daptomycin was used.

Example 7: Functional Characterization: Studies with LL-37

The previous experiment was repeated, but instead of nisin LL-37 is used. Again, a strong increase of sensitivity of Staphylococcus aureus towards LL-37 is observed when combined with the antibodies of the present invention.

The experiment was performed as described in Example 5. Instead of nisin, 45.0 µg/ml of LL-37 was used (representative example in FIG. 9).

Example 8: Functional Characterization: Studies to Analyze Effect of MprF Antibodies on Charge of S. aureus Membrane and Flippase Activity of MprF The flippase domain of MprF translocates the positively charged lipid lysyl-phosphatidylglycerol into the outer leaflet of the membrane and thereby prevents the interaction with antimicrobial peptides and daptomycin with the membrane. M-C4.1 targets an extracellular loop of the flippase and is able to increase the killing activity of nisin, daptomycin and LL-37, suggesting that M-C4.1 interferes with the flippase reaction of MprF.

Cytochrome C Repulsion Assay

The repulsion of positively charged cytochrome C has been repeatedly employed to investigate charge dependent cell surface modifications in bacteria, including the flippase reaction of MprF, which leads to increased positively charged lipids in the outer leaflet of the membrane and to increased repulsion of cytochrome C (Ernst et al., PLoS Pathogens 2009). Briefly, cells were grown in the presence of M-C4.1 or anti-lysozyme for 3 hours, followed by incubation with cytochrome C for 15 minutes and measurement of optical density of the supernatant in order to determine repulsion of positively charged cytochrome C. The established cytochrome C repulsion assay was scaled down to accommodate for the reduced amount of bacteria employed in the killing-assays.

Pre-incubation of M-C4.1 with S. aureus SA113 Δspa led to 40% decreased repulsion of cytochrome C, compared to pre-incubation with anti-lysozyme antibodies, indicating that M-C4.1 inhibits the flippase reaction of MprF. The S. aureus SA113 spa-mprF double deletion mutant treated with either M-C4.1 or anti-lysozyme served as negative controls and were significantly impaired in their capacity to repulse cytochrome C (55-75% reduced repulsion). (FIG. 10)

Annexin V Assay

Annexin V binds preferentially to negatively charged phospholipids and is therefore a useful tool for measuring the relative content of MprF-mediated flipping of lysyl-phosphatidylglycerol, as translocation leads to reduced accessibility of negatively charged phospholipids in the outer leaflet of the membrane and therefore to reduced binding of annexin V. Cells (S. aureus SA113 Δspa) were grown in the presence of M-C4.1 or anti-lysozyme antibody and then treated with annexin V for 15 minutes before being analyzed by flow cytometry for surface-bound fluorophore (FL-4 channel). Data are expressed in relative fluorescence units and compared to cells pre-treated with anti-lysoyzme set at 100% fluorescence.

Cells pre-treated with M-C4.1 bound significantly more annexin V (70% increased binding) indicating that the pre-treatment with M-C4.1 had led to impaired flipping of lysyl-phosphatidylglycerol to the outer leaflet of the membrane. (FIG. 11)

Example 9: ELISA-Based Cross-Competition Assay

Cross-competition of an anti-MprF antibody or another MprF binding agent may be detected by using an ELISA assay according to the following standard procedure. Likewise, cross-competition of an anti-MprF antibody or another MprF binding agent may be detected.

The general principle of the ELISA-assay involves coating of an anti-MprF antibody onto the wells of an ELISA plate. An excess amount of a second, potentially cross-competitive, anti-MprF antibody is then added in solution (i.e. not bound to the ELISA plate). Subsequently a limited amount of antigen (representing MprF specific structures) is then added to the wells.

The antibody which is coated onto the wells and the antibody in solution will compete for binding of the limited number of antigen molecules. The plate is then washed to remove antigen molecules that has not bound to the coated antibody and to also remove the second, solution phase antibody as well as any complexes formed between the second, solution phase antibody and the antigens. The amount of bound antigen is then measured using an appropriate antigen detection reagent. Therefore, the antigen may be fused with a tag, e.g. Fc, Flag, etc. which can be detected via an appropriate tag-specific antibody.

An antibody in solution that is cross-competitive to the coated antibody will be able to cause a decrease in the number of antigen molecules that the coated antibody can bind relative to the number of antigen molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y MprF binding sites per well are at least 10 fold higher than the moles of Ab-X MprF specific structures binding sites that are used, per well, during the coating of the ELISA plate. Antigen (representing MprF specific structures, e.g. linear or cyclic extracellular loop) is then added such that the moles of antigen added per well were at least 25-fold lower than the moles of Ab-X MprF binding sites that are used for coating each well. Following a suitable incubation period, the ELISA plate is washed and an antigen detection reagent is added to measure the amount of antigen molecules specifically bound by the coated anti-MprF antibody (in this case Ab-X). The background signal for the assay is defined as the signal obtained in wells with the coated antibody (in this case Ab-X), second solution phase antibody (in this case Ab-Y), buffer only and antigen detection reagents. The positive control signal for the assay is defined as the signal obtained in wells with the coated antibody (in this case Ab-X), second solution phase antibody buffer only (i.e. no second solution phase antibody), antigen detection reagents. The ELISA assay needs to be run in such a manner so as to have the positive control signal be at least 6 times the background signal.

To avoid any artifacts (e.g. significantly different affinities between Ab-X and Ab-Y for MprF or MprF specific structures) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Example 10: Functional Characterization: Studies with Clinical *S. aureus* Strains and Daptomycin In this experiment killing of *Staphylococcus aureus* clinical isolate 703 (described in Jones et al., AAC 2008) by daptomycin in the presence of an MprF specific antibody was analyzed. The experiment was performed as described in Example 5. Instead of nisin, 11 µg/ml daptomycin was used and instead of *S. aureus* SA113 Δspa the *Staphylococcus aureus* clinical isolate 703 was used.

*Staphylococcus aureus* clinical isolate 703 was described in Jones et al., AAC 2008 to be non-responsive to daptomycin. However, in the presence of an anti-MprF antibody survival of *S. aureus* clinical 703 bacteria is significantly reduced. Therefor interference with MprF using a MprF-specific antibody induced susceptibility of *S. aureus* clinical 703 bacteria to daptomycin (FIG. 13).

Example 11: Growth Inhibition of Clinical Isolate *S. aureus* USA300 (MRSA)

In this experiment growth inhibition of *Staphylococcus aureus* clinical isolate USA300 by nisin was tested in the presence of an MprF specific antibody. While control antibody or anti-MprF antibody alone did not impair growths of bacteria, an effect of nisin alone in terms of reducing bacterial growths was observed. However, in the presence of anti-MprF antibody the antimicrobial effect of nisin was significantly increased, and growth of bacteria was abolished over a period of 24 h (FIG. 14).

The experiment was performed as described in Example 5. Instead of *S. aureus* SA113 the clinical isolate *S. aureus* USA300 was used. The concentration of nisin was 4.5 µg/ml instead of 6 µg/ml nisin.

TABLE 3

| ID# | | Seq. ID: | [aa]/DNA |
|---|---|---|---|
| M-L1 | HCDR1 | Seq. ID: 8 | GGTFNSYAIH |
| | HCDR2 | Seq. ID: 9 | GIIPIFGIANYAQKFQG |
| | HCDR3 | Seq. ID: 10 | DQYTYDYYRAFDY |
| | LCDR1 | Seq. ID: 11 | RASQSVRDNLA |
| | LCDR2 | Seq. ID: 12 | GASNRAT |
| | LCDR3 | Seq. ID: 13 | QQYDHSPRT |
| | VL | Seq. ID: 14 | DIVLTQSPATLSLSPGERATLSCRASQSVRDNLAWYQQKPGQAPRLLIYGASNRATGIPARFSGSGSGTDFTLTISSLEPEDFAVYYCQQYDHSPRTFGQGTKVEIKRT |
| | VH | Seq. ID: 15 | QVQLVQSGAEVKKPGSSVKVSCKASGGTFNSYAIHWVRQAPGQGLEWMGGIIPIFGIANYAQKFQGRVTITADESTSTAYMELSSLRSEDTAVYYCARDQYTYDYYRAFDYWGQGTLVTVSS |
| | VL (DNA) | Seq. ID: 16 | GATATCGTGCTGACCCAGAGCCCGGCGACCCTGAGCCTGAGCCCGGGTGAACGTGCCACCCTGAGCTGCAGAGCGAGCCAGTCTGTTCGTGACAACCTGGCTTGGTACCAGCAGAAACCGGGCCAGGCCCCGCGTCTATTAATCTACGGTGCTTCTAACCGTGCGACCGGCATTCCGGCGCGTTTTAGCGGCAGCGGATCCGGCACCGATTTCACCCTGACCATTAGCAGCCTGGAACCGGAAGACTTTGCGGTGTATTATTGCCAGCAGTACGACCATTCTCCGCGTACCTTTGGCCAGGGCACGAAAGTTGAAATTAAACGTACG |

TABLE 3-continued

| ID# | | Seq. ID: | [aa]/DNA |
|---|---|---|---|
| | VH (DNA) | Seq. ID: 17 | CAGGTGCAATTGGTGCAGAGCGGTGCCGAAGTGAA AAAACCGGGCAGCAGCGTGAAAGTTAGCTGCAAAG CATCCGGAGGGACGTTTAACTCTTACGCTATCCATT GGGTGCGCCAGGCCCCGGGCCAGGGCCTCGAGTG GATGGGCGGTATCATCCCGATCTTCGGCATCGCGA ACTACGCCCAGAAATTTCAGGGCCGGGTGACCATT ACCGCCGATGAAAGCACCAGCACCGCCTATATGGA ACTGAGCAGCCTGCGCAGCGAAGATACGGCCGTGT ATTATTGCGCGCGTGACCAGTACACTTACGACTACT ACCGTGCTTTCGATTACTGGGGCCAAGGCACCCTG GTGACTGTTAGCTCA |
| M-L4 | HCDR1 | Seq. ID: 18 | SYAMS |
| | HCDR2 | Seq. ID: 19 | IISYDGSSTYYADSVKG |
| | HCDR3 | Seq. ID: 20 | TATSGSRGYFDY |
| | LCDR1 | Seq. ID: 21 | RASQDISSWLN |
| | LCDR2 | Seq. ID: 22 | GASTLQS |
| | LCDR3 | Seq. ID: 23 | QQHYTSPVT |
| | VL | Seq. ID: 24 | DIQMTQSPSSLSASVGDRVTITCRASQDISSWLNWYQ QKPGKAPKLLIFGASTLQSGVPSRFSGSGSGTDFTLTI SSLQPEDFATYYCQQHYTSPVTFGQGTKVEIKRT |
| | VH | Seq. ID: 25 | EVQLLESGGGLVQPGGSLRLSCAASGFTFRSYAMSW VRQAPGKGLEWVSIISYDGSSTYYADSVKGRFTISRDN SKNTLYLQMNSLRAEDTAVYYCARTATSGSRGYFDY WGQGTLVTVSS |
| | VL (DNA) | Seq. ID: 26 | GATATCCAGATGACCCAGAGCCCGAGCAGCCTGAG CGCCAGCGTGGGCGATCGCGTGACCATTACCTGCA GAGCCAGCCAGGACATTTCTTCTTGGCTGAACTGGT ACCAGCAGAAACCGGGCAAAGCGCCGAAACTATTA ATCTTCGGTGCTTCTACTCTGCAAAGCGGCGTGCC GAGCCGCTTTAGCGGCAGCGGATCCGGCACCGATT TCACCCTGACCATTAGCTCTCTGCAACCGGAAGACT TTGCGACCTATTATTGCCAGCAGCATTACACTTCTC CGGTTACCTTTGGCCAGGGCACGAAAGTTGAAATTA AACGTACG |
| | VH (DNA) | Seq. ID: 27 | GAAGTGCAATTGCTGGAAAGCGGCGGTGGCCTGGT GCAGCCGGGTGGCAGCCTGCGTCTGAGCTGCGCG GCGTCCGGATTCACCTTTCGTTCTTACGCTATGTCT TGGGTGCGCCAGGCCCCGGGCAAAGGTCTCGAGT GGGTTTCCATTATCTCTTACGACGGTTCTTCTACCTA CTATGCGGATAGCGTGAAAGGCCGCTTTACCATCA GCCGCGATAATTCGAAAAACACCCTGTATCTGCAA TGAACAGCCTGCGTGCGGAAGATACGGCCGTGTAT TATTGCGCGCGTACTGCTACTTCTGGTTCTCGTGGT TACTTCGATTACTGGGGCCAAGGCACCCTGGTGAC TGTTAGCTCA |
| M-C1 | HCDR1 | Seq. ID: 28 | SYAMN |
| | HCDR2 | Seq. ID: 29 | VISSDGSDTYYADSVKG |
| | HCDR3 | Seq. ID: 30 | ESYYIGWDY |
| | LCDR1 | Seq. ID: 31 | RASQRVSSSFLA |
| | LCDR2 | Seq. ID: 32 | LASNRAT |
| | LCDR3 | Seq. ID: 33 | LQYGHYPPT |
| | VL | Seq. ID: 34 | DIVLTQSPATLSLSPGERATLSCRASQRVSSSFLAWY QQKPGQAPRLLIYLASNRATGIPARFSGSGSGTDFTLT ISSLEPEDFAVYYCLQYGHYPPTFGQGTKVEIKRT |
| | VH | Seq. ID: 35 | EVQLLESGGGLVQPGGSLRLSCAASGFTFSSYAMNW VRQAPGKGLEWVSVISSDGSDTYYADSVKGRFTISRD NSKNTLYLQMNSLRAEDTAVYYCARESYYIGWDYWG QGTLVTVSS |

TABLE 3-continued

| ID# | | Seq. ID: | [aa]/DNA |
|---|---|---|---|
| | VL (DNA) | Seq. ID: 36 | GATATCGTGCTGACCCAGAGCCCGGCGACCCTGAGCCTGAGCCCGGGTGAACGTGCCACCCTGAGCTGCAGAGCGAGCCAGCGTGTTTCTTCTTCTTTCCTGGCTTGGTACCAGCAGAAACCGGGCCAGGCCCCGCGTCTATTAATCTACCTGGCTTCTAACCGTGCGACCGGCATTCCGGCGCGTTTTAGCGGCAGCGGATCCGGCACCGATTTCACCCTGACCATTAGCAGCCTGGAACCGGAAGACTTTGCGGTGTATTATTGCCTGCAGTACGGTCATTACCCGCCGACCTTTGGCCAGGGCACGAAAGTTGAAATTAAACGTACG |
| | VH (DNA) | Seq. ID: 37 | CAGGTGCAATTGCTGGAAAGCGGCGGTGGCCTGGTGCAGCCGGGTGGCAGCCTGCGTCTGAGCTGCGCGGCGTCCGGATTCACCTTTTCTTCTTACGCTATGAACTGGGTGCGCCAGGCCCCGGGCAAAGGTCTCGAGTGGGTTTCCGTTATCTCTTCTGACGGTTCTGACACCTACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGAATCTTACTACATCGGTTGGGATTACTGGGGCCAAGGCACCCTGGTGACTGTTAGCTCA |
| M-C4.1 | HCDR1 | Seq. ID: 38 | SYAIS |
| | HCDR2 | Seq. ID: 39 | GIIPIFGMATYAQKFQG |
| | HCDR3 | Seq. ID: 40 | SLFGRAY |
| | LCDR1 | Seq. ID: 41 | RASQSISSFLA |
| | LCDR2 | Seq. ID: 42 | DASSLQS |
| | LCDR3 | Seq. ID: 43 | LQADSTSYT |
| | VL | Seq. ID: 44 | DIQMTQSPSSLSASVGDRVTITCRASQSISSFLAWYQQKPGKAPKLLIYDASSLQSGVPSRFSGSGSGTDFTLTISSLQPEDFATYYCLQADSTSYTFGQGTKVEIKRT |
| | VH | Seq. ID: 45 | QVQLVQSGAEVKKPGSSVKVSCKASGGTFNSYAISWVRQAPGQGLEWMGGIIPIFGMATYAQKFQGRVTITADESTSTAYMELSSLRSEDTAVYYCARSLFGRAYWGQGTLVTVSS |
| | VL (DNA) | Seq. ID: 46 | GATATCCAGATGACCCAGAGCCCGAGCAGCCTGAGCGCCAGCGTGGGCGATCGCGTGACCATTACCTGCAGAGCCAGCCAGTCTATTTCTTCTTTCCTGGCTTGGTACCAGCAGAAACCGGGCAAAGCGCCGAAACTATTAATCTACGACGCTTCTTCTCTGCAAAGCGGCGTGCCGAGCCGCTTTAGCGGCAGCGGATCCGGCACCGATTTCACCCTGACCATTAGCTCTCTGCAACCGGAAGACTTTGCGACCTATTATTGCCTGCAGGCTGACTCTACTTCTTACACCTTTGGCCAGGGCACGAAAGTTGAAATTAAACGTACG |
| | VH (DNA) | Seq. ID: 47 | CAGGTGCAATTGGTGCAGAGCGGTGCCGAAGTGAAAAAACCGGGCAGCAGCGTGAAAGTTAGCTGCAAAGCATCCGGAGGGACGTTTAACTCTTACGCTATCTCTTGGGTGCGCCAGGCCCCGGGCCAGGGCCTCGAGTGGATGGGCGGTATCATCCCGATCTTCGGCATGGCGACTTACGCCCAGAAATTTCAGGGCCGGGTGACCATTACCGCCGATGAAAGCACCAGCACCGCCTATATGGAACTGAGCAGCCTGCGCAGCGAAGATACGGCCGTGTATTATTGCGCGCGTTCTCTGTTCGGTCGTGCTTACTGGGGCCAAGGCACCCTGGTGACTGTTAGCTCA |
| M-C4.2 | HCDR1 | Seq. ID: 48 | SYAMH |
| | HCDR2 | Seq. ID: 49 | VISSVGSSTYYADSVKG |
| | HCDR3 | Seq. ID: 50 | GGLDV |
| | LCDR1 | Seq. ID: 51 | RASQDISKYLN |
| | LCDR2 | Seq. ID: 52 | AASRLQS |
| | LCDR3 | Seq. ID: 53 | QQGDSTPFT |

TABLE 3-continued

| ID# | | Seq. ID: | [aa]/DNA |
|---|---|---|---|
| | VL | Seq. ID: 54 | DIQMTQSPSSLSASVGDRVTITCRASQDISKYLNWYQ QKPGKAPKLLIYAASRLQSGVPSRFSGSGSGTDFTLTI SSLQPEDFATYYCQQGDSTPFTFGQGTKVEIKRT |
| | VH | Seq. ID: 55 | EVQLLESGGGLVQPGGSLRLSCAASGFTFSSYAMHW VRQAPGKGLEWVSVISSVGSSTYYADSVKGRFTISRD NSKNTLYLQMNSLRAEDTAVYYCARGGLDVWGQGTL VTVSS |
| | VL (DNA) | Seq. ID: 56 | GATATCCAGATGACCCAGAGCCCGAGCAGCCTGAG CGCCAGCGTGGGCGATCGCGTGACCATTACCTGCA GAGCCAGCCAGGACATTTCTAAATACCTGAACTGGT ACCAGCAGAAACCGGGCAAAGCGCCGAAACTATTA ATCTACGCTGCTTCTCGTCTGCAAAGCGGCGTGCC GAGCCGCTTTAGCGGCAGCGGATCCGGCACCGATT TCACCCTGACCATTAGCTCTCTGCAACCGGAAGACT TTGCGACCTATTATTGCCAGCAGGGTGACTCTACTC CGTTCACCTTTGGCCAGGGCACGAAAGTTGAAATTA AACGTACG |
| | VH (DNA) | Seq. ID: 57 | GAAGTGCAATTGCTGGAAAGCGGCGGTGGCCTGGT GCAGCCGGGTGGCAGCCTGCGTCTGAGCTGCGCG GCGTCCGGATTCACCTTTTCTTCTTACGCTATGCATT GGGTGCGCCAGGCCCGGGCAAAGGTCTCGAGTG GGTTTCCGTTATCTCTTCTGTTGGTTCTTCTACCTAC TATGCGGATAGCGTGAAAGGCCGCTTTACCATCAG CCGCGATAATTCGAAAAACACCCTGTATCTGCAAAT GAACAGCCTGCGTGCGGAAGATACGGCCGTGTATT ATTGCGCGCGTGGTGGTCTGGACGTTTGGGGCCAA GGCACCCTGGTGACTGTTAGCTCA |
| M-C4.3 | HCDR1 | Seq. ID: 58 | DHTIS |
| | HCDR2 | Seq. ID: 59 | GIIPIVGIANYAQKFQG |
| | HCDR3 | Seq. ID: 60 | EYYVPDSGWFDY |
| | LCDR1 | Seq. ID: 61 | RASQDISDYLV |
| | LCDR2 | Seq. ID: 62 | DASNLQS |
| | LCDR3 | Seq. ID: 63 | QQYYHYRT |
| | VL | Seq. ID: 64 | DIQMTQSPSSLSASVGDRVTITCRASQDISDYLVWYQ QKPGKAPKLLIYDASNLQSGVPSRFSGSGSGTDFTLTI SSLQPEDFATYYCQQYYHYRTFGQGTKVEIKRT |
| | VH | Seq. ID: 65 | QVQLVQSGAEVKKPGSSVKVSCKASGGTFSDHTISW VRQAPGQGLEWMGGIIPIVGIANYAQKFQGRVTITADE STSTAYMELSSLRSEDTAVYYCAREYYVPDSGWFDY WGQGTLVTVSS |
| | VL (DNA) | Seq. ID: 66 | GATATCCAGATGACCCAGAGCCCGAGCAGCCTGAG CGCCAGCGTGGGCGATCGCGTGACCATTACCTGCA GAGCCAGCCAGGACATTTCTGACTACCTGGTTTGGT ACCAGCAGAAACCGGGCAAAGCGCCGAAACTATTA ATCTACGACGCTTCTAACCTGCAAAGCGGCGTGCC GAGCCGCTTTAGCGGCAGCGGATCCGGCACCGATT TCACCCTGACCATTAGCTCTCTGCAACCGGAAGACT TTGCGACCTATTATTGCCAGCAGTACTACCATTACC GTACCTTTGGCCAGGGCACGAAAGTTGAAATTAAAC GTACG |
| | VH (DNA) | Seq. ID: 67 | CAGGTGCAATTGGTGCAGAGCGGTGCCGAAGTGAA AAAACCGGGCAGCAGCGTGAAAGTTAGCTGCAAAG CATCCGGAGGGACGTTTTCTGACCACACTATCTCTT GGGTGCGCCAGGCCCGGGCCAGGGCCTCGAGTG GATGGGCGGTATCATCCCGATCGTTGGCATCGCGA ACTACGCCCAGAAATTTCAGGGCCGGGTGACCATT ACCGCCGATGAAAGCACCAGCACCGCCTATATGGA ACTGAGCAGCCTGCGCAGCGAAGATACGGCCGTGT ATTATTGCGCGCGTGAATACTACGTTCCGGACTCTG GTTGGTTCGATTACTGGGGCCAAGGCACCCTGGTG ACTGTTAGCTCA |

TABLE 3-continued

| ID# | | Seq. ID: | [aa]/DNA |
|---|---|---|---|
| M-05.1 | HCDR1 | Seq. ID: 68 | SYAIS |
| | HCDR2 | Seq. ID: 69 | GIVPIFGTANYAQKFQG |
| | HCDR3 | Seq. ID: 70 | VRYGYWDV |
| | LCDR1 | Seq. ID: 71 | RASQDIANWLN |
| | LCDR2 | Seq. ID: 72 | AASSLQS |
| | LCDR3 | Seq. ID: 73 | QQYISLPIT |
| | VL | Seq. ID: 74 | DIQMTQSPSSLSASVGDRVTITCRASQDIANWLNWYQ QKPGKAPKLLIYAASSLQSGVPSRFSGSGSGTDFTLTI SSLQPEDFATYYCQQYISLPITFGQGTKVEIKRT |
| | VH | Seq. ID: 75 | QVQLVQSGAEVKKPGSSVKVSCKASGGTFSSYAISW VRQAPGQGLEWMGGIVPIFGTANYAQKFQGRVTITAD ESTSTAYMELSSLRSEDTAVYYCARVRYGYWDVWGQ GTLVTVSS |
| | VL (DNA) | Seq. ID: 76 | GATATCCAGATGACCCAGAGCCCGAGCAGCCTGAG CGCCAGCGTGGGCGATCGCGTGACCATTACCTGCA GAGCCAGCCAGGACATTGCTAACTGGCTGAACTGG TACCAGCAGAAACCGGGCAAAGCGCCGAAACTATT AATCTACGCTGCTTCTTCTCTGCAAAGCGGCGTGCC GAGCCGCTTTAGCGGCAGCGGATCCGGCACCGATT TCACCCTGACCATTAGCTCTCTGCAACCGGAAGACT TTGCGACCTATTATTGCCAGCAGTACATCTCTCTGC CGATCACCTTTGGCCAGGGCACGAAAGTTGAAATTA AACGTACG |
| | VH (DNA) | Seq. ID: 77 | CAGGTGCAATTGGTGCAGAGCGGTGCCGAAGTGAA AAAACCGGGCAGCAGCGTGAAAGTTAGCTGCAAAG CATCCGGAGGGACGTTTTCTTCTTACGCTATCTCTT GGGTGCGCCAGGCCCCGGGCCAGGGCCTCGAGTG GATGGGCGGTATCGTTCCGATCTTCGGCACTGCGA ACTACGCCCAGAAATTTCAGGGCCGGGTGACCATT ACCGCCGATGAAAGCACCAGCACCGCCTATATGGA ACTGAGCAGCCTGCGCAGCGAAGATACGGCCGTGT ATTATTGCGCGCGTGTTCGTTACGGCTACTGGGATG TTTGGGGCCAAGGCACCCTGGTGACTGTTAGCTCA |
| M-05.2 | HCDR1 | Seq. ID: 78 | SYAVH |
| | HCDR2 | Seq. ID: 79 | VISGRGGSTYYADSVKG |
| | HCDR3 | Seq. ID: 80 | DHGYFDY |
| | LCDR1 | Seq. ID: 81 | RASQTISNHLG |
| | LCDR2 | Seq. ID: 82 | TASNLQS |
| | LCDR3 | Seq. ID: 83 | QQYSHSSYT |
| | VL | Seq. ID: 84 | DIQMTQSPSSLSASVGDRVTITCRASQTISNHLGWYQ QKPGKAPKLLIYTASNLQSGVPSRFSGSGSGTDFTLTI SSLQPEDFATYYCQQYSHSSYTFGQGTKVEIKRT |
| | VH | Seq. ID: 85 | EVQLLESGGGLVQPGGSLRLSCAASGFTFSSYAVHW VRQAPGKGLEWVSVISGRGGSTYYADSVKGRFTISRD NSKNTLYLQMNSLRAEDTAVYYCARDHGYFDYWGQG TLVTVSS |
| | VL (DNA) | Seq. ID: 86 | GATATCCAGATGACCCAGAGCCCGAGCAGCCTGAG CGCCAGCGTGGGCGATCGCGTGACCATTACCTGCA GAGCCAGCCAGACTATTTCTAACCATCTGGGTTGGT ACCAGCAGAAACCGGGCAAAGCGCCGAAACTATTA ATCTACACTGCTTCTAACCTGCAAAGCGGCGTGCCG AGCCGCTTTAGCGGCAGCGGATCCGGCACCGATTT CACCCTGACCATTAGCTCTCTGCAACCGGAAGACTT TGCGACCTATTATTGCCAGCAGTACTCTCATTCTTCT TACACCTTTGGCCAGGGCACGAAAGTTGAAATTAAA CGTACG |
| | VH (DNA) | Seq. ID: 87 | GAAGTGCAATTGCTGGAAAGCGGCGGTGGCCTGGT GCAGCCGGGTGGCAGCCTGCGTCTGAGCTGCGCG GCGTCCGGATTCACCTTTCTTCTTACGCTGTTCATT |

TABLE 3-continued

| ID# | | Seq. ID: | [aa]/DNA |
|---|---|---|---|
| | | | GGGTGCGCCAGGCCCCGGGCAAAGGTCTCGAGTG GGTTTCCGTTATCTCTGGTCGTGGTGGTTCTACCTA CTATGCGGATAGCGTGAAAGGCCGCTTTACCATCA GCCGCGATAATTCGAAAAACACCCTGTATCTGCAAA TGAACAGCCTGCGTGCGGAAGATACGGCCGTGTAT TATTGCGCGCGTGACCATGGTTACTTCGACTACTGG GGCCAAGGCACCCTGGTGACTGTTAGCTCA |
| M-C6.1 | HCDR1 | Seq. ID: 88 | IYAIS |
| | HCDR2 | Seq. ID: 89 | GIIPEFGTANYAQKFQG |
| | HCDR3 | Seq. ID: 90 | SQIYTLSYPKWFDF |
| | LCDR1 | Seq. ID: 91 | RASQDISNYLN |
| | LCDR2 | Seq. ID: 92 | DASNLQS |
| | LCDR3 | Seq. ID: 93 | LQYLQSPKT |
| | VL | Seq. ID: 94 | DIQMTQSPSSLSASVGDRVTITCRASQDISNYLNWYQ QKPGKAPKLLIYDASNLQSGVPSRFSGSGSGTDFTLTI SSLQPEDFATYYCLQYLQSPKTFGQGTKVEIKRT |
| | VH | Seq. ID: 95 | QVQLVQSGAEVKKPGSSVKVSCKASGGTFSIYAISWV RQAPGQGLEWMGGIIPEFGTANYAQKFQGRVTITADE STSTAYMELSSLRSEDTAVYYCARSQIYTLSYPKWFDF WGQGTLVTVSS |
| | VL (DNA) | Seq. ID: 96 | GATATCCAGATGACCCAGAGCCCGAGCAGCCTGAG CGCCAGCGTGGGCGATCGCGTGACCATTACCTGCA GAGCCAGCCAGGACATTTCTAACTACCTGAACTGGT ACCAGCAGAAACCGGGCAAAGCGCCGAAACTATTA ATCTACGACGCTTCTAACCTGCAAAGCGGCGTGCC GAGCCGCTTTAGCGGCAGCGGATCCGGCACCGATT TCACCCTGACCATTAGCTCTCTGCAACCGGAAGACT TTGCGACCTATTATTGCCTGCAGTACCTGCAGTCTC CGAAAACCTTTGGCCAGGGCACGAAAGTTGAAATTA AACGTACG |
| | VH (DNA) | Seq. ID: 97 | CAGGTGCAATTGGTGCAGAGCGGTGCCGAAGTGAA AAAACCGGGCAGCAGCGTGAAAGTTAGCTGCAAAG CATCCGGAGGGACGTTTTCTATCTACGCTATCTCTT GGGTGCGCCAGGCCCCGGGCCAGGGCCTCGAGTG GATGGGCGGTATCATCCCGGAATTCGGCACTGCGA ACTACGCCCAGAAATTTCAGGGCCGGGTGACCATT ACCGCCGATGAAAGCACCAGCACCGCCTATATGGA ACTGAGCAGCCTGCGCAGCGAAGATACGGCCGTGT ATTATTGCGCGCGTTCTCAGATCTACACTCTGTCTTA CCCGAAATGGTTCGACTTCTGGGGCCAAGGCACCC TGGTGACTGTTAGCTCA |
| M-C6.2 | HCDR1 | Seq. ID: 98 | SYAIS |
| | HCDR2 | Seq. ID: 99 | GIIPILGIANYAQKFQG |
| | HCDR3 | Seq. ID: 100 | SLPYRSDLYGFSRWSYHRVGMDV |
| | LCDR1 | Seq. ID: 101 | RASQDISNTLN |
| | LCDR2 | Seq. ID: 102 | AASTLQS |
| | LCDR3 | Seq. ID: 103 | QQVGSFPYT |
| | VL | Seq. ID: 104 | DIQMTQSPSSLSASVGDRVTITCRASQDISNTLNWYQ QKPGKAPKLLIYAASTLQSGVPSRFSGSGSGTDFTLTI SSLQPEDFATYYCQQVGSFPYTFGQGTKVEIKRT |
| | VH | Seq. ID: 105 | QVQLVQSGAEVKKPGSSVKVSCKASGGTFSSYAISW VRQAPGQGLEWMGGIIPILGIANYAQKFQGRVTITADE STSTAYMELSSLRSEDTAVYYCARSLPYRSDLYGFSR WSYHRVGMDVWGQGTLVTVSS |
| | VL (DNA) | Seq. ID: 106 | GATATCCAGATGACCCAGAGCCCGAGCAGCCTGAG CGCCAGCGTGGGCGATCGCGTGACCATTACCTGCA GAGCCAGCCAGGACATTTCTAACACTCTGAACTGGT ACCAGCAGAAACCGGGCAAAGCGCCGAAACTATTA ATCTACGCTGCTTCTACTCTGCAAAGCGGCGTGCC |

TABLE 3-continued

| ID# | | Seq. ID: | [aa]/DNA |
|---|---|---|---|
| | | | GAGCCGCTTTAGCGGCAGCGGATCCGGCACCGATT TCACCCTGACCATTAGCTCTCTGCAACCGGAAGACT TTGCGACCTATTATTGCCAGCAGGTTGGTTCTTTCC CGTACACCTTTGGCCAGGGCACGAAAGTTGAAATTA AACGTACG |
| | VH (DNA) | Seq. ID: 107 | CAGGTGCAATTGGTGCAGAGCGGTGCCGAAGTGAA AAAACCGGGCAGCAGCGTGAAAGTTAGCTGCAAAG CATCCGGAGGGACGTTTTCTTCTTACGCTATCTCTT GGGTGCGCCAGGCCCCGGGCCAGGGCCTCGAGTG GATGGGCGGTATCATCCCGATCCTGGGCATCGCGA ACTACGCCCAGAAATTTCAGGGCCGGGTGACCATT ACCGCCGATGAAAGCACCAGCACCGCCTATATGGA ACTGAGCAGCCTGCGCAGCGAAGATACGGCCGTGT ATTATTGCGCGCGTTCTCTGCCGTACCGTTCTGACC TGTACGGTTTCTCTCGTTGGTCTTACCATCGTGTTG GTATGGATGTTTGGGGCCAAGGCACCCTGGTGACT GTTAGCTCA |
| M-C4.4 HCDR1 | | Seq. ID: 119 | FTFSSYAIS |
| HCDR2 | | Seq. ID: 120 | VSAISGSGGSTYYAESVKG |
| HCDR3 | | Seq. ID: 121 | YPYPGYFDL |
| LCDR1 | | Seq. ID: 122 | SGDKLGDKYAY |
| LCDR2 | | Seq. ID: 123 | LVIYQDSKRPS |
| LCDR3 | | Seq. ID: 124 | QTWVSSISAF |
| VL | | Seq. ID: 125 | SYELTQPPSVSVSPGQTASITCSGDKLGDKYAYWYQQ KPGQSPVLVIYQDSKRPSGIPERFSGSNSGNTATLTIS GTQAEDEADYYCQTWVSSISAFVFGGGTKLTVLGQ |
| VH | | Seq. ID: 126 | EVQLLESGGGLVQPGGSLRLSCAASGFTFSSYAISWV RQAPGKGLEWVSAISGSGGSTYYAESVKGRFTISRDN SKNTLYLGMNSLRAEDTAVYYCARYPYPGYFDLWGQ GTLVTVSS |
| VL (DNA) | | Seq. ID: 127 | AGCTATGAACTGACCCAGCCGCCGAGCGTTAGCGT TAGCCCAGGCCAGACCGCCAGCATTACCTGTAGCG GCGACAAACTGGGCGACAAATACGCCTACTGGTAT CAGCAGAAACCGGGCCAGAGCCCGGTGCTGGTTAT CTATCAGGATAGCAAACGCCCGAGCGGCATTCCAG AACGCTTTAGCGGCAGCAACAGCGGCAACACCGCC ACCCTGACCATTAGCGGCACCCAGGCCGAAGACGA AGCCGATTATTACTGCCAGACTTGGGTTTCTTCTAT CTCTGCTTTCGTGTTTGGCGGCGGTACCAAGCTGA CCGTGCTGGGCCAG |
| VH (DNA) | | Seq. ID: 128 | GAAGTGCAGCTGCTGGAAAGCGGTGGCGGTCTGGT GCAGCCAGGTGGTAGCCTGCGCCTGAGCTGTGCC GCAAGCGGCTTTACCTTTAGCAGCTATGCCATTAGC TGGGTGCGCCAAGCACCAGGCAAAGGCCTGGAATG GGTGAGCGCCATTAGCGGCAGCGGTGGCAGCACC TATTATGCCGAGAGCGTGAAAGGTCGCTTTACCATT AGTCGCGATAACAGCAAAAACACCCTGTATCTGCAA ATGAACAGCCTGCGGGCAGAAGATACCGCAGTTTA TTATTGCGCGCGTTACCCTTACCCTGGTTATTTCGA CCTGTGGGGCCAGGGCACCCTGGTTACTGTCTCGA GC |
| M-C4.5 HCDR1 | | Seq. ID: 129 | DSVSSNSAAWN |
| HCDR2 | | Seq. ID: 130 | LGRTYYRSKWYNDYAVSVKS |
| HCDR3 | | Seq. ID: 131 | SAEPSYAYYHGFDY |
| LCDR1 | | Seq. ID: 132 | RASQGISSYLA |
| LCDR2 | | Seq. ID: 133 | LLIYAASTLQS |
| LCDR3 | | Seq. ID: 134 | QQRIIFPQ |
| VL | | Seq. ID: 135 | DIQLTQSPSFLSASVGDRVTITCRASQGISSYLAWYQQ KPGKAPKLLIYAASTLQSGVPSRFSGSGSGTEFTLTIS SLQPEDFATYYCQQRIIFPQTFGQGTKVEIKRT |

TABLE 3-continued

| ID# | Seq. ID: | [aa]/DNA |
|---|---|---|
| VH | Seq. ID: 136 | QVQLQQSGPGLVKPSQTLSLTCAISGDSVSSNSAAWN WIRQSPSRGLEWLGRTYYRSKWYNDYAVSVKSRITIN PDTSKNQFSLQLNSVTPEDTAVYYCARSAEPSYAYYH GFDYWGQGTLVTVSS |
| VL (DNA) | Seq. ID: 137 | GATATTCAGCTGACCCAGAGCCCGAGCTTTCTGAG CGCCAGCGTGGGCGATCGCGTGACCATTACCTGCC GCGCCAGCCAGGGCATTAGCAGCTATCTGGCCTGG TATCAGCAGAAACCGGGCAAAGCCCCGAAACTGCT GATCTATGCCGCCAGCACCCTGCAAAGCGGCGTGC CAAGCCGCTTTAGCGGCAGCGGTAGCGGCACCGA GTTCACCCTGACCATTAGCAGCCTGCAACCGGAAG ACTTTGCCACCTATTATTGCCAGCAGCGTATCATCTT CCCGCAGACCTTCGGCCAGGGTACCAAAGTGGAAA TCAAGCGGACC |
| VH (DNA) | Seq. ID: 138 | CAGGTGCAGCTGCAACAGAGCGGCCCAGGCCTGG TTAAACCGAGCCAGACCCTGAGCCTGACCTGCGCC ATTAGCGGCGATAGCGTTAGCAGCAACAGCGCCGC CTGGAACTGGATTCGCCAGAGCCCGAGCCGCGGTC TGGAATGGCTGGGCCGCACCTATTATCGCAGCAAA TGGTACAACGATTACGCCGTTAGCGTGAAAAGCCG CATTACCATTAACCCGGATACCAGCAAAAACCAGTT CAGCCTGCAACTGAACAGCGTGACCCCGGAAGATA CCGCCGTGTATTACTGCGCGCGTAGCGCAGAGCCT AGCTACGCATACTATCACGGTTTTGACTATTGGGGC CAGGGCACCCTGGTTACTGTCTCGAGC |

The invention claimed is:

1. An antibody or antibody fragment that is specific to an extracellular loop of the multiple peptide resistance factor (MprF) of *Staphylococcus aureus*, wherein said MprF is of SEQ ID NO:1 or an orthologue of SEQ ID NO: 1, wherein said antibody binds specifically to an extracellular loop of the MprF or the orthologue, wherein said antibody is a monoclonal antibody, chimeric antibody, humanized antibody, synthetic antibody or human monoclonal antibody, or a fragment of said antibody and wherein said antibody or antibody fragment increases susceptibility of a *Staphylococcus aureus* to a cationic antimicrobial peptide.

2. The antibody or antibody fragment of claim 1, wherein the cationic antimicrobial peptide is nisin, daptomycin, or cathelicidin.

3. The antibody or antibody fragment according to claim 1, wherein said antibody binds to the extracellular loop of the MprF, wherein the loop is of the amino acid sequence of ELSGINFKDTLVEFSKINR (SEQ ID NO: 2), YKNYTHDKKKLVHF (SEQ ID NO: 3), SMVRPPDKNNRFVG (SEQ ID NO: 4), LGFKTLGVPEEKV (SEQ ID NO: 5), DALYDGNHLT (SEQ ID NO: 6) or DIYTIEMHTSVLR (SEQ ID NO: 7).

4. The antibody or antibody fragment according to claim 1, wherein said antibody binds to an isolated peptide of ELSGINFKDTLVEFSKINR (SEQ ID NO: 2), YKNYTHDKKKLVHF (SEQ ID NO: 3), SMVRPPDKNNRFVG (SEQ ID NO: 4), LGFKTLGVPEEKV (SEQ ID NO: 5), DALYDGNHLT (SEQ ID NO: 6) or DIYTIEMHTSVLR (SEQ ID NO: 7).

5. A combination comprising the antibody or antibody fragment according to claim 1, and a cationic antimicrobial peptide.

6. The combination according to claim 5, wherein said antimicrobial peptide is a cyclic lipopeptide.

7. The combination according to claim 6, wherein said cyclic lipopeptide is daptomycin or a daptomycin-related lipopeptide.

8. The combination according to claim 5, wherein said combination is synergistic.

9. A pharmaceutical composition comprising the combination according to claim 5.

10. The antibody or antibody fragment according to claim 1 which is an IgG isotype.

* * * * *

SEQUENCE LISTING

<160> NUMBER OF SEQ ID NOS: 138

<210> SEQ ID NO 1
<211> LENGTH: 840
<212> TYPE: PRT
<213> ORGANISM: Staphylococcus aureus
<220> FEATURE:
<223> OTHER INFORMATION: MprF

<400> SEQUENCE: 1

```
Met Asn Gln Glu Val Lys Asn Lys Ile Phe Ser Ile Leu Lys Ile Thr
1               5                   10                  15

Phe Ala Thr Ala Leu Phe Ile Phe Val Ala Ile Thr Leu Tyr Arg Glu
            20                  25                  30

Leu Ser Gly Ile Asn Phe Lys Asp Thr Leu Val Glu Phe Ser Lys Ile
        35                  40                  45

Asn Arg Met Ser Leu Val Leu Leu Phe Ile Gly Gly Ala Ser Leu
    50                  55                  60

Val Ile Leu Ser Met Tyr Asp Val Ile Leu Ser Arg Ala Leu Lys Met
65                  70                  75                  80

Asp Ile Ser Leu Gly Lys Val Leu Arg Val Ser Tyr Ile Ile Asn Ala
                85                  90                  95

Leu Asn Ala Ile Val Gly Phe Gly Gly Phe Ile Gly Ala Gly Val Arg
            100                 105                 110

Ala Met Val Tyr Lys Asn Tyr Thr His Asp Lys Lys Leu Val His
        115                 120                 125

Phe Ile Ser Leu Ile Leu Ile Ser Met Leu Thr Gly Leu Ser Leu Leu
    130                 135                 140

Ser Leu Leu Ile Val Phe His Val Phe Asp Ala Ser Leu Ile Leu Asp
145                 150                 155                 160

Lys Ile Thr Trp Val Arg Trp Val Leu Tyr Val Val Ser Phe Phe Leu
```

```
            165                 170                 175
Pro Leu Phe Ile Ile Tyr Ser Met Val Arg Pro Asp Lys Asn Asn
            180                 185                 190

Arg Phe Val Gly Leu Tyr Cys Thr Leu Val Ser Cys Val Glu Trp Leu
            195                 200                 205

Ala Ala Ala Val Val Leu Tyr Phe Cys Gly Val Ile Val Asp Ala His
    210                 215                 220

Val Ser Phe Met Ser Phe Ile Ala Ile Phe Ile Ala Ala Leu Ser
225                 230                 235                 240

Gly Leu Val Ser Phe Ile Pro Gly Gly Phe Gly Ala Phe Asp Leu Val
                245                 250                 255

Val Leu Leu Gly Phe Lys Thr Leu Gly Val Pro Glu Glu Lys Val Leu
            260                 265                 270

Leu Met Leu Leu Leu Tyr Arg Phe Ala Tyr Tyr Phe Val Pro Val Ile
            275                 280                 285

Ile Ala Leu Ile Leu Ser Ser Phe Glu Phe Gly Thr Ser Ala Lys Lys
        290                 295                 300

Tyr Ile Glu Gly Ser Lys Tyr Phe Ile Pro Ala Lys Asp Val Thr Ser
305                 310                 315                 320

Phe Leu Met Ser Tyr Gln Lys Asp Ile Ile Ala Lys Ile Pro Ser Leu
                325                 330                 335

Ser Leu Ala Ile Leu Val Phe Phe Thr Ser Met Ile Phe Phe Val Asn
            340                 345                 350

Asn Leu Thr Ile Val Tyr Asp Ala Leu Tyr Asp Gly Asn His Leu Thr
            355                 360                 365

Tyr Tyr Ile Leu Leu Ala Ile His Thr Ser Ala Cys Leu Leu Leu Leu
    370                 375                 380

Leu Asn Val Val Gly Ile Tyr Lys Gln Ser Arg Arg Ala Ile Ile Phe
385                 390                 395                 400

Ala Met Ile Ser Ile Leu Leu Ile Thr Val Ala Thr Phe Phe Thr Tyr
                405                 410                 415

Ala Ser Tyr Ile Leu Ile Thr Trp Leu Ala Ile Ile Phe Val Leu Leu
            420                 425                 430

Ile Val Ala Phe Arg Arg Ala Arg Arg Leu Lys Arg Pro Val Arg Met
        435                 440                 445

Arg Asn Ile Val Ala Met Leu Leu Phe Ser Leu Phe Ile Leu Tyr Val
    450                 455                 460

Asn His Ile Phe Ile Ala Gly Thr Leu Tyr Ala Leu Asp Ile Tyr Thr
465                 470                 475                 480

Ile Glu Met His Thr Ser Val Leu Arg Tyr Tyr Phe Trp Leu Thr Ile
                485                 490                 495

Leu Ile Ile Ala Ile Ile Gly Met Ile Ala Trp Leu Phe Asp Tyr
            500                 505                 510

Gln Phe Ser Lys Val Arg Ile Ser Ser Lys Ile Glu Asp Cys Glu Glu
        515                 520                 525

Ile Ile Asn Gln Tyr Gly Gly Asn Tyr Leu Ser His Leu Ile Tyr Ser
    530                 535                 540

Gly Asp Lys Gln Phe Phe Thr Asn Glu Asn Lys Thr Ala Phe Leu Met
545                 550                 555                 560

Tyr Arg Tyr Lys Ala Ser Ser Leu Val Val Leu Gly Asp Pro Leu Gly
                565                 570                 575

Asp Glu Asn Ala Phe Asp Glu Leu Leu Glu Ala Phe Tyr Asn Tyr Ala
            580                 585                 590
```

-continued

```
Glu Tyr Leu Gly Tyr Asp Val Ile Phe Tyr Gln Val Thr Asp Gln His
        595                 600                 605

Met Pro Leu Tyr His Asn Phe Gly Asn Gln Phe Phe Lys Leu Gly Glu
        610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655

Phe Glu Ile Ile Glu Pro Pro Phe Ser Thr Glu Phe Ile Asn Glu Leu
                660                 665                 670

Gln His Val Ser Asp Leu Trp Leu Asp Asn Arg Gln Glu Met His Phe
            675                 680                 685

Ser Val Gly Glu Phe Asn Glu Glu Tyr Leu Ser Lys Ala Pro Ile Gly
        690                 695                 700

Val Met Arg Asn Glu Glu Asn Glu Val Ile Ala Phe Cys Ser Leu Met
705                 710                 715                 720

Pro Thr Tyr Phe Asn Asp Ala Ile Ser Val Asp Leu Ile Arg Trp Leu
                725                 730                 735

Pro Glu Leu Asp Leu Pro Leu Met Asp Gly Leu Tyr Leu His Met Leu
            740                 745                 750

Leu Trp Ser Lys Glu Gln Gly Tyr Thr Lys Phe Asn Met Gly Met Ala
        755                 760                 765

Thr Leu Ser Asn Val Gly Gln Leu His Tyr Ser Tyr Leu Arg Glu Arg
770                 775                 780

Leu Ala Gly Arg Val Phe Glu His Phe Asn Gly Leu Tyr Arg Phe Gln
785                 790                 795                 800

Gly Leu Arg Arg Tyr Lys Ser Lys Tyr Asn Pro Asn Trp Glu Pro Arg
                805                 810                 815

Phe Leu Val Tyr Arg Lys Asp Asn Ser Leu Trp Glu Ser Leu Ser Lys
                820                 825                 830

Val Met Arg Val Ile Arg His Lys
        835                 840

<210> SEQ ID NO 2
<211> LENGTH: 19
<212> TYPE: PRT
<213> ORGANISM: Staphylococcus aureus
<220> FEATURE:
<223> OTHER INFORMATION: Loop 1

<400> SEQUENCE: 2

Glu Leu Ser Gly Ile Asn Phe Lys Asp Thr Leu Val Glu Phe Ser Lys
1               5                   10                  15

Ile Asn Arg

<210> SEQ ID NO 3
<211> LENGTH: 14
<212> TYPE: PRT
<213> ORGANISM: Staphylococcus aureus
<220> FEATURE:
<223> OTHER INFORMATION: Loop 2

<400> SEQUENCE: 3

Tyr Lys Asn Tyr Thr His Asp Lys Lys Leu Val His Phe
1               5                   10

<210> SEQ ID NO 4
```

-continued

```
<211> LENGTH: 14
<212> TYPE: PRT
<213> ORGANISM: Staphylococcus aureus
<220> FEATURE:
<223> OTHER INFORMATION: Loop 3

<400> SEQUENCE: 4

Ser Met Val Arg Pro Pro Asp Lys Asn Asn Arg Phe Val Gly
1               5                   10

<210> SEQ ID NO 5
<211> LENGTH: 13
<212> TYPE: PRT
<213> ORGANISM: Staphylococcus aureus
<220> FEATURE:
<223> OTHER INFORMATION: Loop 4

<400> SEQUENCE: 5

Leu Gly Phe Lys Thr Leu Gly Val Pro Glu Glu Lys Val
1               5                   10

<210> SEQ ID NO 6
<211> LENGTH: 10
<212> TYPE: PRT
<213> ORGANISM: Staphylococcus aureus
<220> FEATURE:
<223> OTHER INFORMATION: Loop 5

<400> SEQUENCE: 6

Asp Ala Leu Tyr Asp Gly Asn His Leu Thr
1               5                   10

<210> SEQ ID NO 7
<211> LENGTH: 13
<212> TYPE: PRT
<213> ORGANISM: Staphylococcus aureus
<220> FEATURE:
<223> OTHER INFORMATION: Loop 6

<400> SEQUENCE: 7

Asp Ile Tyr Thr Ile Glu Met His Thr Ser Val Leu Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: ML-1 HCDR1

<400> SEQUENCE: 8

Gly Gly Thr Phe Asn Ser Tyr Ala Ile His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: ML1 HCDR2

<400> SEQUENCE: 9

Gly Ile Ile Pro Ile Phe Gly Ile Ala Asn Tyr Ala Gln Lys Phe Gln
1               5                   10                  15

Gly
```

```
<210> SEQ ID NO 10
<211> LENGTH: 13
<212> TYPE: PRT
<213> ORGANISM: Artificial Sequence
<220> FEATURE:
<223> OTHER INFORMATION: ML1 HCDR3

<400> SEQUENCE: 10

Asp Gln Tyr Thr Tyr Asp Tyr Tyr Arg Ala Phe Asp Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: ML1 LCDR1

<400> SEQUENCE: 11

Arg Ala Ser Gln Ser Val Arg Asp Asn Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: ML1 LCDR2

<400> SEQUENCE: 12

Gly Ala Ser Asn Arg Ala Thr
1               5

<210> SEQ ID NO 13
<211> LENGTH: 9
<212> TYPE: PRT
<213> ORGANISM: Artificial Sequence
<220> FEATURE:
<223> OTHER INFORMATION: ML1 LCDR3

<400> SEQUENCE: 13

Gln Gln Tyr Asp His Ser Pro Arg Thr
1               5

<210> SEQ ID NO 14
<211> LENGTH: 109
<212> TYPE: PRT
<213> ORGANISM: Artificial Sequence
<220> FEATURE:
<223> OTHER INFORMATION: ML1 VL

<400> SEQUENCE: 14

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asp Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp His Ser Pro Arg
                85                  90                  95
```

Thr Phe Gly Gln Gly Thr Lys Val Glu Ile Lys Arg Thr
            100                 105

<210> SEQ ID NO 15
<211> LENGTH: 122
<212> TYPE: PRT
<213> ORGANISM: Artificial Sequence
<220> FEATURE:
<223> OTHER INFORMATION: ML1 VH

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile His Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Thr Tyr Asp Tyr Tyr Arg Ala Phe Asp Tyr Trp
            100                 105                 110

Gly Gln Gly Thr Leu Val Thr Val Ser Ser
        115                 120

<210> SEQ ID NO 16
<211> LENGTH: 327
<212> TYPE: DNA
<213> ORGANISM: Artificial Sequence
<220> FEATURE:
<223> OTHER INFORMATION: ML1 VL

<400> SEQUENCE: 16
gatatcgtgc tgacccagag cccggcgacc ctgagcctga gcccgggtga acgtgccacc      60
ctgagctgca gcgagccag tctgttcgt gacaacctgg cttggtacca gcagaaaccg       120
ggccaggccc cgcgtctatt aatctacggt gcttctaacc gtgcgaccgg cattccggcg     180
cgttttagcg gcagcggatc cggcaccgat ttcaccctga ccattagcag cctgaaaccg     240
gaagactttg cggtgtatta ttgccagcag tacgaccatt ctccgcgtac ctttggccag     300
ggcacgaaag ttgaaattaa acgtacg                                         327

<210> SEQ ID NO 17
<211> LENGTH: 366
<212> TYPE: DNA
<213> ORGANISM: Artificial Sequence
<220> FEATURE:
<223> OTHER INFORMATION: ML1 VH

<400> SEQUENCE: 17
caggtgcaat tggtgcagag cggtgccgaa gtgaaaaaac cgggcagcag cgtgaaagtt      60
agctgcaaag catccggagg gacgtttaac tcttacgcta tccattgggt cgcgcaggcc     120
ccgggccagg gctcgagtg gatgggcggt atcatcccga tcttcggcat cgcgaactac      180
gcccagaaat ttcagggccg ggtgaccatt accgccgatg aaagcaccag caccgcctat     240
atggaactga gcagcctgcg cagcgaagat acggccgtgt attattgcgc gcgtgaccag     300

```
tacacttacg actactaccg tgctttcgat tactggggcc aaggcaccct ggtgactgtt    360
agctca                                                               366
```

```
<210> SEQ ID NO 18
<211> LENGTH: 5
<212> TYPE: PRT
<213> ORGANISM: Artificial Sequence
<220> FEATURE:
<223> OTHER INFORMATION: ML4 HCDR1

<400> SEQUENCE: 18

Ser Tyr Ala Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: ML4 HCDR2

<400> SEQUENCE: 19

Ile Ile Ser Tyr Asp Gly Ser Ser Thr Tyr Tyr Ala Asp Ser Val Lys
1               5                   10                  15

Gly

<210> SEQ ID NO 20
<211> LENGTH: 12
<212> TYPE: PRT
<213> ORGANISM: Artificial Sequence
<220> FEATURE:
<223> OTHER INFORMATION: ML4 HCDR3

<400> SEQUENCE: 20

Thr Ala Thr Ser Gly Ser Arg Gly Tyr Phe Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: ML4 LCDR1

<400> SEQUENCE: 21

Arg Ala Ser Gln Asp Ile Ser Ser Trp Leu Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: ML4 LCDR2

<400> SEQUENCE: 22

Gly Ala Ser Thr Leu Gln Ser
1               5

<210> SEQ ID NO 23
<211> LENGTH: 9
<212> TYPE: PRT
<213> ORGANISM: Artificial Sequence
<220> FEATURE:
<223> OTHER INFORMATION: ML4 LCDR3
```

<400> SEQUENCE: 23

Gln Gln His Tyr Thr Ser Pro Val Thr
1               5

<210> SEQ ID NO 24
<211> LENGTH: 109
<212> TYPE: PRT
<213> ORGANISM: Artificial Sequence
<220> FEATURE:
<223> OTHER INFORMATION: ML4 VL

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Asn Trp Tyr Gln Gln Lys Pro Gly Lys Ala Pro Lys Leu Leu Ile
        35                  40                  45

Phe Gly Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Ser Pro Val
                85                  90                  95

Thr Phe Gly Gln Gly Thr Lys Val Glu Ile Lys Arg Thr
            100                 105

<210> SEQ ID NO 25
<211> LENGTH: 121
<212> TYPE: PRT
<213> ORGANISM: Artificial Sequence
<220> FEATURE:
<223> OTHER INFORMATION: ML4 VH

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ile Ile Ser Tyr Asp Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ala Thr Ser Gly Ser Arg Gly Tyr Phe Asp Tyr Trp Gly
            100                 105                 110

Gln Gly Thr Leu Val Thr Val Ser Ser
        115                 120

<210> SEQ ID NO 26
<211> LENGTH: 327
<212> TYPE: DNA
<213> ORGANISM: Artificial Sequence
<220> FEATURE:
<223> OTHER INFORMATION: ML4 VL

<400> SEQUENCE: 26

```
gatatccaga tgacccagag cccgagcagc ctgagcgcca gcgtgggcga tcgcgtgacc      60
attacctgca gagccagcca ggacatttct tcttggctga actggtacca gcagaaaccg     120
ggcaaagcgc cgaaactatt aatcttcggt gcttctactc tgcaaagcgg cgtgccgagc     180
cgctttagcg gcagcggatc cggcaccgat ttcaccctga ccattagctc tctgcaaccg     240
gaagactttg cgacctatta ttgccagcag cattacactt ctccggttac ctttggccag     300
ggcacgaaag ttgaaattaa acgtacg                                         327
```

<210> SEQ ID NO 27
<211> LENGTH: 363
<212> TYPE: DNA
<213> ORGANISM: Artificial Sequence
<220> FEATURE:
<223> OTHER INFORMATION: ML4 VH

<400> SEQUENCE: 27

```
gaagtgcaat tgctggaaag cggcggtggc ctggtgcagc cgggtggcag cctgcgtctg      60
agctgcgcgg cgtccggatt cacctttcgt tcttacgcta tgtcttgggt gcgccaggcc     120
ccgggcaaag gtctcgagtg gtttccatt atctcttacg acggttcttc tacctactat     180
gcggatagcg tgaaaggccg ctttaccatc agccgcgata attcgaaaaa caccctgtat     240
ctgcaaatga acagcctgcg tgcggaagat acggccgtgt attattgcgc gcgtactgct     300
acttctggtt ctcgtggtta cttcgattac tggggccaag caccctggt gactgttagc     360 tca                                                                   363
```

<210> SEQ ID NO 28
<211> LENGTH: 5
<212> TYPE: PRT
<213> ORGANISM: Artificial Sequence
<220> FEATURE:
<223> OTHER INFORMATION: MC1 HCDR1

<400> SEQUENCE: 28

Ser Tyr Ala Met Asn
1               5

<210> SEQ ID NO 29
<211> LENGTH: 17
<212> TYPE: PRT
<213> ORGANISM: Artificial Sequence
<220> FEATURE:
<223> OTHER INFORMATION: MC1 HCDR2

<400> SEQUENCE: 29

Val Ile Ser Ser Asp Gly Ser Asp Thr Tyr Tyr Ala Asp Ser Val Lys
1               5                   10                  15

Gly

<210> SEQ ID NO 30
<211> LENGTH: 9
<212> TYPE: PRT
<213> ORGANISM: Artificial Sequence
<220> FEATURE:
<223> OTHER INFORMATION: MC1 HCDR3

<400> SEQUENCE: 30

Glu Ser Tyr Tyr Ile Gly Trp Asp Tyr
1               5

```
<210> SEQ ID NO 31
<211> LENGTH: 12
<212> TYPE: PRT
<213> ORGANISM: Artificial Sequence
<220> FEATURE:
<223> OTHER INFORMATION: MC1 LCDR1

<400> SEQUENCE: 31

Arg Ala Ser Gln Arg Val Ser Ser Ser Phe Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: MC1 LCDR2

<400> SEQUENCE: 32

Leu Ala Ser Asn Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: MC1 LCDR3

<400> SEQUENCE: 33

Leu Gln Tyr Gly His Tyr Pro Pro Thr
1               5

<210> SEQ ID NO 34
<211> LENGTH: 110
<212> TYPE: PRT
<213> ORGANISM: Artificial Sequence
<220> FEATURE:
<223> OTHER INFORMATION: MC1 VL

<400> SEQUENCE: 34

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Phe Leu Ala Trp Tyr Gln Gln Lys Pro Gly Gln Ala Pro Arg Leu Leu
            35                  40                  45

Ile Tyr Leu Ala Ser Asn Arg Ala Thr Gly Ile Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Leu Gln Tyr Gly His Tyr Pro
                85                  90                  95

Pro Thr Phe Gly Gln Gly Thr Lys Val Glu Ile Lys Arg Thr
            100                 105                 110

<210> SEQ ID NO 35
<211> LENGTH: 118
<212> TYPE: PRT
<213> ORGANISM: Artificial Sequence
<220> FEATURE:
<223> OTHER INFORMATION: MC1 VH

<400> SEQUENCE: 35
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Val Ile Ser Ser Asp Gly Ser Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Tyr Tyr Ile Gly Trp Asp Tyr Trp Gly Gln Gly Thr
            100                 105                 110

Leu Val Thr Val Ser Ser
        115
```

```
<210> SEQ ID NO 36
<211> LENGTH: 330
<212> TYPE: DNA
<213> ORGANISM: Artificial Sequence
<220> FEATURE:
<223> OTHER INFORMATION: MC1 VL

<400> SEQUENCE: 36
gatatcgtgc tgacccagag cccggcgacc ctgagcctga gcccgggtga acgtgccacc     60
ctgagctgca gcgagcca gcgtgttct tcttctttcc tggcttggta ccagcagaaa       120
ccgggccagg ccccgcgtct attaatctac ctggcttcta accgtgcgac cggcattccg    180
gcgcgtttta gcggcagcgg atccggcacc gatttcaccc tgaccattag cagcctggaa    240
ccggaagact ttgcggtgta ttattgcctg cagtacggtc attcccgcc gacctttggc     300
cagggcacga agttgaaat taaacgtacg                                       330

<210> SEQ ID NO 37
<211> LENGTH: 354
<212> TYPE: DNA
<213> ORGANISM: Artificial Sequence
<220> FEATURE:
<223> OTHER INFORMATION: MC1 VH

<400> SEQUENCE: 37
caggtgcaat tgctggaaag cggcggtggc ctggtgcagc cgggtggcag cctgcgtctg     60
agctgcgcgg cgtccggatt cacctttct tcttacgcta tgaactgggt gcgccaggcc     120
ccgggcaaag gtctcgagtg ggttccgtt atctcttctg acggttctga cacctactat     180
gcggatagcg tgaaaggccg ctttaccatc agccgcgata ttcgaaaaa caccctgtat     240
ctgcaaatga acagcctgcg tgcggaagat acggccgtgt attattgcgc gcgtgaatct    300
tactacatcg gttgggatta ctggggccaa ggcacccctgg tgactgttag ctca         354

<210> SEQ ID NO 38
<211> LENGTH: 5
<212> TYPE: PRT
<213> ORGANISM: Artificial Sequence
<220> FEATURE:
<223> OTHER INFORMATION: MC41 HCDR1

<400> SEQUENCE: 38

Ser Tyr Ala Ile Ser
```

<210> SEQ ID NO 39
<211> LENGTH: 17
<212> TYPE: PRT
<213> ORGANISM: Artificial Sequence
<220> FEATURE:
<223> OTHER INFORMATION: MC41 HCDR2

<400> SEQUENCE: 39

Gly Ile Ile Pro Ile Phe Gly Met Ala Thr Tyr Ala Gln Lys Phe Gln
1               5                   10                  15
Gly

<210> SEQ ID NO 40
<211> LENGTH: 7
<212> TYPE: PRT
<213> ORGANISM: Artificial Sequence
<220> FEATURE:
<223> OTHER INFORMATION: MC41 HCDR3

<400> SEQUENCE: 40

Ser Leu Phe Gly Arg Ala Tyr
1               5

<210> SEQ ID NO 41
<211> LENGTH: 11
<212> TYPE: PRT
<213> ORGANISM: Artificial Sequence
<220> FEATURE:
<223> OTHER INFORMATION: MC41 LCDR1

<400> SEQUENCE: 41

Arg Ala Ser Gln Ser Ile Ser Ser Phe Leu Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: MC41 LCDR2

<400> SEQUENCE: 42

Asp Ala Ser Ser Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: MC41 LCDR3

<400> SEQUENCE: 43

Leu Gln Ala Asp Ser Thr Ser Tyr Thr
1               5

<210> SEQ ID NO 44
<211> LENGTH: 109
<212> TYPE: PRT
<213> ORGANISM: Artificial Sequence
<220> FEATURE:
<223> OTHER INFORMATION: MC41 VL

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ala Asp Ser Thr Ser Tyr
                85                  90                  95

Thr Phe Gly Gln Gly Thr Lys Val Glu Ile Lys Arg Thr
            100                 105

<210> SEQ ID NO 45
<211> LENGTH: 116
<212> TYPE: PRT
<213> ORGANISM: Artificial Sequence
<220> FEATURE:
<223> OTHER INFORMATION: MC41 VH

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Met Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Phe Gly Arg Ala Tyr Trp Gly Gln Gly Thr Leu Val
            100                 105                 110

Thr Val Ser Ser
        115

<210> SEQ ID NO 46
<211> LENGTH: 327
<212> TYPE: DNA
<213> ORGANISM: Artificial Sequence
<220> FEATURE:
<223> OTHER INFORMATION: MC41 VL

<400> SEQUENCE: 46
gatatccaga tgacccagag cccgagcagc ctgagcgcca gcgtgggcga tcgcgtgacc     60
attacctgca gagccagcca gtctatttct tctttcctgg cttggtacca gcagaaaccg    120
ggcaaagcgc cgaaactatt aatctacgac gcttcttctc tgcaaagcgg cgtgccgagc    180
cgctttagcg gcagcggatc cggcaccgat ttcaccctga ccattagctc tctgcaaccg    240
gaagactttg cgacctatta ttgcctgcag gctgactcta cttcttacac ctttggccag    300
ggcacgaaag ttgaaattaa acgtacg                                        327

<210> SEQ ID NO 47
```

<211> LENGTH: 348
<212> TYPE: DNA
<213> ORGANISM: Artificial Sequence
<220> FEATURE:
<223> OTHER INFORMATION: MC41 VH

<400> SEQUENCE: 47

```
caggtgcaat tggtgcagag cggtgccgaa gtgaaaaaac cgggcagcag cgtgaaagtt    60
agctgcaaag catccggagg gacgtttaac tcttacgcta tctcttgggt gcgccaggcc   120
ccgggccagg gcctcgagtg gatgggcggt atcatcccga tcttcggcat ggcgacttac   180
gcccagaaat ttcagggccg ggtgaccatt accgccgatg aaagcaccag caccgcctat   240
atggaactga gcagcctgcg cagcgaagat acggccgtgt attattgcgc gcgttctctg   300
ttcggtcgtg cttactgggg ccaaggcacc ctggtgactg ttagctca              348
```

<210> SEQ ID NO 48
<211> LENGTH: 5
<212> TYPE: PRT
<213> ORGANISM: Artificial Sequence
<220> FEATURE:
<223> OTHER INFORMATION: MC42 HCDR1

<400> SEQUENCE: 48

Ser Tyr Ala Met His
1               5

<210> SEQ ID NO 49
<211> LENGTH: 17
<212> TYPE: PRT
<213> ORGANISM: Artificial Sequence
<220> FEATURE:
<223> OTHER INFORMATION: MC42 HCDR2

<400> SEQUENCE: 49

Val Ile Ser Ser Val Gly Ser Ser Thr Tyr Tyr Ala Asp Ser Val Lys
1               5                   10                  15

Gly

<210> SEQ ID NO 50
<211> LENGTH: 5
<212> TYPE: PRT
<213> ORGANISM: Artificial Sequence
<220> FEATURE:
<223> OTHER INFORMATION: MC42 HCDR3

<400> SEQUENCE: 50

Gly Gly Leu Asp Val
1               5

<210> SEQ ID NO 51
<211> LENGTH: 11
<212> TYPE: PRT
<213> ORGANISM: Artificial Sequence
<220> FEATURE:
<223> OTHER INFORMATION: MC42 LCDR1

<400> SEQUENCE: 51

Arg Ala Ser Gln Asp Ile Ser Lys Tyr Leu Asn
1               5                   10

<210> SEQ ID NO 52
<211> LENGTH: 7
<212> TYPE: PRT
<213> ORGANISM: Artificial Sequence

```
<220> FEATURE:
<223> OTHER INFORMATION: MC42 LCDR2

<400> SEQUENCE: 52

Ala Ala Ser Arg Leu Gln Ser
1               5

<210> SEQ ID NO 53
<211> LENGTH: 9
<212> TYPE: PRT
<213> ORGANISM: Artificial Sequence
<220> FEATURE:
<223> OTHER INFORMATION: MC42 LCDR3

<400> SEQUENCE: 53

Gln Gln Gly Asp Ser Thr Pro Phe Thr
1               5

<210> SEQ ID NO 54
<211> LENGTH: 109
<212> TYPE: PRT
<213> ORGANISM: Artificial Sequence
<220> FEATURE:
<223> OTHER INFORMATION: MC42 VL

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Thr Pro Phe
                85                  90                  95

Thr Phe Gly Gln Gly Thr Lys Val Glu Ile Lys Arg Thr
            100                 105

<210> SEQ ID NO 55
<211> LENGTH: 114
<212> TYPE: PRT
<213> ORGANISM: Artificial Sequence
<220> FEATURE:
<223> OTHER INFORMATION: MC42 VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Val Ile Ser Ser Val Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Gly Leu Asp Val Trp Gly Gln Gly Thr Leu Val Thr Val
            100                 105                 110

Ser Ser

<210> SEQ ID NO 56
<211> LENGTH: 327
<212> TYPE: DNA
<213> ORGANISM: Artificial Sequence
<220> FEATURE:
<223> OTHER INFORMATION: MC42 VL

<400> SEQUENCE: 56
gatatccaga tgacccagag cccgagcagc ctgagcgcca gcgtgggcga tcgcgtgacc    60
attacctgca gagccagcca ggacatttct aaatacctga actggtacca gcagaaaccg   120
ggcaaagcgc cgaaactatt aatctacgct gcttctcgtc tgcaaagcgg cgtgccgagc   180
cgctttagcg gcagcggatc cggcaccgat tcaccctga ccattagctc tctgcaaccg    240
gaagactttg cgacctatta ttgccagcag ggtgactcta ctccgttcac ctttggccag   300
ggcacgaaag ttgaaattaa acgtacg                                       327

<210> SEQ ID NO 57
<211> LENGTH: 342
<212> TYPE: DNA
<213> ORGANISM: Artificial Sequence
<220> FEATURE:
<223> OTHER INFORMATION: MC42 VH

<400> SEQUENCE: 57
gaagtgcaat tgctggaaag cggcggtggc ctggtgcagc cgggtggcag cctgcgtctg    60
agctgcgcgg cgtccggatt cacctttttct tcttacgcta tgcattgggt cgcgcaggcc   120
ccgggcaaag gtctcgagtg gtttccgtt atctcttctg ttggttcttc tacctactat    180
gcggatagcg tgaaaggccg ctttaccatc agccgcgata ttcgaaaaaa caccctgtat   240
ctgcaaatga acagcctgcg tgcggaagat acggccgtgt attattgcgc gcgtggtggt   300
ctggacgttt ggggccaagg caccctggtg actgttagct ca                     342

<210> SEQ ID NO 58
<211> LENGTH: 5
<212> TYPE: PRT
<213> ORGANISM: Artificial Sequence
<220> FEATURE:
<223> OTHER INFORMATION: MC43 HCDR1

<400> SEQUENCE: 58

Asp His Thr Ile Ser
1               5

<210> SEQ ID NO 59
<211> LENGTH: 17
<212> TYPE: PRT
<213> ORGANISM: Artificial Sequence
<220> FEATURE:
<223> OTHER INFORMATION: MC43 HCDR2

<400> SEQUENCE: 59

Gly Ile Ile Pro Ile Val Gly Ile Ala Asn Tyr Ala Gln Lys Phe Gln
1               5                   10                  15

Gly

```
<210> SEQ ID NO 60
<211> LENGTH: 12
<212> TYPE: PRT
<213> ORGANISM: Artificial Sequence
<220> FEATURE:
<223> OTHER INFORMATION: MC43 HCDR3

<400> SEQUENCE: 60

Glu Tyr Tyr Val Pro Asp Ser Gly Trp Phe Asp Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: MC43 LCDR1

<400> SEQUENCE: 61

Arg Ala Ser Gln Asp Ile Ser Asp Tyr Leu Val
1               5                   10

<210> SEQ ID NO 62
<211> LENGTH: 7
<212> TYPE: PRT
<213> ORGANISM: Artificial Sequence
<220> FEATURE:
<223> OTHER INFORMATION: MC43 LCDR2

<400> SEQUENCE: 62

Asp Ala Ser Asn Leu Gln Ser
1               5

<210> SEQ ID NO 63
<211> LENGTH: 8
<212> TYPE: PRT
<213> ORGANISM: Artificial Sequence
<220> FEATURE:
<223> OTHER INFORMATION: MC43 LCDR3

<400> SEQUENCE: 63

Gln Gln Tyr Tyr His Tyr Arg Thr
1               5

<210> SEQ ID NO 64
<211> LENGTH: 108
<212> TYPE: PRT
<213> ORGANISM: Artificial Sequence
<220> FEATURE:
<223> OTHER INFORMATION: MC43 VL

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Val Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr His Tyr Arg Thr
                85                  90                  95
```

```
Phe Gly Gln Gly Thr Lys Val Glu Ile Lys Arg Thr
            100                 105
```

<210> SEQ ID NO 65
<211> LENGTH: 121
<212> TYPE: PRT
<213> ORGANISM: Artificial Sequence
<220> FEATURE:
<223> OTHER INFORMATION: MC43 VH

<400> SEQUENCE: 65

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asp His
            20                  25                  30
Thr Ile Ser Trp Val Arg Gln Ala Pro Gly Gln Gly Leu Glu Trp Met
        35                  40                  45
Gly Gly Ile Ile Pro Ile Val Gly Ile Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Val Pro Asp Ser Gly Trp Phe Asp Tyr Trp Gly
            100                 105                 110
Gln Gly Thr Leu Val Thr Val Ser Ser
        115                 120
```

<210> SEQ ID NO 66
<211> LENGTH: 324
<212> TYPE: DNA
<213> ORGANISM: Artificial Sequence
<220> FEATURE:
<223> OTHER INFORMATION: MC43 VL

<400> SEQUENCE: 66

```
gatatccaga tgacccagag cccgagcagc ctgagcgcca gcgtgggcga tcgcgtgacc      60
attacctgca gagccagcca ggacatttct gactacctgg tttggtacca gcagaaaccg     120
ggcaaagcgc cgaaactatt aatctacgac gcttctaacc tgcaaagcgg cgtgccgagc     180
cgctttagcg gcagcggatc cggcaccgat ttcaccctga ccattagctc tctgcaaccg     240
gaagactttg cgacctatta ttgccagcag tactaccatt accgtacctt ggccagggc      300
acgaaagttg aaattaaacg tacg                                            324
```

<210> SEQ ID NO 67
<211> LENGTH: 363
<212> TYPE: DNA
<213> ORGANISM: Artificial Sequence
<220> FEATURE:
<223> OTHER INFORMATION: MC43 VH

<400> SEQUENCE: 67

```
caggtgcaat tggtgcagag cggtgccgaa gtgaaaaaac cgggcagcag cgtgaaagtt      60
agctgcaaag catccggagg gacgttttct gaccacacta tctcttgggt gcgccaggcc     120
ccgggccagg gcctcgagtg gatgggcggt atcatcccga tcgttggcat cgcgaactac     180
gcccagaaat ttcagggccg ggtgaccatt accgccgatg aaagcaccag caccgcctat     240
atggaactga gcagcctgcg cagcgaagat acggccgtgt attattgcgc gcgtgaatac     300
```

```
tacgttccgg actctggttg gttcgattac tggggccaag gcaccctggt gactgttagc    360
tca                                                                  363
```

<210> SEQ ID NO 68
<211> LENGTH: 5
<212> TYPE: PRT
<213> ORGANISM: Artificial Sequence
<220> FEATURE:
<223> OTHER INFORMATION: MC51 HCDR1

<400> SEQUENCE: 68

Ser Tyr Ala Ile Ser
1               5

<210> SEQ ID NO 69
<211> LENGTH: 17
<212> TYPE: PRT
<213> ORGANISM: Artificial Sequence
<220> FEATURE:
<223> OTHER INFORMATION: MC51 HCDR2

<400> SEQUENCE: 69

Gly Ile Val Pro Ile Phe Gly Thr Ala Asn Tyr Ala Gln Lys Phe Gln
1               5                   10                  15

Gly

<210> SEQ ID NO 70
<211> LENGTH: 8
<212> TYPE: PRT
<213> ORGANISM: Artificial Sequence
<220> FEATURE:
<223> OTHER INFORMATION: MC51 HCDR3

<400> SEQUENCE: 70

Val Arg Tyr Gly Tyr Trp Asp Val
1               5

<210> SEQ ID NO 71
<211> LENGTH: 11
<212> TYPE: PRT
<213> ORGANISM: Artificial Sequence
<220> FEATURE:
<223> OTHER INFORMATION: MC51 LCDR1

<400> SEQUENCE: 71

Arg Ala Ser Gln Asp Ile Ala Asn Trp Leu Asn
1               5                   10

<210> SEQ ID NO 72
<211> LENGTH: 7
<212> TYPE: PRT
<213> ORGANISM: Artificial Sequence
<220> FEATURE:
<223> OTHER INFORMATION: MC51 LCDR2

<400> SEQUENCE: 72

Ala Ala Ser Ser Leu Gln Ser
1               5

<210> SEQ ID NO 73
<211> LENGTH: 9
<212> TYPE: PRT
<213> ORGANISM: Artificial Sequence
<220> FEATURE:
<223> OTHER INFORMATION: MC51 LCDR3

```
<400> SEQUENCE: 73

Gln Gln Tyr Ile Ser Leu Pro Ile Thr
1               5

<210> SEQ ID NO 74
<211> LENGTH: 109
<212> TYPE: PRT
<213> ORGANISM: Artificial Sequence
<220> FEATURE:
<223> OTHER INFORMATION: MC51 VL

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Asn Trp
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Ser Leu Pro Ile
                85                  90                  95

Thr Phe Gly Gln Gly Thr Lys Val Glu Ile Lys Arg Thr
            100                 105

<210> SEQ ID NO 75
<211> LENGTH: 117
<212> TYPE: PRT
<213> ORGANISM: Artificial Sequence
<220> FEATURE:
<223> OTHER INFORMATION: MC51 VH

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Val Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Tyr Gly Tyr Trp Asp Val Trp Gly Gln Gly Thr Leu
            100                 105                 110

Val Thr Val Ser Ser
        115

<210> SEQ ID NO 76
<211> LENGTH: 327
<212> TYPE: DNA
<213> ORGANISM: Artificial Sequence
<220> FEATURE:
<223> OTHER INFORMATION: MC51 VL

<400> SEQUENCE: 76
```

```
gatatccaga tgacccagag cccgagcagc tgagcgcca gcgtgggcga tcgcgtgacc    60
attacctgca gagccagcca ggacattgct aactggctga actggtacca gcagaaaccg   120
ggcaaagcgc cgaaactatt aatctacgct gcttcttctc tgcaaagcgg cgtgccgagc   180
cgctttagcg gcagcggatc cggcaccgat tcacccctga ccattagctc tctgcaaccg   240
gaagactttg cgacctatta ttgccagcag tacatctctc tgccgatcac ctttggccag   300
ggcacgaaag ttgaaattaa acgtacg                                        327
```

<210> SEQ ID NO 77
<211> LENGTH: 351
<212> TYPE: DNA
<213> ORGANISM: Artificial Sequence
<220> FEATURE:
<223> OTHER INFORMATION: MC51 VH

<400> SEQUENCE: 77

```
caggtgcaat tggtgcagag cggtgccgaa gtgaaaaaac cgggcagcag cgtgaaagtt    60
agctgcaaag catccggagg gacgtttttct tcttacgcta tctcttgggt gcgccaggcc   120 ccggccagg gcctcgagtg gatgggcggt atcgttccga tcttcggcac tgcgaactac    180
gcccagaaat ttcagggccg ggtgaccatt accgccgatg aaagcaccag caccgcctat   240
atggaactga gcagcctgcg cagcgaagat acggccgtgt attattgcgc gcgtgttcgt   300
tacggctact gggatgtttg gggccaaggc accctggtga ctgttagctc a            351
```

<210> SEQ ID NO 78
<211> LENGTH: 5
<212> TYPE: PRT
<213> ORGANISM: Artificial Sequence
<220> FEATURE:
<223> OTHER INFORMATION: MC52 HCDR1

<400> SEQUENCE: 78

Ser Tyr Ala Val His
1               5

<210> SEQ ID NO 79
<211> LENGTH: 17
<212> TYPE: PRT
<213> ORGANISM: Artificial Sequence
<220> FEATURE:
<223> OTHER INFORMATION: MC52 HCDR2

<400> SEQUENCE: 79

Val Ile Ser Gly Arg Gly Gly Ser Thr Tyr Tyr Ala Asp Ser Val Lys
1               5                   10                  15
Gly

<210> SEQ ID NO 80
<211> LENGTH: 7
<212> TYPE: PRT
<213> ORGANISM: Artificial Sequence
<220> FEATURE:
<223> OTHER INFORMATION: MC52 HCDR3

<400> SEQUENCE: 80

Asp His Gly Tyr Phe Asp Tyr
1               5

<210> SEQ ID NO 81
<211> LENGTH: 11

```
<212> TYPE: PRT
<213> ORGANISM: Artificial Sequence
<220> FEATURE:
<223> OTHER INFORMATION: MC52 LCDR1

<400> SEQUENCE: 81

Arg Ala Ser Gln Thr Ile Ser Asn His Leu Gly
1               5                   10

<210> SEQ ID NO 82
<211> LENGTH: 7
<212> TYPE: PRT
<213> ORGANISM: Artificial Sequence
<220> FEATURE:
<223> OTHER INFORMATION: MC52 LCDR2

<400> SEQUENCE: 82

Thr Ala Ser Asn Leu Gln Ser
1               5

<210> SEQ ID NO 83
<211> LENGTH: 9
<212> TYPE: PRT
<213> ORGANISM: Artificial Sequence
<220> FEATURE:
<223> OTHER INFORMATION: MC52 LCDR3

<400> SEQUENCE: 83

Gln Gln Tyr Ser His Ser Ser Tyr Thr
1               5

<210> SEQ ID NO 84
<211> LENGTH: 109
<212> TYPE: PRT
<213> ORGANISM: Artificial Sequence
<220> FEATURE:
<223> OTHER INFORMATION: MC52 VL

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn His
            20                  25                  30

Leu Gly Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser His Ser Ser Tyr
                85                  90                  95

Thr Phe Gly Gln Gly Thr Lys Val Glu Ile Lys Arg Thr
            100                 105

<210> SEQ ID NO 85
<211> LENGTH: 116
<212> TYPE: PRT
<213> ORGANISM: Artificial Sequence
<220> FEATURE:
<223> OTHER INFORMATION: MC52 VH

<400> SEQUENCE: 85

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
         20                  25                  30

Ala Val His Trp Val Arg Gln Ala Pro Gly Lys Gly Leu Glu Trp Val
         35                  40                  45

Ser Val Ile Ser Gly Arg Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp His Gly Tyr Phe Asp Tyr Trp Gly Gln Gly Thr Leu Val
             100                 105                 110

Thr Val Ser Ser
        115

<210> SEQ ID NO 86
<211> LENGTH: 327
<212> TYPE: DNA
<213> ORGANISM: Artificial Sequence
<220> FEATURE:
<223> OTHER INFORMATION: MC52 VL

<400> SEQUENCE: 86
gatatccaga tgacccagag cccgagcagc ctgagcgcca gcgtgggcga tcgcgtgacc      60
attacctgca gagccagcca gactatttct aaccatctgg gttggtacca gcagaaaccg     120
ggcaaagcgc cgaaactatt aatctacact gcttctaacc tgcaaagcgg cgtgccgagc     180
cgctttagcg gcagcggatc cggcaccgat tcacccctga ccattagctc tctgcaaccg     240
gaagactttg cgacctatta ttgccagcag tactctcatt cttcttacac ctttggccag     300
ggcacgaaag ttgaaattaa acgtacg                                         327

<210> SEQ ID NO 87
<211> LENGTH: 348
<212> TYPE: DNA
<213> ORGANISM: Artificial Sequence
<220> FEATURE:
<223> OTHER INFORMATION: MC52 VH

<400> SEQUENCE: 87
gaagtgcaat tgctggaaag cggcggtggc ctggtgcagc cgggtggcag cctgcgtctg      60
agctgcgcgg cgtccggatt caccttttct tcttacgctg ttcattgggt cgcgcaggcc     120
ccgggcaaag gtctcgagtg ggtttccgtt atctctggtc gtggtggttc tacctactat     180
gcggatagcg tgaaaggccg ctttaccatc agccgcgata attcgaaaaa cacccctgtat    240 ctgcaaatga acagcctgcg tgcggaagat acggccgtgt attattgcgc gcgtgaccat     300
ggttacttcg actactgggg ccaaggcacc ctggtgactg ttagctca                  348

<210> SEQ ID NO 88
<211> LENGTH: 5
<212> TYPE: PRT
<213> ORGANISM: Artificial Sequence
<220> FEATURE:
<223> OTHER INFORMATION: MC61 HCDR1

<400> SEQUENCE: 88

Ile Tyr Ala Ile Ser
 1               5

```
<210> SEQ ID NO 89
<211> LENGTH: 17
<212> TYPE: PRT
<213> ORGANISM: Artificial Sequence
<220> FEATURE:
<223> OTHER INFORMATION: MC61 HCDR2

<400> SEQUENCE: 89

Gly Ile Ile Pro Glu Phe Gly Thr Ala Asn Tyr Ala Gln Lys Phe Gln
1               5                   10                  15
Gly

<210> SEQ ID NO 90
<211> LENGTH: 14
<212> TYPE: PRT
<213> ORGANISM: Artificial Sequence
<220> FEATURE:
<223> OTHER INFORMATION: MC61 HCDR3

<400> SEQUENCE: 90

Ser Gln Ile Tyr Thr Leu Ser Tyr Pro Lys Trp Phe Asp Phe
1               5                   10

<210> SEQ ID NO 91
<211> LENGTH: 11
<212> TYPE: PRT
<213> ORGANISM: Artificial Sequence
<220> FEATURE:
<223> OTHER INFORMATION: MC61 LCDR1

<400> SEQUENCE: 91

Arg Ala Ser Gln Asp Ile Ser Asn Tyr Leu Asn
1               5                   10

<210> SEQ ID NO 92
<211> LENGTH: 7
<212> TYPE: PRT
<213> ORGANISM: Artificial Sequence
<220> FEATURE:
<223> OTHER INFORMATION: MC61 LCDR2

<400> SEQUENCE: 92

Asp Ala Ser Asn Leu Gln Ser
1               5

<210> SEQ ID NO 93
<211> LENGTH: 9
<212> TYPE: PRT
<213> ORGANISM: Artificial Sequence
<220> FEATURE:
<223> OTHER INFORMATION: MC61 LCDR3

<400> SEQUENCE: 93

Leu Gln Tyr Leu Gln Ser Pro Lys Thr
1               5

<210> SEQ ID NO 94
<211> LENGTH: 109
<212> TYPE: PRT
<213> ORGANISM: Artificial Sequence
<220> FEATURE:
<223> OTHER INFORMATION: MC61 VL

<400> SEQUENCE: 94

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
         35                  40                  45

Tyr Asp Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Leu Gln Ser Pro Lys
                 85                  90                  95

Thr Phe Gly Gln Gly Thr Lys Val Glu Ile Lys Arg Thr
            100                 105

<210> SEQ ID NO 95
<211> LENGTH: 123
<212> TYPE: PRT
<213> ORGANISM: Artificial Sequence
<220> FEATURE:
<223> OTHER INFORMATION: MC61 VH

<400> SEQUENCE: 95

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Ala Ile Ser Trp Val Arg Gln Ala Pro Gly Gln Gly Leu Glu Trp Met
         35                  40                  45

Gly Gly Ile Ile Pro Glu Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gln Ile Tyr Thr Leu Ser Tyr Pro Lys Trp Phe Asp Phe
            100                 105                 110

Trp Gly Gln Gly Thr Leu Val Thr Val Ser Ser
            115                 120

<210> SEQ ID NO 96
<211> LENGTH: 327
<212> TYPE: DNA
<213> ORGANISM: Artificial Sequence
<220> FEATURE:
<223> OTHER INFORMATION: MC61 VL

<400> SEQUENCE: 96
gatatccaga tgacccagag cccgagcagc ctgagcgcca gcgtgggcga tcgcgtgacc      60
attacctgca gagccagcca ggacatttct aactacctga actggtacca gcagaaaccg     120
ggcaaagcgc cgaaactatt aatctacgac gcttctaacc tgcaaagcgg cgtgccgagc     180
cgctttagcg gcagcggatc cggcaccgat ttcaccctga ccattagctc tctgcaaccg     240
gaagactttg cgacctatta ttgcctgcag tacctgcagt ctccgaaaac ctttggccag     300
ggcacgaaag ttgaaattaa acgtacg                                         327

<210> SEQ ID NO 97
<211> LENGTH: 369
<212> TYPE: DNA

<213> ORGANISM: Artificial Sequence
<220> FEATURE:
<223> OTHER INFORMATION: MC61 VH

<400> SEQUENCE: 97

```
caggtgcaat tggtgcagag cggtgccgaa gtgaaaaaac cgggcagcag cgtgaaagtt    60
agctgcaaag catccggagg gacgtttttct atctacgcta tctcttgggt gcgccaggcc   120
ccgggccagg gcctcgagtg gatgggcggt atcatcccgg aattcggcac tgcgaactac   180
gcccagaaat tcagggccg gtgaccatt accgccgatg aaagcaccag caccgcctat    240
atggaactga gcagcctgcg cagcgaagat acggccgtgt attattgcgc gcgttctcag   300
atctacactc tgtcttaccc gaaatggttc gacttctggg gccaaggcac cctggtgact   360
gttagctca                                                             369
```

<210> SEQ ID NO 98
<211> LENGTH: 5
<212> TYPE: PRT
<213> ORGANISM: Artificial Sequence
<220> FEATURE:
<223> OTHER INFORMATION: MC62 HCDR1

<400> SEQUENCE: 98

Ser Tyr Ala Ile Ser
1               5

<210> SEQ ID NO 99
<211> LENGTH: 17
<212> TYPE: PRT
<213> ORGANISM: Artificial Sequence
<220> FEATURE:
<223> OTHER INFORMATION: MC62 HCDR2

<400> SEQUENCE: 99

Gly Ile Ile Pro Ile Leu Gly Ile Ala Asn Tyr Ala Gln Lys Phe Gln
1               5                   10                  15

Gly

<210> SEQ ID NO 100
<211> LENGTH: 23
<212> TYPE: PRT
<213> ORGANISM: Artificial Sequence
<220> FEATURE:
<223> OTHER INFORMATION: MC62 HCDR3

<400> SEQUENCE: 100

Ser Leu Pro Tyr Arg Ser Asp Leu Tyr Gly Phe Ser Arg Trp Ser Tyr
1               5                   10                  15

His Arg Val Gly Met Asp Val
            20

<210> SEQ ID NO 101
<211> LENGTH: 11
<212> TYPE: PRT
<213> ORGANISM: Artificial Sequence
<220> FEATURE:
<223> OTHER INFORMATION: MC62 LCDR1

<400> SEQUENCE: 101

Arg Ala Ser Gln Asp Ile Ser Asn Thr Leu Asn
1               5                   10

<210> SEQ ID NO 102

```
<211> LENGTH: 7
<212> TYPE: PRT
<213> ORGANISM: Artificial Sequence
<220> FEATURE:
<223> OTHER INFORMATION: MC62 LCDR2

<400> SEQUENCE: 102

Ala Ala Ser Thr Leu Gln Ser
1               5

<210> SEQ ID NO 103
<211> LENGTH: 9
<212> TYPE: PRT
<213> ORGANISM: Artificial Sequence
<220> FEATURE:
<223> OTHER INFORMATION: MC62 LCDR3

<400> SEQUENCE: 103

Gln Gln Val Gly Ser Phe Pro Tyr Thr
1               5

<210> SEQ ID NO 104
<211> LENGTH: 109
<212> TYPE: PRT
<213> ORGANISM: Artificial Sequence
<220> FEATURE:
<223> OTHER INFORMATION: MC62 VL

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Thr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Gly Ser Phe Pro Tyr
                85                  90                  95

Thr Phe Gly Gln Gly Thr Lys Val Glu Ile Lys Arg Thr
            100                 105

<210> SEQ ID NO 105
<211> LENGTH: 132
<212> TYPE: PRT
<213> ORGANISM: Artificial Sequence
<220> FEATURE:
<223> OTHER INFORMATION: MC62 VH

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Ser Leu Pro Tyr Arg Ser Asp Leu Tyr Gly Phe Ser Arg Trp
            100                 105                 110

Ser Tyr His Arg Val Gly Met Asp Val Trp Gly Gln Gly Thr Leu Val
        115                 120                 125

Thr Val Ser Ser
        130

<210> SEQ ID NO 106
<211> LENGTH: 327
<212> TYPE: DNA
<213> ORGANISM: Artificial Sequence
<220> FEATURE:
<223> OTHER INFORMATION: MC62 VL

<400> SEQUENCE: 106
gatatccaga tgacccagag cccgagcagc ctgagcgcca gcgtgggcga tcgcgtgacc        60
attacctgca gagccagcca ggacatttct aacactctga actggtacca gcagaaaccg       120
ggcaaagcgc cgaaactatt aatctacgct gcttctactc tgcaaagcgg cgtgccgagc       180
cgctttagcg gcagcggatc cggcaccgat ttcaccctga ccattagctc tctgcaaccg       240
gaagactttg cgacctatta ttgccagcag gttggttctt tcccgtacac ctttggccag       300
ggcacgaaag ttgaaattaa acgtacg                                           327

<210> SEQ ID NO 107
<211> LENGTH: 396
<212> TYPE: DNA
<213> ORGANISM: Artificial Sequence
<220> FEATURE:
<223> OTHER INFORMATION: MC62 VH

<400> SEQUENCE: 107
caggtgcaat tggtgcagag cggtgccgaa gtgaaaaaac cgggcagcag cgtgaaagtt        60
agctgcaaag catccggagg gacgttttct tcttacgcta tctcttgggt gcgccaggcc       120
ccgggccagg gcctcgagtg gatgggcggt atcatcccga tcctgggcat cgcgaactac       180
gcccagaaat ttcagggccg ggtgaccatt accgccgatg aaagcaccag caccgcctat       240
atggaactga gcagcctgcg cagcgaagat acggccgtgt attattgcgc gcgttctctg       300
ccgtaccgtt ctgacctgta cggttttctct cgttggtctt accatcgtgt tggtatggat       360
gtttggggcc aaggcaccct ggtgactgtt agctca                                 396

<210> SEQ ID NO 108
<211> LENGTH: 20
<212> TYPE: PRT
<213> ORGANISM: Artificial Sequence
<220> FEATURE:
<223> OTHER INFORMATION: Pep1

<400> SEQUENCE: 108

Cys Glu Leu Ser Gly Ile Asn Phe Lys Asp Thr Leu Val Glu Phe Ser
1               5                   10                  15

Lys Ile Asn Arg
            20

<210> SEQ ID NO 109
<211> LENGTH: 15
<212> TYPE: PRT
```

```
<213> ORGANISM: Artificial Sequence
<220> FEATURE:
<223> OTHER INFORMATION: Pep2

<400> SEQUENCE: 109

Cys Tyr Lys Asn Tyr Thr His Asp Lys Lys Leu Val His Phe
1               5                  10                  15

<210> SEQ ID NO 110
<211> LENGTH: 15
<212> TYPE: PRT
<213> ORGANISM: Artificial Sequence
<220> FEATURE:
<223> OTHER INFORMATION: Pep3

<400> SEQUENCE: 110

Cys Ser Met Val Arg Pro Pro Asp Lys Asn Asn Arg Phe Val Gly
1               5                  10                  15

<210> SEQ ID NO 111
<211> LENGTH: 15
<212> TYPE: PRT
<213> ORGANISM: Artificial Sequence
<220> FEATURE:
<223> OTHER INFORMATION: Pep4

<400> SEQUENCE: 111

Cys Gly Leu Gly Phe Lys Thr Leu Gly Val Pro Glu Glu Lys Val
1               5                  10                  15

<210> SEQ ID NO 112
<211> LENGTH: 13
<212> TYPE: PRT
<213> ORGANISM: Artificial Sequence
<220> FEATURE:
<223> OTHER INFORMATION: Pep5

<400> SEQUENCE: 112

Cys Gly Gly Asp Ala Leu Tyr Asp Gly Asn His Leu Thr
1               5                  10

<210> SEQ ID NO 113
<211> LENGTH: 14
<212> TYPE: PRT
<213> ORGANISM: Artificial Sequence
<220> FEATURE:
<223> OTHER INFORMATION: Pep6

<400> SEQUENCE: 113

Cys Asp Ile Tyr Thr Ile Glu Met His Thr Ser Val Leu Arg
1               5                  10

<210> SEQ ID NO 114
<211> LENGTH: 840
<212> TYPE: PRT
<213> ORGANISM: Staphylococcus aureus
<220> FEATURE:
<223> OTHER INFORMATION: MRSA252

<400> SEQUENCE: 114

Met Asn Gln Glu Val Lys Asn Lys Ile Phe Ser Ile Leu Lys Ile Thr
1               5                  10                  15

Phe Ala Thr Ala Leu Phe Ile Phe Val Val Ile Thr Leu Tyr Arg Glu
                20                  25                  30

Leu Ser Gly Ile Asn Phe Lys Asp Thr Leu Val Glu Phe Ser Lys Ile
            35                  40                  45
```

```
Asn Arg Met Ser Leu Val Leu Leu Phe Ile Gly Gly Ala Ser Leu
         50                  55                  60
Val Ile Leu Ser Met Tyr Asp Val Ile Leu Ser Arg Ala Leu Lys Met
 65                  70                  75                  80
Asp Ile Ser Leu Gly Lys Val Leu Arg Val Ser Tyr Ile Ile Asn Ala
                 85                  90                  95
Leu Asn Ala Ile Val Gly Phe Gly Phe Ile Gly Ala Gly Val Arg
                100                 105                 110
Ala Met Val Tyr Lys Asn Tyr Thr His Asp Lys Lys Leu Val His
         115                 120                 125
Phe Ile Ser Leu Ile Leu Ile Ser Met Leu Thr Gly Leu Ser Leu Leu
 130                 135                 140
Ser Leu Leu Ile Val Phe His Val Phe Asp Ala Ser Leu Ile Leu Asn
145                 150                 155                 160
Lys Ile Thr Trp Val Arg Trp Val Leu Tyr Ala Val Ser Leu Phe Leu
                165                 170                 175
Pro Leu Phe Ile Ile Tyr Ser Met Val Arg Pro Pro Asp Lys Asn Asn
                180                 185                 190
Arg Tyr Val Gly Leu Tyr Cys Thr Leu Val Ser Cys Val Glu Trp Leu
         195                 200                 205
Ala Ala Ala Val Val Leu Tyr Phe Cys Gly Val Ile Val Asp Val His
         210                 215                 220
Val Ser Phe Met Ser Phe Ile Ala Ile Phe Ile Ala Ala Leu Ser
225                 230                 235                 240
Gly Leu Val Ser Phe Ile Pro Gly Gly Phe Gly Ala Phe Asp Leu Val
                245                 250                 255
Val Leu Leu Gly Phe Lys Thr Leu Gly Val Pro Glu Glu Lys Val Leu
                260                 265                 270
Leu Met Leu Leu Leu Tyr Arg Phe Ala Tyr Tyr Phe Val Pro Val Ile
         275                 280                 285
Ile Ala Leu Ile Leu Ser Ser Phe Glu Phe Gly Thr Ser Ala Lys Lys
 290                 295                 300
Tyr Ile Glu Gly Ser Lys Tyr Phe Ile Pro Ala Lys Asp Val Thr Ser
305                 310                 315                 320
Phe Leu Met Ser Tyr Gln Lys Asp Ile Ile Ala Lys Ile Pro Ser Leu
                325                 330                 335
Ser Leu Ala Ile Leu Val Phe Phe Thr Ser Met Ile Phe Phe Val Asn
                340                 345                 350
Asn Leu Thr Ile Val Tyr Asp Ala Leu Tyr Asp Gly Asn His Leu Thr
         355                 360                 365
Tyr Tyr Leu Leu Leu Ala Ile His Thr Ser Ala Cys Leu Leu Leu Leu
 370                 375                 380
Leu Asn Val Val Gly Ile Tyr Lys Gln Ser Arg Arg Ala Ile Ile Tyr
385                 390                 395                 400
Ala Met Ile Ser Ile Ile Leu Ile Ile Val Ala Thr Leu Phe Thr Tyr
                405                 410                 415
Ala Ser Tyr Ile Leu Ile Thr Trp Leu Val Ile Phe Ala Leu Leu
                420                 425                 430
Ile Val Ala Phe Arg Arg Ala Arg Arg Leu Lys Arg Pro Ile Arg Met
         435                 440                 445
Arg Asn Leu Val Ala Met Leu Leu Phe Ser Ile Phe Ile Leu Tyr Ile
     450                 455                 460
```

```
Asn His Ile Phe Ile Ala Gly Thr Phe Tyr Ala Leu Asp Val Tyr Thr
465                 470                 475                 480

Ile Glu Met His Thr Ser Val Leu Lys Tyr Tyr Phe Trp Ile Thr Ile
                485                 490                 495

Leu Ile Ile Ala Ile Ile Val Gly Ala Ile Ala Trp Leu Phe Asp Tyr
            500                 505                 510

Gln Phe Ser Lys Val Arg Ile Ser Ser Asn Ile Glu Glu Cys Glu Glu
        515                 520                 525

Ile Ile Asp Gln Tyr Gly Gly Asn Tyr Leu Ser His Leu Ile Tyr Ser
530                 535                 540

Gly Asp Lys Gln Phe Phe Thr Asn Glu Asp Lys Asn Ala Phe Leu Met
545                 550                 555                 560

Tyr Arg Tyr Lys Ala Ser Ser Leu Val Val Leu Gly Asp Pro Ile Gly
                565                 570                 575

Asp Glu Asn Ala Phe Asp Glu Leu Leu Glu Ala Phe Tyr Asn Tyr Ala
            580                 585                 590

Glu Tyr Leu Gly Tyr Asp Val Ile Phe Tyr Gln Val Thr Asp Gln His
        595                 600                 605

Met Pro Leu Tyr His Asn Phe Gly Asn Gln Phe Phe Lys Leu Gly Glu
610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655

Phe Glu Ile Ile Glu Pro Pro Phe Ser Thr Glu Phe Ile Asn Glu Leu
            660                 665                 670

Gln His Val Ser Asp Leu Trp Leu Asp Asn Arg Gln Glu Met His Phe
        675                 680                 685

Ser Val Gly Gln Phe Asn Glu Thr Tyr Leu Ser Lys Ala Pro Ile Gly
690                 695                 700

Val Met Arg Asn Glu Asn Asn Glu Val Ile Ala Phe Cys Ser Leu Met
705                 710                 715                 720

Pro Thr Tyr Phe Asn Asp Ala Ile Ser Val Asp Leu Ile Arg Trp Leu
                725                 730                 735

Pro Glu Leu Asp Leu Pro Leu Met Asp Gly Leu Tyr Leu His Met Leu
            740                 745                 750

Leu Trp Ser Lys Glu Gln Gly Tyr Thr Lys Phe Asn Met Gly Met Ala
        755                 760                 765

Thr Leu Ser Asn Val Gly Gln Leu His Tyr Ser Tyr Leu Arg Glu Arg
770                 775                 780

Leu Ala Gly Arg Val Phe Glu His Phe Asn Gly Leu Tyr Arg Phe Gln
785                 790                 795                 800

Gly Leu Arg Arg Tyr Lys Ser Lys Tyr Asn Pro Asn Trp Glu Pro Arg
                805                 810                 815

Phe Leu Val Tyr Arg Lys Asp Asn Ser Leu Trp Glu Ser Leu Ser Lys
            820                 825                 830

Val Met Arg Val Ile Arg His Lys
        835                 840

<210> SEQ ID NO 115
<211> LENGTH: 840
<212> TYPE: PRT
<213> ORGANISM: Staphylococcus aureus
<220> FEATURE:
<223> OTHER INFORMATION: MSSA479
```

<400> SEQUENCE: 115

| | | | | | | | | | | | | | | |
|---|---|---|---|---|---|---|---|---|---|---|---|---|---|---|
|Met|Asn|Gln|Glu|Val|Lys|Asn|Lys|Ile|Phe|Ser|Ile|Leu|Lys|Ile|Thr|
|1| | | |5| | | | |10| | | | |15| |

Phe Ala Thr Ala Leu Phe Ile Phe Val Val Ile Thr Leu Tyr Arg Glu
                20                  25                  30

Leu Ser Gly Ile Asn Phe Lys Asp Thr Leu Val Glu Phe Ser Lys Ile
            35                  40                  45

Asn Arg Met Ser Leu Val Leu Leu Phe Ile Gly Gly Ala Ser Leu
    50                  55                  60

Val Ile Leu Ser Met Tyr Asp Val Ile Leu Ser Arg Ala Leu Lys Met
65                  70                  75                  80

Asp Ile Ser Leu Gly Lys Val Leu Arg Val Ser Tyr Ile Ile Asn Ala
                85                  90                  95

Leu Asn Ala Ile Val Gly Phe Gly Phe Ile Gly Ala Gly Val Arg
                100                 105                 110

Ala Met Val Tyr Lys Asn Tyr Thr His Asp Lys Lys Leu Val His
                115                 120                 125

Phe Ile Ser Leu Ile Leu Ile Ser Met Leu Thr Gly Leu Ser Leu Leu
130                 135                 140

Ser Leu Leu Ile Val Phe His Val Phe Asp Ala Ser Leu Ile Leu Asp
145                 150                 155                 160

Lys Ile Thr Trp Val Arg Trp Val Leu Tyr Val Val Ser Phe Phe Leu
                165                 170                 175

Pro Leu Phe Ile Ile Tyr Ser Met Val Arg Pro Pro Asp Lys Asn Asn
                180                 185                 190

Arg Phe Val Gly Leu Tyr Cys Thr Leu Val Ser Cys Val Glu Trp Leu
                195                 200                 205

Ala Ala Ala Val Val Leu Tyr Phe Cys Gly Val Ile Val Asp Ala His
210                 215                 220

Val Ser Phe Met Ser Phe Ile Ala Ile Phe Ile Ala Ala Leu Ser
225                 230                 235                 240

Gly Leu Val Ser Phe Ile Pro Gly Gly Phe Gly Ala Phe Asp Leu Val
                245                 250                 255

Val Leu Leu Gly Phe Lys Thr Leu Gly Val Pro Glu Glu Lys Val Leu
                260                 265                 270

Leu Met Leu Leu Leu Tyr Arg Phe Ala Tyr Tyr Phe Val Pro Val Ile
            275                 280                 285

Ile Ala Leu Ile Leu Ser Ser Phe Glu Phe Gly Thr Ser Ala Lys Lys
    290                 295                 300

Tyr Ile Glu Gly Ser Lys Tyr Phe Ile Pro Ala Lys Asp Val Thr Ser
305                 310                 315                 320

Phe Leu Met Ser Tyr Gln Lys Asp Ile Ile Ala Lys Ile Pro Ser Leu
                325                 330                 335

Ser Leu Ala Ile Leu Val Phe Phe Thr Ser Met Ile Phe Phe Val Asn
                340                 345                 350

Asn Leu Thr Ile Val Tyr Asp Ala Leu Tyr Asp Gly Asn His Leu Thr
                355                 360                 365

Tyr Tyr Ile Leu Leu Ala Ile His Thr Ser Ala Cys Leu Leu Leu Leu
                370                 375                 380

Leu Asn Val Val Gly Ile Tyr Lys Gln Ser Arg Arg Ala Ile Ile Phe
385                 390                 395                 400

Ala Met Ile Ser Ile Leu Leu Ile Thr Val Ala Thr Phe Phe Thr Tyr

```
                      405                 410                 415
Ala Ser Tyr Ile Leu Ile Thr Trp Leu Ala Ile Ile Phe Val Leu Leu
                420                 425                 430

Ile Val Ala Phe Arg Arg Ala Arg Arg Leu Lys Arg Pro Val Arg Met
                435                 440                 445

Arg Asn Ile Val Ala Met Leu Leu Phe Ser Leu Phe Ile Leu Tyr Val
            450                 455                 460

Asn His Ile Phe Ile Ala Gly Thr Leu Tyr Ala Leu Asp Ile Tyr Thr
465                 470                 475                 480

Ile Glu Met His Thr Ser Val Leu Arg Tyr Tyr Phe Trp Leu Thr Ile
                485                 490                 495

Leu Ile Ile Ala Ile Ile Ile Gly Met Ile Ala Trp Leu Phe Asp Tyr
                500                 505                 510

Gln Phe Ser Lys Val Arg Ile Ser Ser Lys Ile Glu Asp Cys Glu Glu
                515                 520                 525

Ile Ile Asn Gln Tyr Gly Gly Asn Tyr Leu Ser His Leu Ile Tyr Ser
            530                 535                 540

Gly Asp Lys Gln Phe Phe Thr Asn Glu Asn Lys Thr Ala Phe Leu Met
545                 550                 555                 560

Tyr Arg Tyr Lys Ala Ser Ser Leu Val Val Leu Gly Asp Pro Leu Gly
                565                 570                 575

Asp Glu Asn Ala Phe Asp Glu Leu Leu Glu Ala Phe Tyr Asn Tyr Ala
                580                 585                 590

Glu Tyr Leu Gly Tyr Asp Val Ile Phe Tyr Gln Val Thr Asp Gln His
                595                 600                 605

Met Pro Leu Tyr His Asn Phe Gly Asn Gln Phe Phe Lys Leu Gly Glu
            610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655

Phe Glu Ile Ile Glu Pro Pro Phe Ser Thr Glu Phe Ile Asn Glu Leu
                660                 665                 670

Gln His Val Ser Asp Leu Trp Leu Asp Asn Arg Gln Glu Met His Phe
            675                 680                 685

Ser Val Gly Gln Phe Asn Glu Glu Tyr Leu Ser Lys Ala Pro Ile Gly
            690                 695                 700

Val Met Arg Asn Glu Glu Asn Glu Val Ile Ala Phe Cys Ser Leu Met
705                 710                 715                 720

Pro Thr Tyr Phe Asn Asp Ala Ile Ser Val Asp Leu Ile Arg Trp Leu
                725                 730                 735

Pro Glu Leu Asp Leu Pro Leu Met Asp Gly Leu Tyr Leu His Met Leu
                740                 745                 750

Leu Trp Ser Lys Glu Gln Gly Tyr Thr Lys Phe Asn Met Gly Met Ala
                755                 760                 765

Thr Leu Ser Asn Val Gly Gln Leu His Tyr Ser Tyr Leu Arg Glu Arg
            770                 775                 780

Leu Ala Gly Arg Val Phe Glu His Phe Asn Gly Leu Tyr Arg Phe Gln
785                 790                 795                 800

Gly Leu Arg Arg Tyr Lys Ser Lys Tyr Asn Pro Asn Trp Glu Pro Arg
                805                 810                 815

Phe Leu Val Tyr Arg Lys Asp Asn Ser Leu Trp Glu Ser Leu Ser Lys
                820                 825                 830
```

```
Val Met Arg Val Ile Arg His Lys
        835                 840

<210> SEQ ID NO 116
<211> LENGTH: 840
<212> TYPE: PRT
<213> ORGANISM: Staphylococcus aureus
<220> FEATURE:
<223> OTHER INFORMATION: MW2

<400> SEQUENCE: 116

Met Asn Gln Glu Val Lys Asn Lys Ile Phe Ser Ile Leu Lys Ile Thr
1               5                   10                  15

Phe Ala Thr Ala Leu Phe Ile Phe Val Ile Thr Leu Tyr Arg Glu
            20                  25                  30

Leu Ser Gly Ile Asn Phe Lys Asp Thr Leu Val Glu Phe Ser Lys Ile
            35                  40                  45

Asn Arg Met Ser Leu Val Leu Leu Phe Ile Gly Gly Ala Ser Leu
        50                  55                  60

Val Ile Leu Ser Met Tyr Asp Val Ile Leu Ser Arg Ala Leu Lys Met
65                  70                  75                  80

Asp Ile Ser Leu Gly Lys Val Leu Arg Val Ser Tyr Ile Ile Asn Ala
                85                  90                  95

Leu Asn Ala Ile Val Gly Phe Gly Gly Phe Ile Gly Ala Gly Val Arg
            100                 105                 110

Ala Met Val Tyr Lys Asn Tyr Thr His Asp Lys Lys Lys Leu Val His
            115                 120                 125

Phe Ile Ser Leu Ile Leu Ile Ser Met Leu Thr Gly Leu Ser Leu Leu
        130                 135                 140

Ser Leu Leu Ile Val Phe His Val Phe Asp Ala Ser Leu Ile Leu Asp
145                 150                 155                 160

Lys Ile Thr Trp Val Arg Trp Val Leu Tyr Val Val Ser Phe Phe Leu
                165                 170                 175

Pro Leu Phe Ile Ile Tyr Ser Met Val Arg Pro Pro Asp Lys Asn Asn
            180                 185                 190

Arg Phe Val Gly Leu Tyr Cys Thr Leu Val Ser Cys Val Glu Trp Leu
        195                 200                 205

Ala Ala Ala Val Val Leu Tyr Phe Cys Gly Val Ile Val Asp Ala His
    210                 215                 220

Val Ser Phe Met Ser Phe Ile Ala Ile Phe Ile Ala Ala Leu Ser
225                 230                 235                 240

Gly Leu Val Ser Phe Ile Pro Gly Gly Phe Gly Ala Phe Asp Leu Val
                245                 250                 255

Val Leu Leu Gly Phe Lys Thr Leu Gly Val Pro Glu Glu Lys Val Leu
            260                 265                 270

Leu Met Leu Leu Leu Tyr Arg Phe Ala Tyr Tyr Phe Val Pro Val Ile
        275                 280                 285

Ile Ala Leu Ile Leu Ser Ser Phe Glu Phe Gly Thr Ser Ala Lys Lys
    290                 295                 300

Tyr Ile Glu Gly Ser Lys Tyr Phe Ile Pro Ala Lys Asp Val Thr Ser
305                 310                 315                 320

Phe Leu Met Ser Tyr Gln Lys Asp Ile Ile Ala Lys Ile Pro Ser Leu
                325                 330                 335

Ser Leu Ala Ile Leu Val Phe Phe Thr Ser Met Ile Phe Phe Val Asn
            340                 345                 350
```

-continued

```
Asn Leu Thr Ile Val Tyr Asp Ala Leu Tyr Asp Gly Asn His Leu Thr
            355                 360                 365

Tyr Tyr Ile Leu Leu Ala Ile His Thr Ser Ala Cys Leu Leu Leu Leu
    370                 375                 380

Leu Asn Val Val Gly Ile Tyr Lys Gln Ser Arg Arg Ala Ile Ile Phe
385                 390                 395                 400

Ala Met Ile Ser Ile Leu Leu Ile Thr Val Ala Thr Phe Phe Thr Tyr
                405                 410                 415

Ala Ser Tyr Ile Leu Ile Thr Trp Leu Ala Ile Ile Phe Val Leu Leu
                420                 425                 430

Ile Val Ala Phe Arg Arg Ala Arg Arg Leu Lys Arg Pro Val Arg Met
            435                 440                 445

Arg Asn Ile Val Ala Met Leu Leu Phe Ser Leu Phe Ile Leu Tyr Val
    450                 455                 460

Asn His Ile Phe Ile Ala Gly Thr Leu Tyr Ala Leu Asp Ile Tyr Thr
465                 470                 475                 480

Ile Glu Met His Thr Ser Val Leu Arg Tyr Tyr Phe Trp Leu Thr Ile
                485                 490                 495

Leu Ile Ile Ala Ile Ile Gly Met Ile Ala Trp Leu Phe Asp Tyr
                500                 505                 510

Gln Phe Ser Lys Val Arg Ile Ser Ser Lys Ile Glu Asp Cys Glu Glu
            515                 520                 525

Ile Ile Asn Gln Tyr Gly Gly Asn Tyr Leu Ser His Leu Ile Tyr Ser
    530                 535                 540

Gly Asp Lys Gln Phe Phe Thr Asn Glu Asn Lys Thr Ala Phe Leu Met
545                 550                 555                 560

Tyr Arg Tyr Lys Ala Ser Ser Leu Val Val Leu Gly Asp Pro Leu Gly
                565                 570                 575

Asp Glu Asn Ala Phe Asp Glu Leu Leu Glu Ala Phe Tyr Asn Tyr Ala
            580                 585                 590

Glu Tyr Leu Gly Tyr Asp Val Ile Phe Tyr Gln Val Thr Asp Gln His
    595                 600                 605

Met Pro Leu Tyr His Asn Phe Gly Asn Gln Phe Lys Leu Gly Glu
            610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655

Phe Glu Ile Ile Glu Pro Pro Phe Ser Thr Glu Phe Ile Asn Glu Leu
                660                 665                 670

Gln His Val Ser Asp Leu Trp Leu Asp Asn Arg Gln Glu Met His Phe
            675                 680                 685

Ser Val Gly Gln Phe Asn Glu Glu Tyr Leu Ser Lys Ala Pro Ile Gly
    690                 695                 700

Val Met Arg Asn Glu Glu Asn Glu Val Ile Ala Phe Cys Ser Leu Met
705                 710                 715                 720

Pro Thr Tyr Phe Asn Asp Ala Ile Ser Val Asp Leu Ile Arg Trp Leu
                725                 730                 735

Pro Glu Leu Asp Leu Pro Leu Met Asp Gly Leu Tyr Leu His Met Leu
            740                 745                 750

Leu Trp Ser Lys Glu Gln Gly Tyr Thr Lys Phe Asn Met Gly Met Ala
    755                 760                 765
```

```
Thr Leu Ser Asn Val Gly Gln Leu His Tyr Ser Tyr Leu Arg Glu Arg
            770                 775                 780
Leu Ala Gly Arg Val Phe Glu His Phe Asn Gly Leu Tyr Arg Phe Gln
785                 790                 795                 800
Gly Leu Arg Arg Tyr Lys Ser Lys Tyr Asn Pro Asn Trp Glu Pro Arg
                805                 810                 815
Phe Leu Val Tyr Arg Lys Asp Asn Ser Leu Trp Glu Ser Leu Ser Lys
                820                 825                 830
Val Met Arg Val Ile Arg His Lys
                835                 840

<210> SEQ ID NO 117
<211> LENGTH: 840
<212> TYPE: PRT
<213> ORGANISM: Staphylococcus aureus
<220> FEATURE:
<223> OTHER INFORMATION: N315

<400> SEQUENCE: 117

Met Asn Gln Glu Val Lys Asn Lys Ile Phe Ser Ile Leu Lys Ile Thr
1               5                   10                  15
Phe Ala Thr Ala Leu Phe Ile Phe Val Ala Ile Thr Leu Tyr Arg Glu
                20                  25                  30
Leu Ser Gly Ile Asn Phe Lys Asp Thr Leu Val Glu Phe Ser Lys Ile
            35                  40                  45
Asn Arg Met Ser Leu Val Leu Leu Phe Ile Gly Gly Ala Ser Leu
    50                  55                  60
Val Ile Leu Ser Met Tyr Asp Val Ile Leu Ser Arg Ala Leu Lys Met
65                  70                  75                  80
Asp Ile Ser Leu Gly Lys Val Leu Arg Val Ser Tyr Ile Ile Asn Ala
                85                  90                  95
Leu Asn Ala Ile Val Gly Phe Gly Phe Ile Gly Ala Gly Val Arg
            100                 105                 110
Ala Met Val Tyr Lys Asn Tyr Thr His Asp Lys Lys Lys Leu Val His
            115                 120                 125
Phe Ile Ser Leu Ile Leu Ile Ser Met Leu Thr Gly Leu Ser Leu Leu
        130                 135                 140
Ser Leu Leu Ile Val Phe His Val Phe Asp Ala Ser Leu Ile Leu Asp
145                 150                 155                 160
Lys Ile Thr Trp Val Arg Trp Val Leu Tyr Val Ser Phe Phe Leu
            165                 170                 175
Pro Leu Phe Ile Ile Tyr Ser Met Val Arg Pro Pro Asp Lys Asn Asn
                180                 185                 190
Arg Phe Val Gly Leu Tyr Cys Thr Leu Val Ser Cys Val Glu Trp Leu
                195                 200                 205
Ala Ala Ala Val Val Leu Tyr Phe Cys Gly Val Ile Val Asp Ala His
    210                 215                 220
Val Ser Phe Met Ser Phe Ile Ala Ile Phe Ile Ala Ala Leu Ser
225                 230                 235                 240
Gly Leu Val Ser Phe Ile Pro Gly Gly Phe Gly Ala Phe Asp Leu Val
                245                 250                 255
Val Leu Leu Gly Phe Lys Thr Leu Gly Val Pro Glu Glu Lys Val Leu
                260                 265                 270
Leu Met Leu Leu Leu Tyr Arg Phe Ala Tyr Tyr Phe Val Pro Val Ile
            275                 280                 285
```

```
Ile Ala Leu Ile Leu Ser Ser Phe Glu Phe Gly Thr Ser Ala Lys Lys
290                 295                 300

Tyr Ile Glu Gly Ser Lys Tyr Phe Ile Pro Ala Lys Asp Val Thr Ser
305                 310                 315                 320

Phe Leu Met Ser Tyr Gln Lys Asp Ile Ala Lys Ile Pro Ser Leu
                325                 330                 335

Ser Leu Ala Ile Leu Val Phe Phe Thr Ser Met Ile Phe Val Asn
            340                 345                 350

Asn Leu Thr Ile Val Tyr Asp Ala Leu Tyr Asp Gly Asn His Leu Thr
            355                 360                 365

Tyr Tyr Ile Leu Leu Ala Ile His Thr Ser Ala Cys Leu Leu Leu Leu
370                 375                 380

Leu Asn Val Val Gly Ile Tyr Lys Gln Ser Arg Arg Ala Ile Ile Phe
385                 390                 395                 400

Ala Met Ile Ser Ile Leu Leu Ile Thr Val Ala Thr Phe Phe Thr Tyr
                405                 410                 415

Ala Ser Tyr Ile Leu Ile Thr Trp Leu Ala Ile Ile Phe Val Leu Leu
                420                 425                 430

Ile Val Ala Phe Arg Arg Ala Arg Arg Leu Lys Arg Pro Val Arg Met
            435                 440                 445

Arg Asn Ile Val Ala Met Leu Leu Phe Ser Leu Phe Ile Leu Tyr Val
450                 455                 460

Asn His Ile Phe Ile Ala Gly Thr Leu Tyr Ala Leu Asp Ile Tyr Thr
465                 470                 475                 480

Ile Glu Met His Thr Ser Val Leu Arg Tyr Tyr Phe Trp Leu Thr Ile
                485                 490                 495

Leu Ile Ile Ala Ile Ile Gly Met Ile Ala Trp Leu Phe Asp Tyr
            500                 505                 510

Gln Phe Ser Lys Val Arg Ile Ser Ser Lys Ile Glu Asp Cys Glu Glu
            515                 520                 525

Ile Ile Asn Gln Tyr Gly Gly Asn Tyr Leu Ser His Leu Ile Tyr Ser
530                 535                 540

Gly Asp Lys Gln Phe Phe Thr Asn Glu Asn Lys Thr Ala Phe Leu Met
545                 550                 555                 560

Tyr Arg Tyr Lys Ala Ser Ser Leu Val Val Leu Gly Asp Pro Leu Gly
                565                 570                 575

Asp Glu Asn Ala Phe Asp Glu Leu Leu Glu Ala Phe Tyr Asn Tyr Ala
            580                 585                 590

Glu Tyr Leu Gly Tyr Asp Val Ile Phe Tyr Gln Val Thr Asp Gln His
            595                 600                 605

Met Pro Leu Tyr His Asn Phe Gly Asn Gln Phe Phe Lys Leu Gly Glu
610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655

Phe Glu Ile Ile Glu Pro Pro Phe Ser Thr Glu Phe Ile Asn Glu Leu
                660                 665                 670

Gln His Val Ser Asp Leu Trp Leu Asp Asn Arg Gln Glu Met His Phe
            675                 680                 685

Ser Val Gly Gln Phe Asn Glu Glu Tyr Leu Ser Lys Ala Pro Ile Gly
            690                 695                 700

Val Met Arg Asn Glu Glu Asn Glu Val Ile Ala Phe Cys Ser Leu Met
```

```
              705                 710                 715                 720
        Pro Thr Tyr Phe Asn Asp Ala Ile Ser Val Asp Leu Ile Arg Trp Leu
                        725                 730                 735

Pro Glu Leu Asp Leu Pro Leu Met Asp Gly Leu Tyr Leu His Met Leu
                        740                 745                 750

Leu Trp Ser Lys Glu Gln Gly Tyr Thr Lys Phe Asn Met Gly Met Ala
                        755                 760                 765

Thr Leu Ser Asn Val Gly Gln Leu His Tyr Ser Tyr Leu Arg Glu Arg
                        770                 775                 780

Leu Ala Gly Arg Val Phe Glu His Phe Asn Gly Leu Tyr Arg Phe Gln
        785                 790                 795                 800

Gly Leu Arg Arg Tyr Lys Ser Lys Tyr Asn Pro Asn Trp Glu Pro Arg
                        805                 810                 815

Phe Leu Val Tyr Arg Lys Asp Asn Ser Leu Trp Glu Ser Leu Ser Lys
                        820                 825                 830

Val Met Arg Val Ile Arg His Lys
                        835                 840

<210> SEQ ID NO 118
<211> LENGTH: 840
<212> TYPE: PRT
<213> ORGANISM: Staphylococcus aureus
<220> FEATURE:
<223> OTHER INFORMATION: USA300

<400> SEQUENCE: 118

Met Asn Gln Glu Val Lys Asn Lys Ile Phe Ser Ile Leu Lys Ile Thr
        1               5                   10                  15

Phe Ala Thr Ala Leu Phe Ile Phe Val Ala Ile Thr Leu Tyr Arg Glu
                        20                  25                  30

Leu Ser Gly Ile Asn Phe Lys Asp Thr Leu Val Glu Phe Ser Lys Ile
                        35                  40                  45

Asn Arg Met Ser Leu Val Leu Leu Phe Ile Gly Gly Gly Ala Ser Leu
                        50                  55                  60

Val Ile Leu Ser Met Tyr Asp Val Ile Leu Ser Arg Ala Leu Lys Met
        65                  70                  75                  80

Asp Ile Ser Leu Gly Lys Val Leu Arg Val Ser Tyr Ile Ile Asn Ala
                        85                  90                  95

Leu Asn Ala Ile Val Gly Phe Gly Gly Phe Ile Gly Ala Gly Val Arg
                        100                 105                 110

Ala Met Val Tyr Lys Asn Tyr Thr His Asp Lys Lys Leu Val His
                        115                 120                 125

Phe Ile Ser Leu Ile Leu Ile Ser Met Leu Thr Gly Leu Ser Leu Leu
                        130                 135                 140

Ser Leu Leu Ile Val Phe His Val Phe Asp Ala Ser Leu Ile Leu Asp
        145                 150                 155                 160

Lys Ile Thr Trp Val Arg Trp Val Leu Tyr Val Val Ser Phe Phe Leu
                        165                 170                 175

Pro Leu Phe Ile Ile Tyr Ser Met Val Arg Pro Pro Asp Lys Asn Asn
                        180                 185                 190

Arg Phe Val Gly Leu Tyr Cys Thr Leu Val Ser Cys Val Glu Trp Leu
                        195                 200                 205

Ala Ala Ala Val Val Leu Tyr Phe Cys Gly Val Ile Val Asp Ala His
                        210                 215                 220

Val Ser Phe Met Ser Phe Ile Ala Ile Phe Ile Ile Ala Ala Leu Ser
```

```
            225                 230                 235                 240
Gly Leu Val Ser Phe Ile Pro Gly Gly Phe Ala Phe Asp Leu Val
                245                 250                 255

Val Leu Leu Gly Phe Lys Thr Leu Gly Val Pro Glu Glu Lys Val Leu
                260                 265                 270

Leu Met Leu Leu Leu Tyr Arg Phe Ala Tyr Tyr Phe Val Pro Val Ile
                275                 280                 285

Ile Ala Leu Ile Leu Ser Ser Phe Glu Phe Gly Thr Ser Ala Lys Lys
                290                 295                 300

Tyr Ile Glu Gly Ser Lys Tyr Phe Ile Pro Ala Lys Asp Val Thr Ser
305                 310                 315                 320

Phe Leu Met Ser Tyr Gln Lys Asp Ile Ile Ala Lys Ile Pro Ser Leu
                325                 330                 335

Ser Leu Ala Ile Leu Val Phe Phe Thr Ser Met Ile Phe Phe Val Asn
                340                 345                 350

Asn Leu Thr Ile Val Tyr Asp Ala Leu Tyr Asp Gly Asn His Leu Thr
                355                 360                 365

Tyr Tyr Ile Leu Leu Ala Ile His Thr Ser Ala Cys Leu Leu Leu Leu
        370                 375                 380

Leu Asn Val Val Gly Ile Tyr Lys Gln Ser Arg Arg Ala Ile Ile Phe
385                 390                 395                 400

Ala Met Ile Ser Ile Leu Leu Ile Thr Val Ala Thr Phe Phe Thr Tyr
                405                 410                 415

Ala Ser Tyr Ile Leu Ile Thr Trp Leu Ala Ile Ile Phe Val Leu Leu
                420                 425                 430

Ile Val Ala Phe Arg Arg Ala Arg Arg Leu Lys Arg Pro Val Arg Met
            435                 440                 445

Arg Asn Ile Val Ala Met Leu Leu Phe Ser Leu Phe Ile Leu Tyr Val
                450                 455                 460

Asn His Ile Phe Ile Ala Gly Thr Leu Tyr Ala Leu Asp Ile Tyr Thr
465                 470                 475                 480

Ile Glu Met His Thr Ser Val Leu Arg Tyr Tyr Phe Trp Leu Thr Ile
                485                 490                 495

Leu Ile Ile Ala Ile Ile Ile Gly Met Ile Ala Trp Leu Phe Asp Tyr
                500                 505                 510

Gln Phe Ser Lys Val Arg Ile Ser Ser Lys Ile Glu Asp Cys Glu Glu
                515                 520                 525

Ile Ile Asn Gln Tyr Gly Gly Asn Tyr Leu Ser His Leu Ile Tyr Ser
                530                 535                 540

Gly Asp Lys Gln Phe Phe Thr Asn Glu Asn Lys Thr Ala Phe Leu Met
545                 550                 555                 560

Tyr Arg Tyr Lys Ala Ser Ser Leu Val Val Leu Gly Asp Pro Leu Gly
                565                 570                 575

Asp Glu Asn Ala Phe Asp Glu Leu Leu Glu Ala Phe Tyr Asn Tyr Ala
                580                 585                 590

Glu Tyr Leu Gly Tyr Asp Val Ile Phe Tyr Gln Val Thr Asp Gln His
                595                 600                 605

Met Pro Leu Tyr His Asn Phe Gly Asn Gln Phe Phe Lys Leu Gly Glu
                610                 615                 620

Glu Ala Ile Ile Asp Leu Thr Gln Phe Ser Thr Ser Gly Lys Lys Arg
625                 630                 635                 640

Arg Gly Phe Arg Ala Thr Leu Asn Lys Phe Asp Glu Leu Asn Ile Ser
                645                 650                 655
```

```
Phe Glu Ile Ile Glu Pro Pro Phe Ser Thr Glu Phe Ile Asn Glu Leu
            660                 665                 670

Gln His Val Ser Asp Leu Trp Leu Asp Asn Arg Gln Glu Met His Phe
        675                 680                 685

Ser Val Gly Glu Phe Asn Glu Glu Tyr Leu Ser Lys Ala Pro Ile Gly
        690                 695                 700

Val Met Arg Asn Glu Glu Asn Glu Val Ile Ala Phe Cys Ser Leu Met
705                 710                 715                 720

Pro Thr Tyr Phe Asn Asp Ala Ile Ser Val Asp Leu Ile Arg Trp Leu
            725                 730                 735

Pro Glu Leu Asp Leu Pro Leu Met Asp Gly Leu Tyr Leu His Met Leu
            740                 745                 750

Leu Trp Ser Lys Glu Gln Gly Tyr Thr Lys Phe Asn Met Gly Met Ala
            755                 760                 765

Thr Leu Ser Asn Val Gly Gln Leu His Tyr Ser Tyr Leu Arg Glu Arg
        770                 775                 780

Leu Ala Gly Arg Val Phe Glu His Phe Asn Gly Leu Tyr Arg Phe Gln
785                 790                 795                 800

Gly Leu Arg Arg Tyr Lys Ser Lys Tyr Asn Pro Asn Trp Glu Pro Arg
            805                 810                 815

Phe Leu Val Tyr Arg Lys Asp Asn Ser Leu Trp Glu Ser Leu Ser Lys
            820                 825                 830

Val Met Arg Val Ile Arg His Lys
        835                 840

<210> SEQ ID NO 119
<211> LENGTH: 9
<212> TYPE: PRT
<213> ORGANISM: Artificial Sequence
<220> FEATURE:
<223> OTHER INFORMATION: HCDR1

<400> SEQUENCE: 119

Phe Thr Phe Ser Ser Tyr Ala Ile Ser
1               5

<210> SEQ ID NO 120
<211> LENGTH: 19
<212> TYPE: PRT
<213> ORGANISM: Artificial Sequence
<220> FEATURE:
<223> OTHER INFORMATION: HCDR2

<400> SEQUENCE: 120

Val Ser Ala Ile Ser Gly Ser Gly Gly Ser Thr Tyr Tyr Ala Glu Ser
1               5                   10                  15

Val Lys Gly

<210> SEQ ID NO 121
<211> LENGTH: 9
<212> TYPE: PRT
<213> ORGANISM: Artificial Sequence
<220> FEATURE:
<223> OTHER INFORMATION: HCDR3

<400> SEQUENCE: 121

Tyr Pro Tyr Pro Gly Tyr Phe Asp Leu
1               5
```

```
<210> SEQ ID NO 122
<211> LENGTH: 11
<212> TYPE: PRT
<213> ORGANISM: Artificial Sequence
<220> FEATURE:
<223> OTHER INFORMATION: LCDR1

<400> SEQUENCE: 122

Ser Gly Asp Lys Leu Gly Asp Lys Tyr Ala Tyr
1               5                   10

<210> SEQ ID NO 123
<211> LENGTH: 11
<212> TYPE: PRT
<213> ORGANISM: Artificial Sequence
<220> FEATURE:
<223> OTHER INFORMATION: LCDR2

<400> SEQUENCE: 123

Leu Val Ile Tyr Gln Asp Ser Lys Arg Pro Ser
1               5                   10

<210> SEQ ID NO 124
<211> LENGTH: 10
<212> TYPE: PRT
<213> ORGANISM: Artificial Sequence
<220> FEATURE:
<223> OTHER INFORMATION: LCDR3

<400> SEQUENCE: 124

Gln Thr Trp Val Ser Ser Ile Ser Ala Phe
1               5                   10

<210> SEQ ID NO 125
<211> LENGTH: 110
<212> TYPE: PRT
<213> ORGANISM: Artificial Sequence
<220> FEATURE:
<223> OTHER INFORMATION: VL

<400> SEQUENCE: 125

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Tyr Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Val Ser Ser Ile Ser Ala
                85                  90                  95

Phe Val Phe Gly Gly Gly Thr Lys Leu Thr Val Leu Gly Gln
            100                 105                 110

<210> SEQ ID NO 126
<211> LENGTH: 118
<212> TYPE: PRT
<213> ORGANISM: Artificial Sequence
<220> FEATURE:
<223> OTHER INFORMATION: VH

<400> SEQUENCE: 126
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Pro Gly Tyr Phe Asp Leu Trp Gly Gln Gly Thr
            100                 105                 110

Leu Val Thr Val Ser Ser
        115
```

<210> SEQ ID NO 127
<211> LENGTH: 330
<212> TYPE: DNA
<213> ORGANISM: Artificial Sequence
<220> FEATURE:
<223> OTHER INFORMATION: VL

<400> SEQUENCE: 127

```
agctatgaac tgacccagcc gccgagcgtt agcgttagcc caggccagac cgccagcatt    60
acctgtagcg gcgacaaact gggcgacaaa tacgcctact ggtatcagca gaaaccgggc   120
cagagcccgg tgctggttat ctatcaggat agcaaacgcc cgagcggcat tccagaacgc   180
tttagcggca gcaacagcgg caacaccgcc accctgacca ttagcggcac ccaggccgaa   240
gacgaagccg attattactg ccagacttgg gtttcttcta tctctgcttt cgtgtttggc   300
ggcggtacca agctgaccgt gctgggccag                                    330
```

<210> SEQ ID NO 128
<211> LENGTH: 354
<212> TYPE: DNA
<213> ORGANISM: Artificial Sequence
<220> FEATURE:
<223> OTHER INFORMATION: VH

<400> SEQUENCE: 128

```
gaagtgcagc tgctggaaag cggtggcggt ctggtgcagc caggtggtag cctgcgcctg    60
agctgtgccg caagcggctt tacctttagc agctatgcca ttagctgggt gcgccaagca   120
ccaggcaaag cctggaatg gtgagcgcc attagcggca gcggtggcag cacctattat   180
gccgagagcg tgaaaggtcg ctttaccatt agtcgcgata acagcaaaaa caccctgtat   240
ctgcaaatga acagcctgcg ggcagaagat accgcagttt attattgcgc gcgttaccct   300
taccctggtt atttcgacct gtggggccag ggcaccctgg ttactgtctc gagc         354
```

<210> SEQ ID NO 129
<211> LENGTH: 11
<212> TYPE: PRT
<213> ORGANISM: Artificial Sequence
<220> FEATURE:
<223> OTHER INFORMATION: HCDR1

<400> SEQUENCE: 129

Asp Ser Val Ser Ser Asn Ser Ala Ala Trp Asn

```
<210> SEQ ID NO 130
<211> LENGTH: 20
<212> TYPE: PRT
<213> ORGANISM: Artificial Sequence
<220> FEATURE:
<223> OTHER INFORMATION: HCDR2

<400> SEQUENCE: 130

Leu Gly Arg Thr Tyr Tyr Arg Ser Lys Trp Tyr Asn Asp Tyr Ala Val
1               5                   10                  15

Ser Val Lys Ser
            20

<210> SEQ ID NO 131
<211> LENGTH: 14
<212> TYPE: PRT
<213> ORGANISM: Artificial Sequence
<220> FEATURE:
<223> OTHER INFORMATION: HCDR3

<400> SEQUENCE: 131

Ser Ala Glu Pro Ser Tyr Ala Tyr Tyr His Gly Phe Asp Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: LCDR1

<400> SEQUENCE: 132

Arg Ala Ser Gln Gly Ile Ser Ser Tyr Leu Ala
1               5                   10

<210> SEQ ID NO 133
<211> LENGTH: 11
<212> TYPE: PRT
<213> ORGANISM: Artificial Sequence
<220> FEATURE:
<223> OTHER INFORMATION: LCDR2

<400> SEQUENCE: 133

Leu Leu Ile Tyr Ala Ala Ser Thr Leu Gln Ser
1               5                   10

<210> SEQ ID NO 134
<211> LENGTH: 8
<212> TYPE: PRT
<213> ORGANISM: Artificial Sequence
<220> FEATURE:
<223> OTHER INFORMATION: LCDR3

<400> SEQUENCE: 134

Gln Gln Arg Ile Ile Phe Pro Gln
1               5

<210> SEQ ID NO 135
<211> LENGTH: 109
<212> TYPE: PRT
<213> ORGANISM: Artificial Sequence
<220> FEATURE:
<223> OTHER INFORMATION: VL

<400> SEQUENCE: 135
```

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Arg Ile Ile Phe Pro Gln
                85                  90                  95

Thr Phe Gly Gln Gly Thr Lys Val Glu Ile Lys Arg Thr
            100                 105

<210> SEQ ID NO 136
<211> LENGTH: 126
<212> TYPE: PRT
<213> ORGANISM: Artificial Sequence
<220> FEATURE:
<223> OTHER INFORMATION: VH

<400> SEQUENCE: 136

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65              70                  75                  80

Gln Phe Ser Leu Gln Leu Asn Ser Val Thr Pro Glu Asp Thr Ala Val
                85                  90                  95

Tyr Tyr Cys Ala Arg Ser Ala Glu Pro Ser Tyr Ala Tyr Tyr His Gly
            100                 105                 110

Phe Asp Tyr Trp Gly Gln Gly Thr Leu Val Thr Val Ser Ser
            115                 120                 125

<210> SEQ ID NO 137
<211> LENGTH: 327
<212> TYPE: DNA
<213> ORGANISM: Artificial Sequence
<220> FEATURE:
<223> OTHER INFORMATION: VL

<400> SEQUENCE: 137
gatattcagc tgacccagag cccgagcttt ctgagcgcca gcgtgggcga tcgcgtgacc      60
attacctgcc gcgccagcca gggcattagc agctatctgg cctggtatca gcagaaaccg     120
ggcaaagccc cgaaactgct gatctatgcc gccagcaccc tgcaaagcgg cgtgccaagc     180
cgctttagcg gcagcggtag cggcaccgag ttcaccctga ccattagcag cctgcaaccg     240
gaagactttg ccacctatta ttgccagcag cgtatcatct cccgcagac cttcggccag      300 ggtaccaaag tggaaatcaa gcggacc                                         327

```
<210> SEQ ID NO 138
<211> LENGTH: 378
<212> TYPE: DNA
<213> ORGANISM: Artificial Sequence
<220> FEATURE:
<223> OTHER INFORMATION: VH

<400> SEQUENCE: 138
caggtgcagc tgcaacagag cggcccaggc ctggttaaac cgagccagac cctgagcctg        60
acctgcgcca ttagcggcga tagcgttagc agcaacagcg ccgcctggaa ctggattcgc       120
cagagcccga gccgcggtct ggaatggctg ggccgcacct attatcgcag caaatggtac       180
aacgattacg ccgttagcgt gaaaagccgc attaccatta ccccggatac cagcaaaaac       240
cagttcagcc tgcaactgaa cagcgtgacc ccggaagata ccgccgtgta ttactgcgcg       300
cgtagcgcag agcctagcta cgcatactat cacggttttg actattgggg ccagggcacc       360
ctggttactg tctcgagc                                                     378
```